United States Patent
Kang

(10) Patent No.: US 11,033,579 B2
(45) Date of Patent: Jun. 15, 2021

(54) USE OF TRIENTINE TO DELIVER COPPER TO ISCHEMIC TISSUE

(71) Applicant: INNOLIFE CO., LTD., Sichuan (CN)

(72) Inventor: Yujian James Kang, Sichuan (CN)

(73) Assignee: INNOLIFE CO., LTD., Sichuan (CN)

( * ) Notice: Subject to any disclaimer, the term of this patent is extended or adjusted under 35 U.S.C. 154(b) by 28 days.

(21) Appl. No.: 15/762,484

(22) PCT Filed: Sep. 23, 2016

(86) PCT No.: PCT/CN2016/099852
§ 371 (c)(1),
(2) Date: Mar. 22, 2018

(87) PCT Pub. No.: WO2017/050271
PCT Pub. Date: Mar. 30, 2017

(65) Prior Publication Data
US 2018/0296598 A1 Oct. 18, 2018

(30) Foreign Application Priority Data
Sep. 24, 2015 (WO) ............... PCT/CN2015/090528

(51) Int. Cl.
| A61K 33/34 | (2006.01) |
| A61K 31/132 | (2006.01) |
| A61P 9/10 | (2006.01) |
| A61P 9/00 | (2006.01) |

(52) U.S. Cl.
CPC ............ *A61K 33/34* (2013.01); *A61K 31/132* (2013.01); *A61P 9/00* (2018.01); *A61P 9/10* (2018.01)

(58) Field of Classification Search
CPC .......... A61P 9/10; A61K 33/34; A61K 31/132
See application file for complete search history.

(56) References Cited

U.S. PATENT DOCUMENTS

| 4,012,221 A | 3/1977 | Walker et al. |
| 4,550,209 A | 10/1985 | Unvert et al. |
| 4,766,247 A | 8/1988 | Ford et al. |
| 4,806,517 A | 2/1989 | Vanderpool et al. |
| 4,952,607 A | 8/1990 | Sorenson et al. |
| 5,037,812 A | 8/1991 | Berners-Price et al. |
| 5,107,005 A | 4/1992 | Azuara |
| 5,124,351 A | 6/1992 | Rabinovitz et al. |
| 5,164,367 A | 11/1992 | Pickart |
| 5,225,599 A | 7/1993 | King et al. |
| 5,385,933 A | 1/1995 | Rabinovitz et al. |
| 5,480,975 A | 1/1996 | Goldberg et al. |
| RE35,458 E | 2/1997 | Azuara |
| 5,654,403 A | 8/1997 | Smith et al. |
| 6,589,987 B2 | 7/2003 | Kennedy |
| 6,951,890 B2 | 10/2005 | Cooper et al. |
| 7,365,060 B2 | 4/2008 | Rokita et al. |
| 7,390,832 B2 | 6/2008 | Rokita et al. |
| 7,459,446 B2 | 12/2008 | Baker et al. |
| 7,867,522 B2 | 1/2011 | Faryniarz et al. |
| 7,928,094 B2 | 4/2011 | Baker et al. |
| 8,034,799 B2 | 10/2011 | Cooper et al. |
| 8,299,285 B2 | 10/2012 | Dilworth et al. |
| 8,394,992 B2 | 3/2013 | Jonas et al. |
| 8,563,538 B2 | 10/2013 | Cooper et al. |
| 2003/0065026 A1 | 4/2003 | Kennedy |
| 2004/0171678 A1 | 9/2004 | Kennedy |
| 2005/0159489 A1 | 7/2005 | Baker et al. |
| 2006/0100278 A1 | 5/2006 | Cooper et al. |
| 2009/0105206 A1 | 4/2009 | Ronald |
| 2010/0160428 A1 | 6/2010 | Cooper et al. |
| 2012/0190975 A1 | 7/2012 | Chen et al. |
| 2013/0108709 A1 | 5/2013 | Cooper et al. |
| 2014/0113969 A1 | 4/2014 | Cooper et al. |
| 2014/0171508 A1 | 6/2014 | Hanson, II et al. |
| 2014/0186261 A1 | 7/2014 | Yoshii et al. |
| 2018/0099008 A1 | 4/2018 | Kang |

FOREIGN PATENT DOCUMENTS

| CN | 1476843 A | 2/2004 |
| CN | 1688301 A | 10/2005 |
| CN | 101322825 A | 12/2008 |
| CN | 101991665 A | 3/2011 |
| CN | 101991665 B | 3/2011 |
| CN | 102274347 A | 12/2011 |
| CN | 102274347 B | 12/2011 |
| CN | 102357100 A | 2/2012 |
| CN | 102614191 A | 8/2012 |

(Continued)

OTHER PUBLICATIONS

Twedt et al., "Use of 2,3,2-tetramine as a heptatic copper chelating agent for treatment of copper hepatotoxicosis in Bedlington terriers", J Am Vet Med Assoc., Jan. 1, 1988; 192 (1): 52-6.*
Liu, J. et al. "Trientine selectively delivers copper to the heart and suppresses pressure overloaded-induced cardiac hypertrophy in rats", Experimental Biology and Medicine 2018; 243: 1141-1152.*
Benbrook, D.M. (2006). "Organotypic Cultures Represent Tumor Microenvironment for Drug Testing," *Drug Discovery Today: Disease Models* 3(2):143-148.
Benita, Y. et al. (2009; E-published on Jun. 2, 2009). "An Integrative Genomics Approach Identifies Hypoxia Inducible Factor-1 (HIF-1)-Target Genes that Form the Core Response to Hypoxia," *Nucleic Acids Research* 37(14):4587-4602.
Cho, H.-Y. et al. (Aug. 2009). "Pharmacokinetic and Pharmacodynamic Modeling of a Copper-Selective Chelator (TETA) in Healthy Adults," *J Clin Pharmacol* 49(8):916-928.

(Continued)

*Primary Examiner* — Gina C Justice
(74) *Attorney, Agent, or Firm* — Morrison & Foerster LLP

(57) ABSTRACT

Methods of ischemic tissue repair and regeneration through promoting tissue redistribution and reuse of copper by administering a composition comprising a copper chelating tetramine, such as trientine. Methods and compositions for increasing intracellular copper lever and/or inducing repair of an ischemic tissue in an individual. Increased copper level in an ischemic tissue may promote copper-dependent HIF-1 transcriptional activities and tissue repair.

23 Claims, 15 Drawing Sheets

Specification includes a Sequence Listing.

(56) References Cited

FOREIGN PATENT DOCUMENTS

| | | | |
|---|---|---|---|
| CN | 103265452 A | 8/2013 | |
| CN | 103467497 A | 12/2013 | |
| CN | 103467577 A | 12/2013 | |
| CN | 103502218 A | 1/2014 | |
| CN | 103788118 A | 5/2014 | |
| CN | 103936772 A | 7/2014 | |
| CN | 103951602 A | 7/2014 | |
| CN | 105753719 A | 7/2016 | |
| EP | 262562 A2 | 4/1988 | |
| EP | 1487431 B1 | 5/2012 | |
| JP | 2006503014 A | 1/2006 | |
| PH | 21350 A | 10/1987 | |
| RS | 20050355 A | 6/2007 | |
| RU | 2183961 C1 | 6/2002 | |
| RU | 2392668 C1 | 6/2010 | |
| WO | WO-1984/04922 A1 | 12/1984 | |
| WO | WO-2001/96572 A1 | 12/2001 | |
| WO | WO-2003/077901 A1 | 9/2003 | |
| WO | 2004017956 A1 | 3/2004 | |
| WO | WO-2004/017957 A1 | 3/2004 | |
| WO | WO-2005/009338 A2 | 2/2005 | |
| WO | WO-2005/009338 A3 | 2/2005 | |
| WO | WO-2005/058294 A1 | 6/2005 | |
| WO | WO-2005/083107 A2 | 9/2005 | |
| WO | WO-2005/083107 A3 | 9/2005 | |
| WO | WO-2006/104401 A1 | 10/2006 | |
| WO | WO-2007/055598 A1 | 5/2007 | |
| WO | WO-2012/134822 A1 | 10/2012 | |
| WO | WO-2014/035465 A1 | 3/2014 | |
| WO | WO-2014/116859 A1 | 7/2014 | |
| WO | WO-2016/168993 A1 | 10/2016 | |

OTHER PUBLICATIONS

Cooper, G.J.S. et al. (Apr. 2009; e-published on Jan. 29, 2009). "A Copper (II)-Selective Chelator Ameliorates Left-Ventricular Hypertrophy in Type 2 Diabetic Patients: A Randomised Placebo-Controlled Study," *Diabetologia* 52(4):715-722.

Cooper, G.J.S. et al. (Sep. 2004). "Regeneration of the Heart in Diabetes by Selective Copper Chelation," *Diabetes* 53(9):2501-2508.

Ding, X. et al. (Apr. 2011). "The Significance of Copper Chelators in Clinical and Experimental Application," *Journal of Nutritional Biochemistry* 22(4):301-310.

Dolomanov, O.V. et al. (Apr. 9, 2009). "OLEX2: a Complete Structure Solution, Refinement and Analysis Program," *J. Appl. Cryst.* 42:339-341.

Elvidge, G.P. et al. (Jun. 2, 2006). "Concordant Regulation of Gene Expression by Hypoxia and 2-Oxoglutarate-dependent Dioxygenase Inhibition—The Role of HIF-1α, HIF-2α, and Other Pathways," *J. Biol. Chem.* 281(22):15215-15226.

Ford, E.S. et al. (Jun. 15, 2000). "Serum Copper Concentration and Coronary Heart Disease Among US Adults," *American Journal of Epidemiology* 151(12):1182-1188.

Giavaresi, G. et al. (Jun. 2005). "Blood Vessel Formation After Soft-Tissue Implantation of Hyaluronanbased Hydrogel Supplemented with Copper Ions," *Biomaterials* 26(16):3001-3008.

Gomez, E. et al. (Jun. 2000). "Longitudinal Study of Serum Copper and Zinc Levels and their Distribution in Blood Proteins After Acute Myocardinal Infarction," *J. Trace Elements Med. Biol.* 14(2):65-70.

Greer, S.N. et al. (May 30, 2012). "The Updated Biology of Hypoxia-Inducible Factor," *The EMBO Journal* 31(11):2448-2460.

Klevay, L. (Aug. 1983). "Copper and Ischemic Heart Disease," Biol Trace Elem Res. 5(4-5):245-255.

Li, Q.-F. et al. (Jan. 2014). "Copper Promotion of Angiogenesis in Isolated Rat Aortic Ring: Role of Vascular Endothelial Growth Factor," *Journal of Nutritional Biochemistry* 25(1):44-49.

Liu, W. et al. (2012). "Targeted Genes and Interacting Proteins of Hypoxia Inducible Factor-1," *Int J Biochem Mol Biol* 3(2):165-178.

Lu, J. (Sep. 2010; e-published on Jul. 26, 2010). "Triethylenetetramine Pharmacology and its Clinical Applications," *Molecular Cancer Therapeutics* 9(9):2458-2467.

Lu, J. et al. (Feb. 2007; e-published on Nov. 15, 2006). "Triethylenetetramine and Metabolites: Levels in Relation to Copper and Zinc Excretion in Urine of Healthy Volunteers and Type 2 Diabetic Patients," *Drug Metabolism and Disposition* 35(2):221-227.

Lu, J. et al. (Jun. 2010; e-published on Feb. 9, 2010). "Pharmacokinetics and Pharmacodynamics, and Metabolism of Triethylenetetramine in Healthy Human Participants: An Open-Label Trial," *J Clin Pharmacol* 50(6):647-658.

Manalo, D.J. et al. (Jan. 15, 2005; e-published on Sep. 16, 2004). "Transcriptional Regulation of Vascular Endothelial Cell Responses to Hypoxia by HIF-1," *Blood* 105(2):659-669.

Nathan, C. et al. (May 2013). "Beyond Oxidative Stress: An Immunologist's Guide to Reactive Oxygen Species," *Nature Reviews Immunology* 13(5):349-361.

Nurchi, V.M. et al. (May 7, 2013; e-published on Dec. 3, 2012). "Complex Formation Equilibria of $CU^{II}$ and $ZN^{II}$ with Triethylenetetramine and its Mono- and Diacetyl Metabolites," *Dalton Trans.* 42(17):6161-6170.

Palatinus, L. et al. (2008). "Symmetry Determination Following Structure Solution in P 1," *J. Appl. Cryst.* 41(6):975-984.

Palatinus, L. et al. (2012). "EDMA: A Computer Program for Topological Analysis of Discrete Electron Densities," *J. Appl. Cryst.* 45:575-580.

Paul, S.A.M. et al. (Jul. 2004). "HIF at the Crossroads Between Ischemia and Carcinogenesis," *Journal of Cellular Physiology* 200(1):20-30.

Shao, T. et al. (Mar. 31, 2000). "Change and Influence of Content of Zinc and Copper in Acute Myocardial Ischemic," *Journal of Luoyang Medical College* 18(1):15-17, English Abstract only.

Sheldrick, G.M. (Jan. 2008). "A Short History of SHELX," *Acta Cryst.* A64(1):112-122.

Shen, C. et al. (May 27, 2005; e-published on Mar. 21, 2005). "Roles of the HIF-1 Hypoxia-Inducible Factor During Hypoxia Response in *Caenorhabditis elegans,*" *The Journal of Biological Chemistry* 280(21):20580-20588, (includes Supplementary Material also).

Singh, M.M. et al. (Aug. 1985). "Serum Copper in Myocardial Infarction—Diagnostic and Prognostic Significance," *Angiology—Journal of Vascular Diseases* pp. 504-510.

Tongxian, S. et al. (Mar. 2000). "Change and influence of Content of Zinc and Copper in Acute Myocardial Ischemic," *Journal of Luoyang Medical College* 18(1):15-17, English Abstract only.

Zhang, L. et al. (Dec. 31, 2013). "Protection of the Heart by Treatment with a Divalent-Copper-Selective Chelator Reveals a Novel Mechanism Underlying Cardiomyopathy in Diabetic Rats," *Cardiovascular Diabetology* 12:123, pp. 1-17.

Zhang, S. et al. (2014). "Diabetic Cardiomyopathy is Associated with Defective Myocellular Copper Regulation and Both Defects are Rectified by Divalent Copper Chelation," *Cardiovascular Diabetology* 13:100, pp. 1-18.

Zhang, Z. et al. (Oct. 2014; e-published on Aug. 7, 2014). "Copper-Dependent and -Independent Hypoxia-Inducible Factor-1 Regulation of Gene Expression," *Metallomics* 6(10):1889-1893.

Zheng, L. et al. (Apr. 2015). "Recovery of Medenchymal Stem Cells Homing to Rabbit Myocardial Ischemic Infarct Area by Cu-Microbubble Treatment," *The FASEB Journal* 29(Suppl. 1):Abstract No. 670.3, 2 pages.

Zheng, L. et al. (Apr. 2015; e-published on Dec. 1, 2014). "Role of Copper in Regression of Cardiac Hypertrophy," *Pharmacology & Therapeutics* 148:66-84.

European Search Report dated Jun. 5, 2019 for EP Application No. 16848152.1 filed Mar. 22, 2018, 7 pages.

International Search Report dated Dec. 28, 2016 for PCT Application No. PCT/CN2016/099852 filed on Sep. 23, 2016, 7 pages.

International Search Report dated Jun. 23, 2016 for PCT Application No. PCT/CN/2015/090528 filed on Sep. 24, 2015, 9 pages.

Written Opinion of the International Searching Authority dated Dec. 28, 2016 for PCT Application No. PCT/CN2016/099852 filed on Sep. 23, 2016, 5 pages.

(56) References Cited

OTHER PUBLICATIONS

Written Opinion of the International Searching Authority dated Jun. 23, 2016 for PCT Application No. PCT/CN/2015/090528 filed on Sep. 24, 2015, 4 pages.
Lu, J. et al. (Dec. 2013). Treatment with a Copper-Selective Chelator Causes Substantive Improvement in Cardiac Function of Diabetic Rats with Left-Ventricular Impairment Cardiovascular Diabetology 12(28):1-16.

\* cited by examiner

Bond lengths

| Atom | Atom | Length/Å  | Atom | Atom | Length/Å   |
|------|------|-----------|------|------|------------|
| C1   | C2   | 1.525(7)  | C5   | N3   | 1.473(5)   |
| C1   | N1   | 1.482(6)  | C6   | N4   | 1.470(5)   |
| C2   | N2   | 1.480(5)  | Cl1  | Cu1  | 2.4741(12) |
| C3   | C4   | 1.520(6)  | Cu1  | N1   | 2.026(4)   |
| C3   | N2   | 1.483(6)  | Cu1  | N2   | 2.035(4)   |
| C4   | N3   | 1.480(6)  | Cu1  | N3   | 2.026(4)   |
| C5   | C6   | 1.523(6)  | Cu1  | N4   | 2.033(4)   |

Bond angles

| Atom | Atom | Atom | Angle/° | Atom | Atom | Atom | Angle/°    |
|------|------|------|---------|------|------|------|------------|
| N1   | C1   | C2   | 106.6(4)| N3   | Cu1  | N2   | 84.54(15)  |
| N2   | C2   | C1   | 106.0(4)| N3   | Cu1  | N4   | 84.82(15)  |
| N2   | C3   | C4   | 106.6(4)| N4   | Cu1  | Cl1  | 106.67(11) |
| N3   | C4   | C3   | 109.1(4)| N4   | Cu1  | N2   | 146.08(15) |
| N3   | C5   | C6   | 107.2(4)| C1   | N1   | Cu1  | 107.6(3)   |
| N4   | C6   | C5   | 108.9(4)| C2   | N2   | C3   | 115.7(4)   |
| N1   | Cu1  | Cl1  | 99.60(11)| C2  | N2   | Cu1  | 107.0(3)   |
| N1   | Cu1  | N2   | 84.60(16)| C3  | N2   | Cu1  | 105.4(3)   |
| N1   | Cu1  | N3   | 163.99(15)| C4 | N3   | Cu1  | 109.4(3)   |
| N1   | Cu1  | N4   | 97.79(15)| C5  | N3   | C4   | 115.0(4)   |
| N2   | Cu1  | Cl1  | 106.25(11)| C5 | N3   | Cu1  | 105.9(3)   |
| N3   | Cu1  | Cl1  | 94.72(10)| C6  | N4   | Cu1  | 108.8(3)   |

Torsion angles

| A  | B  | C  | D   | Angle/°   | A  | B  | C  | D   | Angle/°  |
|----|----|----|-----|-----------|----|----|----|-----|----------|
| C1 | C2 | N2 | C3  | -161.8(4) | C5 | C6 | N4 | Cu1 | 31.5(4)  |
| C1 | C2 | N2 | Cu1 | -44.7(4)  | C6 | C5 | N3 | C4  | 168.4(4) |
| C2 | C1 | N1 | Cu1 | -42.4(4)  | C6 | C5 | N3 | Cu1 | 47.6(4)  |
| C3 | C4 | N3 | C5  | -89.9(4)  | N1 | C1 | C2 | N2  | 58.3(4)  |
| C3 | C4 | N3 | Cu1 | 29.1(4)   | N2 | C3 | C4 | N3  | -52.7(5) |
| C4 | C3 | N2 | C2  | 167.4(4)  | N3 | C5 | C6 | N4  | -53.3(5) |
| C4 | C3 | N2 | Cu1 | 49.4(4)   |    |    |    |     |          |

FIG. 2

Table 1 Crystal data and structure refinement for 150116_s2_lzh_m

| | |
|---|---|
| Identification code | 150116_s2_lzh_m |
| Empirical formula | $C_6H_{20}Cl_2CuN_4O$ |
| Formula weight | 298.70 |
| Temperature/K | 143.00(10) |
| Crystal system | orthorhombic |
| Space group | $P2_12_12_1$ |
| a/Å | 7.0684(2) |
| b/Å | 10.5124(4) |
| c/Å | 16.5540(5) |
| α/° | 90 |
| β/° | 90 |
| γ/° | 90 |
| Volume/Å$^3$ | 1230.05(7) |
| Z | 4 |
| $\rho_{calc}$ mg/mm$^3$ | 1.613 |
| m/mm$^{-1}$ | 2.188 |
| F(000) | 620.0 |
| Crystal size/mm$^3$ | 0.3 × 0.2 × 0.2 |
| Radiation | MoKα (λ = 0.71073) |
| 2Θ range for data collection | 6.264 to 52.738° |
| Index ranges | −8 ≤ h ≤ 6, −13 ≤ k ≤ 8, −13 ≤ l ≤ 20 |
| Reflections collected | 3978 |
| Independent reflections | 2139 [$R_{int}$ = 0.0266, $R_{sigma}$ = 0.0500] |
| Data/restraints/parameters | 2139/0/135 |
| Goodness-of-fit on F$^2$ | 1.039 |
| Final R indexes [I>=2σ (I)] | $R_1$ = 0.0314, $wR_2$ = 0.0651 |
| Final R indexes [all data] | $R_1$ = 0.0364, $wR_2$ = 0.0679 |
| Largest diff. peak/hole / e Å$^{-3}$ | 0.42/−0.35 |
| Flack parameter | 0.007(13) |

FIG. 3

Table 2 Fractional Atomic Coordinates ($\times 10^4$) and Equivalent Isotropic Displacement Parameters ($Å^2 \times 10^3$) for 150116_s2_lzh_m. $U_{eq}$ is defined as 1/3 of of the trace of the orthogonalised $U_{IJ}$ tensor.

| Atom | x | y | z | U(eq) |
|---|---|---|---|---|
| C1 | −3466(6) | −5730(5) | −7456(3) | 21.1(11) |
| C2 | −3528(6) | −4378(5) | −7122(3) | 19.7(11) |
| C3 | −1517(6) | −3062(5) | −6194(3) | 21.2(11) |
| C4 | 387(7) | −3175(5) | −5773(3) | 21.1(11) |
| C5 | −122(6) | −4630(4) | −4606(3) | 16.4(11) |
| C6 | −180(6) | −6052(4) | −4434(3) | 16.3(11) |
| Cl1 | 1894.2(15) | −6628.5(12) | −6795.6(7) | 20.4(3) |
| Cu1 | −916.8(7) | −5709.6(6) | −6122.9(3) | 14.05(15) |
| N1 | −2985(5) | −6574(4) | −6769(2) | 17.6(9) |
| N2 | −1635(5) | −4137(4) | −6772(2) | 15.4(8) |
| N3 | 584(5) | −4472(4) | −5437(2) | 15.7(9) |
| N4 | −1272(5) | −6685(4) | −5073(2) | 14.3(8) |
| Cl2 | −5193.7(14) | −5164.0(11) | −4787.6(8) | 22.9(3) |
| O1 | −1646(6) | −9247(4) | −7027(3) | 29.4(9) |

FIG. 4A

Table 3 Anisotropic Displacement Parameters ($Å^2 \times 10^3$) for 150116_s2_lzh_m. The Anisotropic displacement factor exponent takes the form:
$-2\pi^2[h^2a*^2U_{11}+2hka*b*U_{12}+\cdots]$

| Atom | $U_{11}$ | $U_{22}$ | $U_{33}$ | $U_{23}$ | $U_{13}$ | $U_{12}$ |
|---|---|---|---|---|---|---|
| C1 | 21(2) | 28(3) | 14(2) | 4(3) | -4.4(19) | 0(2) |
| C2 | 18(2) | 26(3) | 15(2) | 4(3) | -0.1(18) | 2(2) |
| C3 | 32(2) | 14(2) | 19(2) | 3(2) | 0(2) | 8(2) |
| C4 | 30(2) | 13(3) | 19(2) | 3(2) | -2(2) | -2(2) |
| C5 | 19(2) | 17(3) | 13(2) | -4(2) | -0.4(19) | 1(2) |
| C6 | 18(2) | 18(3) | 12(2) | 4(2) | -4.0(19) | 2(2) |
| Cl1 | 20.6(5) | 20.0(7) | 20.7(6) | -1.4(6) | 3.0(5) | 4.1(5) |
| Cu1 | 16.6(3) | 11.9(3) | 13.6(3) | 0.0(3) | -1.3(3) | 0.3(3) |
| N1 | 19.2(19) | 17(2) | 16(2) | 1.1(19) | 0.5(18) | 0.2(18) |
| N2 | 16.5(17) | 16(2) | 13.4(18) | -0.9(19) | -0.1(15) | -0.2(18) |
| N3 | 16.1(17) | 13(2) | 18(2) | 0.9(18) | -1.7(15) | 3.9(18) |
| N4 | 12.5(17) | 13(2) | 18(2) | 0.7(18) | -0.7(15) | -1.2(16) |
| C12 | 15.2(5) | 17.7(6) | 35.6(7) | -0.7(6) | -1.4(5) | 0.5(5) |
| O1 | 40(2) | 24(2) | 24(2) | -6(2) | 1.6(19) | -3(2) |

FIG. 4B

Table 7 Hydrogen Atom Coordinates ($Å \times 10^4$) and Isotropic Displacement Parameters ($Å^2 \times 10^3$) for 150116_s2_1zh_m.

| Atom | x | y | z | U(eq) |
|---|---|---|---|---|
| H1A | -4684 | -5962 | -7682 | 25 |
| H1B | -2516 | -5797 | -7877 | 25 |
| H2A | -3796 | -3774 | -7550 | 24 |
| H2B | -4499 | -4303 | -6711 | 24 |
| H3A | -2537 | -3109 | -5803 | 25 |
| H3B | -1607 | -2257 | -6478 | 25 |
| H4A | 1398 | -3011 | -6156 | 25 |
| H4B | 472 | -2552 | -5343 | 25 |
| H5A | -1376 | -4265 | -4555 | 20 |
| H5B | 713 | -4206 | -4227 | 20 |
| H6A | 1095 | -6392 | -4418 | 20 |
| H6B | -768 | -6205 | -3913 | 20 |
| H1C | -2548 | -7392 | -6966 | 21 |
| H1D | -4090 | -6712 | -6433 | 21 |
| H2 | -716 | -4011 | -7208 | 19 |
| H3 | 1922 | -4716 | -5453 | 19 |
| H4C | -2602 | -6704 | -4929 | 17 |
| H4D | -838 | -7554 | -5139 | 17 |
| H1E | -1310(90) | -9410(70) | -6580(40) | 70(30) |
| H1F | -1840(70) | -9780(50) | -7280(30) | 17(17) |

FIG. 4C

SEQUENCE LISTING

<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1
gtctgcaaca tggaaggtat tg                                    22

<210> SEQ ID NO 2
<211> LENGTH: 20

<212> TYPE: DNA
<213> ORGANISM: Artificial Sequence
<220> FEATURE:
<223> OTHER INFORMATION: Synthetic Construct

<400> SEQUENCE: 2
gcaggtcata ggtggtttct                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
gagcttccta cagcacaaca                                                    20

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct

<400> SEQUENCE: 4
ccaggactta taccgggatt tc                                                 22

<210> SEQ ID NO 5
<211> LENGTH: 22
<212> TYPE: DNA
<213> ORGANISM: Artificial Sequence
<220> FEATURE:
<223> OTHER INFORMATION: Synthetic Construct

<400> SEQUENCE: 5
gggtcacatc acctaacatc ac                                                 22

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
cctttctgct gtcccagatt ac                                                 22

<210> SEQ ID NO 7
<211> LENGTH: 22
<212> TYPE: DNA
<213> ORGANISM: Artificial Sequence
<220> FEATURE:
<223> OTHER INFORMATION: Synthetic Construct

<400> SEQUENCE: 7
ccacgaaact accttcaact cc                                                 22

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct

```
<400> SEQUENCE: 8
gtgatctcct tctgcatcct gt                                          22
```

USE OF TRIENTINE TO DELIVER COPPER TO ISCHEMIC TISSUE

CROSS REFERENCE TO RELATED APPLICATIONS

This application is the U.S. national phase application under 35 U.S.C. § 371 of International Application No. PCT/CN2016/099852, filed Sep. 23, 2016, which claims priority benefit of International Patent Application No. PCT/CN2015/090528 filed Sep. 24, 2015, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 739962000300SEQLIST.txt, date recorded: Mar. 22, 2018, size: 2 KB).

TECHNICAL FIELD OF THE INVENTION

The present invention relates to ischemic tissue repair and regeneration through use of a composition comprising a tetramine, such as trientine.

BACKGROUND OF THE INVENTION

Activation of hypoxia-inducible factors (HIFs) is the initial and primary molecular response of human body to hypoxic or ischemic insult. HIF-1 transcription factor belongs to the HIF family and governs expression of various genes (such as VEGF) that are involved in multiple cellular adaptive responses to hypoxia and/or ischemia, including angiogenesis. HIF-1 comprises two subunits, namely HIF-1$\alpha$ and HIF-1$\beta$. Under hypoxic/ischemic conditions, HIF-1$\alpha$ accumulates in the cell nucleus to form a heterodimer with HIF-1$\beta$, which initiates transcription of downstream genes.

However, under the chronic myocardial ischemic conditions, injured myocardium is commonly characterized by decreased capillary density and depressed angiogenesis. Defense mechanisms, such as those induced by accumulated HIF-1$\alpha$ under acute ischemia insults, do not function under chronic ischemic conditions because of copper mobilization away from myocardium triggered by prolonged ischemia. HIF-1 transcriptional activity has previously been shown to require participation of trace element copper. In patients with chronic ischemic cardiomyopathy, even though HIF-1$\alpha$ levels increase persistently in the ischemic myocardial tissue, expression of HIF-1 regulated genes, such as VEGF, is depressed. Loss of cardiac copper blocks activation of the accumulated HIF-1$\alpha$, and depletion of cardiac copper correlates well with the degree of cardiac dysfunction in such patients. In addition, the decreased cardiac copper content is accompanied by a high blood copper level in patients with myocardial ischemic diseases. It is therefore believed that copper is released from myocardium to blood circulation in a form that is unable to be reused by ischemic myocardium. This dramatically outpouring of myocardial copper to circulation in an unavailable form is believed to be a leading cause for the depression of HIF-1$\alpha$ transcriptional activity accompanied with prolonged myocardial ischemia. Consequently, up-regulation of the HIF-1 controlled genes, an important step for tissue repair and regeneration, may fail to occur in patients with chronic ischemic myocardial diseases, due to the loss of available copper. Therefore, promoting proper tissue distribution of copper may serve as an effective strategy to treat various ischemic diseases and conditions.

Trientine is a well-known copper chelating agent useful in detoxifying copper. Trientine dihydrochloride is a pharmaceutically acceptable salt of trientine that has been widely employed to bind and remove excessive copper in the body to treat Wilson's disease, particularly in patients intolerant to penicillamine. Cooper et al. have described the use of trientine and other copper antagonist compounds to treat various disorders, including diabetes mellitus and complications (e.g. diabetic cardiomyopathy), cardiovascular diseases, neurodegeneration, and mitochondria-related diseases. See, for example, U.S. Pat. Nos. 7,459,446, 7,928,094, international application publication No. WO2003077901 A1, international application publication No. WO2005058294 A1, and international application publication No. WO2007055598 A1.

The disclosures of all publications, patents, and patent applications referred to herein are hereby incorporated herein by reference in their entirety.

BRIEF SUMMARY OF THE INVENTION

The present application provides methods for increasing intracellular copper level or inducing tissue repair of an ischemic tissue in an individual by administering a composition comprising a copper chelating tetramine (such as trientine).

In one aspect of the present application, there is provided a method of increasing intracellular copper level in an ischemic tissue of an individual having ischemic tissue injury, comprising administering to the individual an effective amount of a composition comprising a copper chelating tetramine (such as trientine). Also provided is use of a composition comprising a copper chelating tetramine (such as trientine) in the manufacture of a medicament for increasing intracellular copper level in an ischemic tissue of an individual having ischemic tissue injury, and a composition comprising a copper chelating tetramine (such as trientine) used for increasing intracellular copper level in an ischemic tissue of an individual having ischemic tissue injury.

In one aspect of the present application, there is provided a method of specifically delivering copper into cells of an ischemic tissue in an individual having ischemic tissue injury, comprising administering to the individual an effective amount of a composition comprising a copper chelating tetramine (such as trientine). Also provided is use of a composition comprising a copper chelating tetramine (such as trientine) in the manufacture of a medicament for specifically delivering copper into cells of an ischemic tissue in an individual having ischemic tissue injury, and a composition comprising a copper chelating tetramine (such as trientine) used for specifically delivering copper into cells of an ischemic tissue in an individual having ischemic tissue injury.

In one aspect of the present application, there is provided a method of inducing at least two events of tissue repair in an ischemic tissue of an individual having ischemic tissue injury, comprising administering to the individual an effective amount of a composition comprising a copper chelating tetramine. Also provided is use of a composition comprising a copper chelating tetramine (such as trientine) in the manufacture of a medicament for inducing at least two events of tissue repair in an ischemic tissue of an individual having ischemic tissue injury, and a composition comprising a copper chelating tetramine (such as trientine) used for inducing at least two events of tissue repair in an ischemic tissue of an individual having ischemic tissue injury.

In one aspect of the present application, there is provided a method of inducing migration of stem cells to an ischemic tissue in an individual having ischemic tissue injury, comprising administering to the individual an effective amount of a composition comprising a copper chelating tetramine. Also provided is use of a composition comprising a copper chelating tetramine (such as trientine) in the manufacture of a medicament for inducing migration of stem cells to an ischemic tissue in an individual having ischemic tissue injury, and a composition comprising a copper chelating tetramine (such as trientine) used for inducing migration of stem cells to an ischemic tissue in an individual having ischemic tissue injury.

In one aspect of the present application, there is provided a method of promoting copper-dependent HIF-1 transcriptional activities in an ischemic tissue of an individual having ischemic tissue injury, comprising administering to the individual an effective amount of a composition comprising a copper chelating tetramine. Also provided is use of a composition comprising a copper chelating tetramine (such as trientine) in the manufacture of a medicament for promoting copper-dependent HIF-1 transcriptional activities in an ischemic tissue of an individual having ischemic tissue injury, and a composition comprising a copper chelating tetramine (such as trientine) used for promoting copper-dependent HIF-1 transcriptional activities in an ischemic tissue of an individual having ischemic tissue injury.

In some embodiments according to any one of the methods described above, the individual has a compromised tissue repair system. In some embodiments, the individual does not have a compromised tissue repair system.

In some embodiments according to any one of the methods described above, the ischemic tissue is selected from the group consisting of ischemic heart tissue, ischemic liver tissue, ischemic brain tissue, ischemic lung tissue, ischemic kidney tissue, ischemic skin tissue, ischemic digestive tract tissue, and ischemic limb tissue.

In some embodiments according to any one of the methods described above, wherein the copper chelating tetramine is trientine.

In some embodiments according to any one of the methods described above, the composition further comprises a copper ion. In some embodiments, the copper ion in the composition is complexed with the copper chelating tetramine. In some embodiments, the complex of the copper chelating tetramine and the copper ion is crystalline. In some embodiments, the composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the composition is not complexed with the copper chelating tetramine.

In some embodiments according to any one of the methods described above, the method further comprises administering to the individual an effective amount of a copper ion.

In some embodiments according to any one of the methods described above, the effective amount of the composition is insufficient to lower the extracellular copper level in the individual.

In some embodiments according to any one of the methods described above, the composition is administered orally. In some embodiments, the effective amount of the composition comprises about 80 mg to about 450 mg (including, for example, any of about 80 mg to about 150 mg, about 80 mg to about 200 mg, about 200 mg to about 300 mg, about 80 mg to about 300 mg, about 80 mg, about 100 mg, about 125 mg, about 150 mg, about 200 mg, about 250 mg, about 300 mg, about 350 mg, or about 400 mg) of the copper chelating tetramine per day. In some embodiments, the composition is administered at least two times daily (including, for example, about any one of two times, three times, or four times daily). In some embodiments, the composition is administered for at least about one month (including, for example, about any of 1, 2, 3, 4, 5, 6, 8, 10, 12 or more months).

In some embodiments according to any one of the methods described above, the administration of the composition leads to at least about 0.005 mg/L (including, for example, at least about any of 0.01 mg/L, 0.05 mg/L, 0.1 mg/L, 0.5 mg/L, 1.0 mg/L, 2.0 mg/L, 3.0 mg/L, 4.0 mg/L, or 5 mg/L) of the copper chelating tetramine in the blood. In some embodiments, the administration of the composition leads to at least about 0.005 mg/L of the copper chelating tetramine in the blood for at least about 1 week (including, for example, at least about any of 2 weeks, 1 months, 2 months, 3 months, 4 months, 6 months, 12 months or more).

In some embodiments according to any one of the methods described above, the method further comprises monitoring intracellular copper level in the individual. In some embodiments, the method further comprises adjusting the dosage (including, for example, the effective amount, the administration frequency, and combination thereof) of the composition based on the intracellular copper level in the individual.

In another aspect of the present application, there is provided a pharmaceutical composition comprising a copper chelating tetramine and a copper ion. In some embodiments, the copper chelating tetramine is trientine. In some embodiments, the composition comprises a crystalline complex of trientine and a copper ion, wherein the copper ion is chelated by the four amine groups of trientine to adopt a square-planar geometry, and wherein the crystalline complex further comprises two chloride ions and a water molecule.

In some embodiments according to any one of the pharmaceutical compositions described above, the pharmaceutical composition is formulated as a tablet, a capsule or a pill.

Also provided are compositions, kits and articles of manufacture useful for the methods described herein.

It is understood that aspect and embodiments of the invention described herein including "consisting" and/or "consisting essentially of" aspects and embodiments.

Reference to "about" a value or parameter herein includes (and described) variations that are directed to that value or parameter per se. For example, description referring to "about X" includes description of "X".

The term "about X-Y" used herein has the same meaning as "about X to about Y".

As used herein and in the appended claims, the singular forms "a", or "an", and "the" include plural references unless the context clearly indicated otherwise.

As is apparent to one skilled in the art, and individual assessed, selected for, and/or receiving treatment is an individual in need of such activities.

BRIEF DESCRIPTIONS OF THE DRAWINGS

FIG. 1 depicts a crystal structure of a complex of trientine and a copper ion, which is further associated with two chloride ions and a water molecule. Atoms not labeled are hydrogen atoms.

FIG. 2 lists an exemplary set of bond lengths, bond angles, and torsional angles of the crystal structure of FIG. 1.

FIG. 3 lists crystal and structure refinement data of an exemplary crystal of FIG. 1.

FIGS. 4A-4C list atomic coordinates and anisotropic parameters of atoms in the refined crystal structure of FIG. 3. FIG. 4A lists fractional atomic coordinates and equivalent isotropic displacement parameters of non-hydrogen atoms. FIG. 4B lists anisotropic displacement parameters of non-hydrogen atoms. FIG. 4C lists atomic coordinates and isotropic displacement parameters of hydrogen atoms.

DETAILED DESCRIPTION OF THE INVENTION

Figure 1:
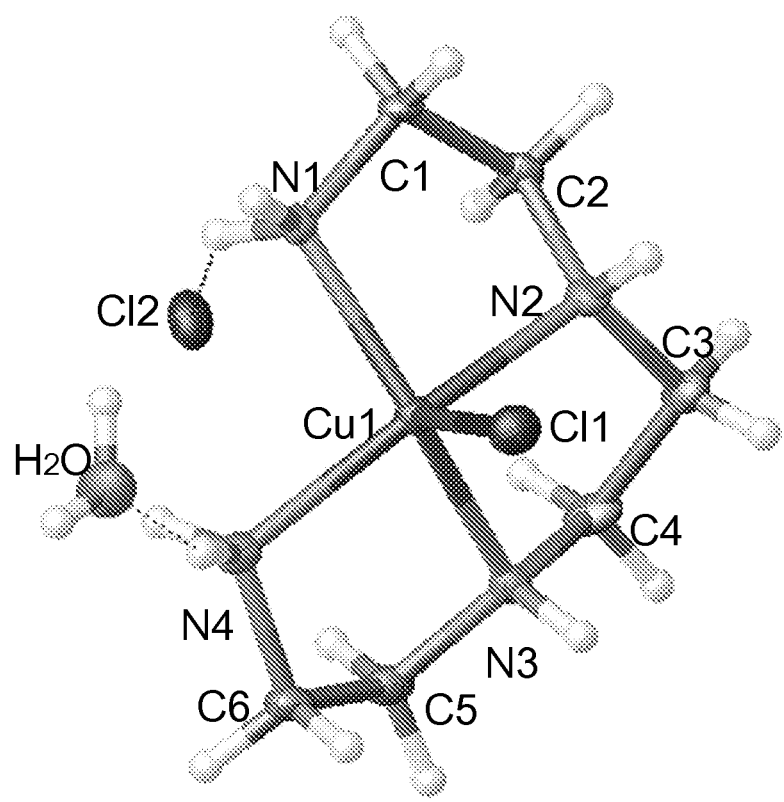

The present application provides methods and compositions for ischemic tissue repair and regeneration by promoting tissue redistribution and reuse of copper. In particular, methods for increasing intracellular copper level in an ischemic tissue in an individual having ischemic tissue injury by administrating a tetramine composition comprising a copper chelating tetramine (such as trientine) and optionally a copper-promoting composition comprising a copper ion are described. The invention described herein is based on the surprising finding that a copper chelating tetramine (such as trientine), previously used to remove copper ions and to reduce copper levels, can promote redistribution of copper between ischemic myocardium and blood circulation, when used according to any of the methods of the present application. Trientine, for example, can specifically bind to an ischemic tissue and serve to load copper into cells at the ischemic tissue. Therefore, trientine and other copper chelating tetramines with similar properties are useful for increasing intracellular copper level in the ischemic myocardium, thereby restoring copper-dependent HIF-1 transcriptional activities, promoting tissue repair, and reversing myocardial ischemic infarction. Thus, the methods and compositions described herein are useful for treating various ischemic diseases and conditions.

Methods of Increasing Intracellular Copper Levels

The present application in one aspect provides a method of increasing intracellular copper level in an ischemic tissue of an individual having ischemic tissue injury, comprising administering to the individual an effective amount of a tetramine composition comprising a copper chelating tetramine (hereinafter also referred to as "tetramine composition"). In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of increasing intracellular copper level in an ischemic tissue of an individual having ischemic tissue injury, comprising administering to the individual an effective amount of a tetramine composition comprising a copper chelating tetramine, and administering to the individual an effective amount of a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper intake, decrease excretion of copper, and/or decrease zinc toxicity. In some embodiments, the copper-promoting composition may change the distribution of copper among cellular organelles. In some embodiments, the tetramine composition and the copper-promoting composition are administered simultaneously. In some embodiments, the tetramine composition and the copper-promoting composition are administered sequentially. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of increasing intracellular copper level in an ischemic tissue of an individual having ischemic tissue injury, comprising administering to the individual an effective amount of a tetramine composition comprising a copper chelating tetramine, and administering to the individual an effective amount of a copper-promoting composition comprising a copper ion. In some embodiments, the copper chelating tetramine is trientine. In some embodiments, the copper-promoting composition is a copper ion. In some embodiments, the tetramine composition and the copper-promoting composition are administered simultaneously. In some embodiments, the tetramine composition and the copper-promoting composition are administered sequentially. In some embodiments, the effective amount of the copper-promoting composition increases the extracellular copper level in the individual. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of increasing intracellular copper level in an ischemic tissue of an individual having ischemic tissue injury, comprising administering to the individual an effective amount of a tetramine composition comprising a copper chelating tetramine, wherein the individual has previously been administered with a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper intake, decrease excretion of copper, and/or decrease zinc toxicity. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of increasing intracellular copper level in an ischemic tissue of an individual having ischemic tissue injury, comprising administering to the individual an effective amount of a tetramine composition comprising a copper chelating tetramine, wherein the individual has previously been administered with an effective amount of a copper-promoting composition comprising a copper ion. In some embodiments, the copper chelating tetramine is trientine. In some embodiments, the copper-promoting composition is a copper ion. In some embodiments, the effective amount of the copper-promoting composition increases the extracellular copper level in the individual. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of delivering copper ion into cells of an ischemic tissue in an individual having ischemic tissue injury, comprising administering to the individual an effective amount of a tetramine composition comprising a copper chelating tetramine. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the method further comprises administering to the individual an effective amount of a copper-promoting composition comprising a copper ion. In some embodiments, the effective amount of the tetramine composition is insufficient to lower the extracellular copper level in the individual. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of delivering copper ion into cells of an ischemic tissue in an individual having ischemic tissue injury, comprising administering to the individual an effective amount of a tetramine composition comprising a copper chelating tetramine, and administering to the individual an effective amount of a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper intake, decrease excretion of copper, and/or decrease zinc toxicity. In some embodiments, the tetramine composition and the copper-promoting composition are administered simultaneously. In some embodiments, the tetramine composition and the copper-promoting composition are administered sequentially. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of delivering copper ion into cells of an ischemic tissue in an individual having ischemic tissue injury, comprising administering to the individual an effective amount of a tetramine composition comprising a copper chelating tetramine, and administering to the individual an effective amount of a copper-promoting composition comprising a copper ion. In some embodiments, the copper chelating tetramine is trientine. In some embodiments, the copper-promoting composition is a copper ion. In some embodiments, the tetramine composition and the copper-promoting composition are administered simultaneously. In some embodiments, the tetramine composition and the copper-promoting composition are administered sequentially. In some embodiments, the effective amount of the copper-promoting composition increases the extracellular copper level in the individual. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of delivering copper ion into cells of an ischemic tissue in an individual having ischemic tissue injury, comprising administering to the individual an effective amount of a tetramine composition comprising a copper chelating tetramine, wherein the individual has previously been administered with a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper intake, decrease excretion of copper, and/or decrease zinc toxicity. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of delivering copper ion into cells of an ischemic tissue in an individual having ischemic tissue injury, comprising administering to the individual an effective amount of a tetramine composition comprising a copper chelating tetramine, wherein the individual has previously been administered with an effective amount of a copper-promoting composition comprising a copper ion. In some embodiments, the copper chelating tetramine is trientine. In some embodiments, the copper-promoting composition is a copper ion. In some embodiments, the effective amount of the copper-promoting composition increases the extracellular copper level in the individual. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of promoting tissue redistribution and reuse of copper in an individual having ischemic tissue injury, comprising administering to the individual an effective amount of a tetramine composition comprising a copper chelating tetramine. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the method further comprises administering to the individual an effective amount of a copper-promoting composition comprising a copper ion. In some embodiments, the effective amount of the tetramine composition is insufficient to lower the extracellular copper level in the individual. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of promoting tissue redistribution and reuse of copper in an individual having ischemic tissue injury, comprising administering to the individual an effective amount of a tetramine composition comprising a copper chelating tetramine, and administering to the individual an effective amount of a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper intake, decrease excretion of copper, and/or decrease zinc toxicity. In some embodiments, the tetramine composition and the copper-promoting composition are administered simultaneously. In some embodiments, the tetramine composition and the copper-promoting composition are administered sequentially. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of promoting tissue redistribution and reuse of copper in an individual having ischemic tissue injury, comprising administering to the individual an effective amount of a tetramine composition comprising a copper chelating tetramine, and administering to the individual an effective amount of a copper-promoting composition comprising a copper ion. In some embodiments, the copper chelating tetramine is trientine. In some embodiments, the copper-promoting composition is a copper ion. In some embodiments, the tetramine composition and the copper-promoting composition are administered simultaneously. In some embodiments, the tetramine composition and the copper-promoting composition are administered sequentially. In some embodiments, the effective amount of the copper-promoting composition increases the extracellular copper level in the individual. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of promoting tissue redistribution and reuse of copper in an individual having ischemic tissue injury, comprising administering to the individual an effective amount of a tetramine composition comprising a copper chelating tetramine, wherein the individual has previously been administered with a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper intake, decrease excretion of copper, and/or decrease zinc toxicity. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of promoting tissue redistribution and reuse of copper in an individual having ischemic tissue injury, comprising administering to the individual an effective amount of a tetramine composition comprising a copper chelating tetramine, wherein the individual has previously been administered with an effective amount of a copper-promoting composition comprising a copper ion. In some embodiments, the copper chelating tetramine is trientine. In some embodiments, the copper-promoting composition is a copper ion. In some embodiments, the effective amount of the copper-promoting composition increases the extracellular copper level in the individual. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, the intracellular copper level is increased by more than about any one of 10%, 20%, 30%, 40%, 50%, 60%, 70%, 80%, 90%, 100%, 200%, 300%, 400%, 500% or more in the ischemic tissue of the individual compared to the intracellular copper level of the ischemic tissue of the individual prior to the treatment. In some embodiments, the copper level (such as total copper level) of the ischemic tissue of the individual is increased by more than about any one of 10%, 20%, 30%, 40%, 50%, 60%, 70%, 80%, 90%, 100%, 200%, 300%, 400%, 500% or more compared to the copper level of the ischemic tissue of the individual prior to the treatment. In some embodiments, the method does not lower the extracellular copper level (such as the copper level in serum) in the individual. In some embodiments, the method does not lower the extracellular copper level (such as the copper level in serum) in the individual by more than about any one of 5%, 10%, 20%, 30%, 40%, 50% or more as compared to the extracellular copper level of the individual prior to the treatment. In some embodiments, the method does not lower the total copper level in the individual. In some embodiments, the method does not lower the total copper level in the individual by more than about any one of 5%, 10%, 20%, 30%, 40%, 50% or more as compared to the total copper level of the individual prior to the treatment. In some embodiments, upon administration of the tetramine composition, the individual has at least about any of 50%, 60%, 70%, 80%, 90%, or more of average total copper level in the serum of healthy individuals.

Any of the methods described above may further comprise monitoring (including measuring and determining) of the copper level of the individual, and adjusting the treatment plan based on the copper level. In some embodiments, the copper level is the extracellular copper level of the ischemic tissue. In some embodiments, the copper level is the serum copper level of the individual. In some embodiments, the copper level is the intracellular copper level of the ischemic tissue. In some embodiments, the copper level is the total copper level, including both $Cu^{1+}$ and $Cu^{2+}$ levels, and/or both intracellular and extracellular copper levels. In some embodiments, the copper level is the $Cu^{2+}$ level. In some embodiments, the copper level is the $Cu^{1+}$ level. In some embodiments, the copper level is the free (i.e. unbound) copper level. In some embodiments, the copper level comprises both free and protein-bound copper level. In some embodiments, the method further comprises monitoring the intracellular copper level in the individual. In some embodiments, the method further comprises adjusting the dosage (including, for example, the effective amount, the administration frequency, and combination thereof) of the tetramine composition based on the intracellular copper level in the individual.

The various copper levels may be monitored either singly or in combination prior to and/or after each administration step, and the corresponding copper levels before and after administration of the tetramine compositions may be compared to determine if the copper level is increased or decreased by the current treatment plan. In some embodiments, the copper level measured after the administration of the tetramine composition is compared with a pre-determined copper level to determine if the copper level needs to be further increased. The pre-determined copper level may be a minimum copper level (such as an intracellular copper level, or an extracellular copper level) that is necessary for promoting copper-dependent HIF transcriptional activities and/or for inducing one or more ischemic tissue repair events. The treatment plan may be adjusted (including, for example, whether to administer a copper-promoting composition, dose, frequency, and duration of the tetramine composition and optionally the copper-promoting composition, etc.) based on any one of the extracellular copper level of the ischemic tissue, the serum copper level of the individual, the intracellular copper level of the ischemic tissue, other copper levels of the individual, and combinations thereof. Furthermore, the extent of repair of the ischemic tissue injury may be monitored to assess the treatment plan. Methods for monitoring repair of the ischemic tissue injury are described in the section of "Methods of inducing tissue repair", which may include, but not limited to, evaluations of pathological, histological or molecular markers associated with the ischemic tissue injury.

In some embodiments according to any one of the methods described herein (including the methods in the section "Methods of" inducing tissue repair), the method further comprises monitoring the intracellular copper level in the individual. In some embodiments, the intracellular copper level of the individual need to be further increased after administration of the tetramine composition, if the intracellular copper level is at least about any of 10%, 20%, 30%, 40%, 50%, 60%, 70%, 80%, 90% or more below the pre-determined intracellular copper level. In some embodiments, wherein the intracellular copper level need to be further increased, the treatment plan of the individual is adjusted by anyone or combination of the following: (a) continue administration of the tetramine composition; (b) administer the tetramine composition at a higher dose; or (c) administer the tetramine composition at a higher dosing frequency. In some embodiments, the method further comprises adjusting the dosage (including, for example, the effective amount, the administration frequency, and combination thereof) of the tetramine composition based on the intracellular copper level in the individual. In some embodiments, the method further comprises monitoring the extracellular copper level in the individual. In some embodiments, the extracellular copper level of the individual need to be increased, if the extracellular copper level of the individual decreases by at least about any of 10%, 20%, 30%, 40%, 50%, 60%, 70%, 80%, 90% or more after the administration of the tetramine composition, or if the extracellular copper level of the individual is at least about any of 10%, 20%, 30%, 40%, 50%, 60%, 70%, 80%, 90% or more below a pre-determined extracellular copper level. In some embodiments, wherein the extracellular copper level of the individual need to be increased, the treatment plan of the individual is further adjusted by anyone or combination of the following: (a) administer a tetramine composition comprising a copper ion, wherein the tetramine composition of the current treatment plan does not comprise a copper ion; (b) administer a copper-promoting composition, wherein the current treatment plan does not comprise administration of a copper-promoting composition; (c) increase the dose of the copper-promoting composition; (d) increase the dose frequency of the copper-promoting composition; (e) administer a different copper-promoting composition; or (f) stop administration of the tetramine composition to the individual.

The copper levels may be determined and/or monitored using any method known in the art. For example, copper level may be quantitatively determined by atomic absorption spectrophotometry, by inductively coupled plasma mass spectrometry (ICPMS), or by protein induced x-ray emission microscopy (PIXE). See for example, Cooper G. J. S. et al. *Diabetes* (2004) 53: 2501-2508; Lu J. et al. Drug Metabolism and Disposition (2007) 35(2): 221-227; and US Patent Publication No. 20100160428A1. For example, the total copper level in an ischemic tissue sample may be measured using a homogenized sample of an ischemic tissue (such as an ischemic tissue homogenized with nitric acid), which includes both intracellular and extracellular contents of the ischemic tissue. The intracellular copper level in an ischemic tissue sample may be measured using cells isolated from an ischemic tissue sample, wherein the cells are further lysed to release intracellular contents prior to the analysis. The extracellular copper level in an individual may be measured using a bodily fluid sample, including, but not limited to, blood serum, plasma, cerebrospinal fluid, lymph, and mucus. In some embodiments, blood serum is used to monitor the extracellular copper level. In some embodiments, liver biopsy is used to determine metabolized copper level in an individual. Electron paramagnetic resonance spectroscopy, for example, may be used to detect the oxidation state ($Cu^{1+}$ vs. $Cu^{2+}$) of copper in the sample, and to provide a percentage of each oxidation state of copper in the sample. The $Cu^{2+}$ level may thus be calculated using the percentage of $Cu^{2+}$ in the sample and the total copper level including both $Cu^{1+}$ and $Cu^{2+}$. Similarly, the $Cu^{1+}$ level may be calculated using the percentage of $Cu^{1+}$ in the sample and the total copper level including both $Cu^{1+}$ and $Cu^{2+}$. In some embodiments, serum ceruloplasmin, and/or serum albumin protein concentration is measured, for example, using antibody-based methods (e.g. Western blot, ELISA, and the like) to monitor the level of copper that is available for uptake and/or reuse by the ischemic tissue. In some embodiments, a cross-section slice of an ischemic tissue sample may be used to measure both intracellular and extracellular copper level using X-ray fluorescence imaging (XRF) methods.

The methods described herein are generally applicable for redistribution of copper (including, for example, increasing intracellular copper level and/or delivering copper to cells) in a variety of ischemic tissues. In some embodiments, the ischemic tissue is selected from the group consisting of ischemic heart tissue, ischemic liver tissue, ischemic brain tissue, ischemic lung tissue, ischemic kidney tissue, ischemic skin tissue, ischemic digestive tract tissue, and ischemic skeletal muscle tissue (such as ischemic limb tissue). In some embodiments, the ischemic tissue is ischemic heart tissue. In some embodiments, the ischemic tissue is ischemic brain tissue.

Methods of Inducing Tissue Repair

The present application in one aspect provides a method of inducing at least one (including, for example at least any of 2, 3, 4, 5, 6, 7, or more) event of tissue repair in an ischemic tissue of an individual having ischemic tissue injury, comprising administering to the individual an effective amount of a tetramine composition comprising a copper chelating tetramine. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing at least one (including, for example at least any of 2, 3, 4, 5, 6, 7, or more) events of tissue repair in an ischemic tissue of an individual having ischemic tissue injury, comprising administering to the individual an effective amount of a tetramine composition comprising a copper chelating tetramine, and an effective amount of a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper uptake, decrease copper excretion and/or decrease zinc toxicity. In some embodiments, the tetramine composition and the copper-promoting composition are administered sequentially. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing at least one (including, for example at least any of 2, 3, 4, 5, 6, 7, or more) events of tissue repair in an ischemic tissue of an individual having ischemic tissue injury, comprising administering to the individual an effective amount of a tetramine composition comprising a copper chelating tetramine, and an effective amount of a copper-promoting composition comprising a copper ion. In some embodiments, the copper chelating tetramine is trientine. In some embodiments, the copper-promoting composition is a copper ion. In some embodiments, the tetramine composition and the copper-promoting composition are administered simultaneously. In some embodiments, the tetramine composition and the copper-promoting composition are administered sequentially. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing at least one (including, for example at least any of 2, 3, 4, 5, 6, 7, or more) events of tissue repair in an ischemic tissue of an individual having ischemic tissue injury, comprising administering to the individual an effective amount of a tetramine composition comprising a copper chelating tetramine, wherein the individual has previously been administered with an effective amount of a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper uptake, decrease copper excretion and/or decrease zinc toxicity. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing at least one (including, for example at least any of 2, 3, 4, 5, 6, 7 or more) events of tissue repair in an ischemic tissue of an individual having ischemic tissue injury, comprising administering to the individual an effective amount of a tetramine composition comprising a copper chelating tetramine, wherein the individual has previously been administered with an effective amount of a copper-promoting composition comprising a copper ion. In some embodiments, the copper chelating tetramine is trientine. In some embodiments, the copper-promoting composition is a copper ion. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments according to any one of the methods of inducing tissue repair as described above, the at least one event (such as at least two events) of tissue repair comprises inducing the migration of stem cells to the ischemic tissue, including but not limited to mesenchymal stem cells (MSCs), bone marrow mesenchymal stem cells (BMSCs), multipotent stem cells, induced pluripotent stem cells (iPS), or various tissue-derived stem cells. In some embodiments, the at least one event (such as at least two events) of tissue repair comprises inducing differentiation of stem cells in the ischemic tissue. In some embodiments, the at least one event (such as at least two events) of tissue repair comprises inducing tissue regeneration in the ischemic tissue. In some embodiments, the at least one event (such as at least two events) of tissue repair comprises reversing damage in the ischemic tissue. In some embodiments, the at least one event (such as at least two events) of tissue repair comprises reconstruction of the microenvironment of neurofibril cells and neurosecretory cells in the ischemic tissue. In some embodiments, the at least one event (such as at least two events) of tissue repair comprises inducing a signaling molecule that triggers tissue regeneration. In some embodiments, the at least one event (such as at least two events) of tissue repair comprises promoting copper-dependent HIF-1 transcriptional activities in the ischemic tissue.

The methods described herein can be used to induce tissue repair events (including, for example, promoting copper-dependent HIF-1 transcriptional activities, and/or inducing migration of stem cells to the ischemic tissue) in various types of ischemic tissues. In some embodiments, the ischemic tissue is selected from the group consisting of ischemic heart tissue, ischemic liver tissue, ischemic brain tissue, ischemic lung tissue, ischemic kidney tissue, ischemic skin tissue, ischemic digestive tract tissue, and ischemic skeletal muscle tissue (such as ischemic limb tissue). In some embodiments, the ischemic tissue is ischemic heart tissue. In some embodiments, the ischemic tissue is ischemic brain tissue.

In some embodiments, there is provided a method of inducing migration (i.e., homing) of stem cells to an ischemic tissue of an individual having ischemic tissue injury, comprising administering to the individual an effective amount of a tetramine composition comprising a copper chelating tetramine. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing migration (i.e., homing) of stem cells to an ischemic tissue of an individual having ischemic tissue injury, comprising administering to the individual an effective amount of a tetramine composition comprising a copper chelating tetramine, and an effective amount of a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper uptake, decrease copper excretion and/or decrease zinc toxicity. In some embodiments, the tetramine composition and the copper-promoting composition are administered sequentially. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing migration (i.e., homing) of stem cells to an ischemic tissue of an individual having ischemic tissue injury, comprising administering to the individual an effective amount of a tetramine composition comprising a copper chelating tetramine, and an effective amount of a copper-promoting composition comprising a copper ion. In some embodiments, the copper chelating tetramine is trientine. In some embodiments, the copper-promoting composition is a copper ion. In some embodiments, the tetramine composition and the copper-promoting composition are administered simultaneously. In some embodiments, the tetramine composition and the copper-promoting composition are administered sequentially. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing migration (i.e., homing) of stem cells to an ischemic tissue of an individual having ischemic tissue injury, comprising administering to the individual an effective amount of a tetramine composition comprising a copper chelating tetramine, wherein the individual has previously been administered with an effective amount of a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper uptake, decrease copper excretion and/or decrease zinc toxicity. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing migration (i.e., homing) of stem cells to an ischemic tissue of an individual having ischemic tissue injury, comprising administering to the individual an effective amount of a tetramine composition comprising a copper chelating tetramine, wherein the individual has previously been administered with an effective amount of a copper-promoting composition comprising a copper ion. In some embodiments, the copper chelating tetramine is trientine. In some embodiments, the copper-promoting composition is a copper ion. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, the stem cell is a mesenchymal stem cell (MSC), a bone marrow mesenchymal stem cell (BMSC), a multipotent stem cell, an induced pluripotent stem cell (iPS), or a tissue-derived stem cell. In some embodiments, the tissue-derived stem cell is an adipose tissue-derived stem cell, a cardiac tissue-derived stem cell, or an umbilical cord tissue-derived stem cell. In other embodiments, the stem cell is an adult stem cell. In particular aspects, the adult stem cell is a hematopoietic stem cell, a mammary stem cell, an intestinal stem cell, a mesenchymal stem cell in the placenta, adipose tissue, lung, bone marrow, blood, Wharton's jelly of the umbilical cord, or teeth (such as the perivascular niche of dental pulp and periodontal ligament), an endothelial stem cell, a neural stem cell, an olfactory adult stem cell, a neural crest stem cell, or a germline stem cell (for example, a stem cell in the testicle).

In some embodiments, the stem cells migrate in vivo from an organ or tissue compartment to a site of ischemic injury in another organ or tissue compartment of an individual having ischemic tissue injury. For example, the MSCs can migrate from the bone marrow (BM), umbilical cord blood (UCB), umbilical cord stroma (Wharton's jelly), placenta, and adipose tissue (AT). In other embodiments, MSCs can be isolated from an organ or tissue compartment, enriched and/or treated in vitro, and then used in vivo for migration to the site of tissue or organ injury.

Assays for measuring cell migration that may be used herein include, but are not limited to, biomarkers, bioluminescence, fluorescence, positron emission tomography (PET)/CT, and magnetic resonance imaging (MRI) in vivo. The in vivo assays can be validated and corroborated with other methods, for example, IHC on tissue sections.

In vivo, noninvasive imaging techniques for assaying stem cell migration include imaging gold-dextran coated particles that are loaded into MSCs, which can be visualized using X-ray, Raman spectroscopy, computed tomography (CT), or ultrasound (US) modalities. In some embodiments, biocompatible nanoparticle constructs, tracers, or superparamagnetic particles are loaded into stem cells such as MSCs with properties to enable cell visualization by X-ray, CT, US, PET, or MRI. In some embodiments, migration of stem cells can be assayed using techniques such as cecal ligation and puncture (CLP). For example, performing CLP on a GFP chimeric mouse allows one to observe the behavior of BMSC in the setting of abdominal sepsis. FACS, flow cytometry and immunohistochemistry can be used to track the migration of BMSC into peripheral blood, lung, liver, the cutaneous wound, and the primary site of ischemic injury. BMSC behavior can be correlated to time of injury as well as to local (using RT-PCR) and systemic levels of cytokines and chemokines. Tracking migration of the stem cells can help elucidate the contribution of BMSC to local and distant organ and tissue repair and regeneration following ischemic tissue injury.

In some embodiments, the migration of stem cells can be monitored using labeled cells administered to an individual. Approaches such as isotopic labelling and dyeing are used to label stem cells. In some embodiments, the labeling approaches include: injecting stem cells of male animals to the female, so the Y chromosome could be the tracker; injecting stem cells of A species to B species, so the specific genes of A species could be the cell tracker; labeling the stem cells with pKH26, BrdU or other dyes, so the stem cells could be tracked by the dyes or specific enzymatic reactions to the tracker.

In some embodiments, isotopic labeling is used to track stem cells in vivo. The stem cells could be tracked by the isotopes that label the cells, but it is worth noticing that the safety issues and radioactive half-life has to be considered. Other in vivo tracking approaches of stem cells include, but are not limited to: cell dyeing by cell dyes such as DID, live imaging of body surface cells by two-photon excited fluorescence microscopy, live imaging of specific body surface cells of transgenic animals by two-photon excited fluorescence microscopy, labeling cells with SPIO and tracking the tracker by MRI, etc. Stem cells could be labeled by multiple fluorescent dyes, and then injected into animals. Shortly prior to the tracking experiment, target organs could be frozen, sliced and observed directly under confocal laser scanning microscopy. This tracking approach does not take too many labeled cells ($10^6$ cell/rabbit), so autologous cells could be tracked in the natural context of the organs and tissues.

Labeling of stem cells can be achieved, for example, by one sole tracker, such as pKH26. pKH26 is a liposoluble dye, and labeling does not allow pKH26 to penetrate the cell membrane. Therefore, pKH26 is suitable for live imaging. The tracking process described herein may involve multiple labeling by 2 or 3 dyes. In some embodiments, nucleus tracker (DAPI, Hoechst) plus membrane tracker are used for multiple labeling. Nucleus tracker affirms the nucleus of the cells, and echoes the membrane tracker pKH26 at the same time. In some embodiments, 2 membrane trackers, e.g. Dio (3) & pKH26, are used for multiple labeling. These trackers label the cells through similar mechanisms, but have different excitation and emission wavelengths, allowing simultaneous confirmation of migration (i.e. homing) of the stem cells (such as BMSCs) from 2 different fluorescent signals. In this tracking method, only the overlapped signals of different wavelengths (such as red and green signals) are considered the homing signals.

Many kinds of animal tissues are auto-fluorescent, and the most common auto-fluorescence in natural tissues is green fluorescence. Heart cells have relatively low fluorescence, but their fluorescence is strong enough to interfere with observations. The cut edge of the slices is always the most strongly fluorescent. To cope with the interference, only green and red overlapped signals could be recognized as the tracking signals. Red fluorescence is more suitable for the statistical analysis with IOD value for its specificity (except for obvious inaccuracy in red fluorescent signals).

In some embodiments, there is provided a method of inducing differentiation of stem cells in the ischemic tissue, comprising administering to the individual an effective amount of a tetramine composition comprising a copper chelating tetramine. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the method further comprises administering to the individual a copper-promoting composition that can increase the extracellular copper level of the individual. In some embodiments, the individual is previously administered with a copper-promoting composition that can increase the extracellular copper level of the individual. In some embodiments, the copper-promoting composition is a copper ion. In some embodiments, the copper-promoting composition does not comprise a copper ion. In some embodiments, the copper-promoting composition may increase copper uptake, decrease copper excretion and/or decrease zinc toxicity. In some embodiments, the tetramine composition is administered orally. In some embodiments, the stem cell is capable of differentiating into a mesenchymal cell type, including osteoblasts, adipocytes, chondrocytes, endothelial cells, epithelial cells, enterocytes, osteocytes, neurocytes, hepatocytes, nephrocytes, myocytes (skeletal muscle and smooth muscle), and cardiomyocytes. In other embodiments, the stem cell is capable of differentiating into cells of nonmesodermal origin including beta cells, hepatocytes, and neurons. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

Assays known in the art can be used to elucidate the process of stem cell differentiation and the phenotypes of differentiated stem cells (such as MSCs, for example BMSC), including, but not limited to, alkaline phosphatase and alizarin red S staining for osteoblasts, oil red 0 staining for adipocytes, and alcian blue staining for chondrogenesis. Differentiation of stem cells such as MSCs into various cell types can also be assayed by gene expression profiling. For example, transcription profiling has identified specific genes implicated in osteogenic differentiation (FHL2, ITGA5, Fgf18), chondrogenesis (FOXO1A), and tenogenesis (Smad8). In some embodiments, MSCs can give rise to high cell numbers by large-scale expansion.

In some embodiments, there is provided a method of inducing tissue regeneration comprising administering to the individual an effective amount of a tetramine composition comprising a copper chelating tetramine. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the method further comprises administering to the individual a copper-promoting composition that can increase the extracellular copper level of the individual. In some embodiments, the individual is previously administered with a copper-promoting composition that can increase the extracellular copper level of the individual. In some embodiments, the copper-promoting composition is a copper ion. In some embodiments, the copper-promoting composition does not comprise a copper ion. In some embodiments, the copper-promoting composition may increase copper uptake, decrease copper excretion and/or decrease zinc toxicity. In some embodiments, the tetramine composition is administered orally. In some embodiments, the method induces cell proliferation in the ischemic tissue. In some embodiments, the method induces angiogenesis in the ischemic tissue. In some embodiments, the method induces blood vessel maturation in the ischemic tissue. In some embodiments, the method results in two or more of the effects descried above. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

Tissue regeneration disclosed herein can be assayed, for example, in an organism in which a portion of a tissue is damaged or removed. A tetramine composition as described herein is then administered to the organism and the rate of tissue regeneration is determined. The rate of tissue regeneration can be compared to the rate observed when an organism is administered a control or is not treated. Other parameters that can be determined during a tissue regeneration assay include, but are not limited to, symptoms or outcomes such as pain or makers of pain, signs or symptoms of inflammation, final degree of regeneration, and quality of regeneration. In some embodiments, a tissue regeneration assay herein comprises assessing one or more organ functional parameters, such as one or more heart functional markers, one or more kidney functional markers, and one or more brain functional markers.

In some embodiments, one or more of the following parameters in the analysis of cardiac regeneration and repair can be used for evaluation of the methods described herein: (1) amount of reconstituted tissue or myocardium mass and coronary vasculature; (2) number and size of restored myocytes and vessels; (3) integration of newly formed myocytes and vessels with the surrounding myocardium; and (4) origin of the regenerated myocardial structures. In one aspect, magnetic resonance imaging (MRI) can be performed to study the scar area, the global left ventricular function, the regional function (wall motion and thickening) and regional ventricular perfusion. In another aspect, MRI is used to detect and/or confirm the presence of new vessels, tissue or cells that improve ventricular function. In yet another aspect, histopathology can be performed to determine the scar area and the identification and quantification of c-kit positive cardiac stem cells. Histopathology also provides data on distribution, size and density of new vessels and cardiomyocytes. Histopathology allows documenting the repair process at the tissue and cellular level. For example, tests are performed to evaluate, within the infarct sections, the microvessel density (vWF-positive vessels/$mm^2$), BrdU positive cells and c-kit positive cells. The quantification of microvessel density using von Willebrand factor (vWF) allows determining the amount of new blood vessels created in the infarct zone. BrdU positive cells represent the proliferation of cells, including cardiac cells. C-kit positive cell tests show the amount of stem cells within the selected infarct sections.

In some embodiments, there is provided a method of reversing damage in an ischemic tissue of an individual having ischemic tissue injury, comprising administering to the individual an effective amount of a tetramine composition comprising a copper chelating tetramine. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the method further comprises administering to the individual a copper-promoting composition that can increase the extracellular copper level of the individual. In some embodiments, the individual is previously administered with a copper-promoting composition that can increase the extracellular copper level of the individual. In some embodiments, the copper-promoting composition is a copper ion. In some embodiments, the copper-promoting composition does not comprise a copper ion. In some embodiments, the copper-promoting composition may increase copper uptake, decrease copper excretion and/or decrease zinc toxicity. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

Reversal of tissue damage can be assayed by any suitable method, for example, detection of cellular markers of normal tissue homeostasis and/or of persistent tissue damage (for example, by immunohistochemistry or measuring DNA and transcript levels), measuring the area of damage or volume of damage, or assessing any clinically relevant indicators. For example, reversal of heart tissue damage of infracted tissue can be measured by quantitation of cell number, such as the number of myocytes, fibroblast, or amount of scarring, or with functional assays for output or structural aspects of heart function including, LVEDP, LVDP, max dp/dt, min dp/dt, LV Weight, Chamber Volume, and Diastolic Wall Stress. In general, a method disclosed herein is said to reverse damage in the ischemic tissue if it results in a significant (e.g., at least 2-fold) change in any such clinical assessment or any combination thereof. In some embodiments, the method reverses fibrosis in the ischemic tissue. Fibrosis is the abnormal accumulation of fibrous tissue that can occur as a part of the wound-healing process in damaged tissue. Such tissue damage may result from physical injury, inflammation, infection, exposure to toxins, and other causes.

Fibrotic tissues accumulate in the heart and blood vessels as a result of hypertension, hypertensive heart disease, atherosclerosis, and myocardial infarction. High blood pressure, or hypertension, can be cause by a variety of factors and often leads to the development of Hypertensive Heart Disease (HHD) with progression to cardiac arrest and myocardial infarction. Similarly, atherosclerosis and other ischemic heart diseases often also result in cardiac arrest. These cardiovascular diseases all exhibit an accumulation of extracellular matrix or fibrotic deposition which results in stiffening of the vasculature and stiffening of the cardiac tissue itself. This deposition of fibrotic material is a response to the damage induced by the hypertensive and/or sclerotic state, but the effects of this response also result in the negative effects of vascular and cardiac stiffening as well as ventricular enlargement. In some instances, the increased cardiac fibrosis in cardiovascular disease disrupts or alters the signals transmitted to cardiomyocytes via the tissue scaffolding of the heart, further leading to disruption of efficient cardiac function and promoting cardiac arrest and myocardial infarction.

In accordance with the present disclosure, expression profiles of genes differentially regulated during tissue damage can be used to assess reversal of tissue damage in a method of treatment disclosed herein. For example, microarray-based analysis of gene expression can be based on the analysis of human cells (such as fibroblasts and cardiomyocytes) subject to selected stimuli resulting in changes in extracellular collagen accumulation and proliferation, the hallmarks of fibrosis. The stimuli can be selected to mimic those in the tissue-specific fibrosis process. Gene expression profiles associated with fibrosis (e.g., liver fibrosis, lung fibrosis, heart tissue fibrosis, diabetic nephropathy, and kidney fibrosis) can then be used to assay fibrosis and reversal of fibrotic damage to the tissue. In other embodiments, gene expression profiles associated with reversal of fibrosis (e.g., under a treatment known to at least partially reverse fibrosis) can be used to assay fibrosis and reversal of fibrotic damage to the tissue.

In some embodiments, there is provided a method of reconstructing the microenvironment of neurofibril cells and neurosecretory cells in an ischemic tissue of an individual having ischemic tissue injury, comprising administering to the individual an effective amount of a tetramine composition comprising a copper chelating tetramine. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the method further comprises administering to the individual a copper-promoting composition that can increase the extracellular copper level of the individual. In some embodiments, the individual is previously administered with a copper-promoting composition that can increase the extracellular copper level of the individual. In some embodiments, the copper-promoting composition is a copper ion. In some embodiments, the copper-promoting composition does not comprise a copper ion. In some embodiments, the copper-promoting composition may increase copper uptake, decrease copper excretion and/or decrease zinc toxicity. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

The microenvironment is an intricate network of both structural and inflammatory cells, cytokines, proteins, and growth factors. In the case of ischemia associated with heart fibrotic diseases or conditions, the heart comprises resident structural cells such as cardiomyocytes, epithelial cells, fibroblasts, and resident cardiomyocyte progenitors and cytokine secreting cells. These cells interact with fibrotic factors during the pathogenesis of fibrosis. In certain aspects, fibroblasts and myofibroblasts play an important role in creating a fibrotic environment, as they secrete excess collagen and matrix materials that lead to irreversible scarring. Cell-to-cell adhesion molecules and extracellular matrix ligands are important factors in the fibrotic microenvironment and promote fibrosis and fibroblast differentiation. In some embodiments, adhesion-mediated signaling is assayed in the tissue microenvironment. For example, cell differentiation and migration occurs in response to mechanic cues from the microenvironment, such as stiffness of the surrounding matrix. In one aspect, elasticity of the tissue or culture matrices of mesenchymal stem cells (MSCs) are assayed and modulated to promote stem cell homing to the ischemically injured tissue, stem cell differentiation at the ischemic injury site, tissue repair, and/or reversal of tissue damage. In one embodiment, soft matrices result in differentiation of MSCs into neuron-like cells, whereas stiff matrices result in differentiation of MSCs into myogenic. In one aspect, the extracellular matrix and its components of the ischemic injury site are assayed to indicate whether the microenvironment promotes stem cell migration to the site, stem cell differentiation at the ischemic injury site, tissue repair, and/or reversal of tissue damage.

In some embodiments, changes in cells in the context of their natural environment are measured to indicate efficacy and/or toxicity of a therapeutic method disclosed herein. In some embodiments, stem cell microenvironment of a donor tissue or organ (such as the bone marrow) and of an ischemic injury site are assayed and/or modulated to promote stem cell migration to the site, stem cell differentiation at the ischemic injury site, tissue repair, and/or reversal of tissue damage. Local tissue microenvironment can be assayed by protein staining (IHC and IF) and RNA staining with either chromogenic or fluorescent ISH. For example, hypoxic microenvironment can be indicated by hypoxic marker staining, endothelial cell marker staining, micro-vessel density analysis, and proximity analysis. Tissue microenvironment can also be studied using organ cultures or organotypic cultures as disclosed in Benbrook, 2006, Drug Discovery Today: Disease Models, 3(2): 143-148.

In some embodiments, there is provided a method of inducing a signaling molecule that triggers tissue regeneration in an ischemic tissue of an individual having ischemic tissue injury, comprising administering to the individual an effective amount of a tetramine composition comprising a copper chelating tetramine. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the method further comprises administering to the individual a copper-promoting composition that can increase the extracellular copper level of the individual. In some embodiments, the individual is previously administered with a copper-promoting composition that can increase the extracellular copper level of the individual. In some embodiments, the copper-promoting composition is a copper ion. In some embodiments, the copper-promoting composition does not comprise a copper ion. In some embodiments, the copper-promoting composition may increase copper uptake, decrease copper excretion and/or decrease zinc toxicity. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

Suitable signaling molecules described herein include, but are not limited to, HIF-1, VEGF, SDF-1, CXCR4, CXCL12 (also termed SDF-1α), MMPs, HGF/c-met, TGF-β1, IL-1β, TNF-α, CCR1, CCR4, CCR7, CCR10, CCR9, CXCR5, CXCR6, CD44, CD54, CD56, CD106, E-cadherin, P-selectin, integrins such as integrin-beta1 and CD49a, b, c, e, f (integrins al, 2, 3, 4, 6), and integrin ligands such as VCAM and ICAM.

SDF-1/CXCR4 axis is one of the most important mechanisms of stem cell homing. SDF-1 (Stromal cell-derived factor 1 or CXCL12), belonging to the CXC-chemokine family, is a small molecular secreted protein. The expression of SDF-1 is regulated by HIF-1 (Hypoxia inducible factor-1). HIF-1 is composed of HIF-1α and HIF-1β/ARNT (aryl hydrocarbon nuclear translocator, ARNT). HIF-1β is stable in the cytoplasm, so the expression and accumulation of HIF-1α determines the activity of HIF-1. Under normoxia, HIF-1α protein is synthesized and degraded rapidly by the ubiquitin-proteasome system. Prolyl hydroxylases (PHDs) hydroxylate HIF-1α and hydroxylated HIF-1α is recognized by the von Hippel-Lindau tumor suppressor protein (pVHL), which constitutes an ubiquitin-protein ligase that targets HIF-1α for protein degradation. Upon ischemic tissue injury, the damaged region is hypoxic, which inhibits the activity of PHDs, enabling HIF-1α accumulation and translocation into the nucleus, where HIF-1α dimerizes with HIF-1β to form HIF-1, combine with other factors and initiates transcription of target genes. Injured tissues express a high level of SDF-1 and release SDF-1 into the circulation, building a concentration gradient from the injured region to the far-end of circulation. The gradient thus attracts CXCR4 expressed stem cells, including BMSCs, to the injured tissues.

When the heart is under chronic hypoxia, blood in the coronary arteries cannot meet the demand of myocardium. Chronic ischemia may induce myocardial fibrosis, decrease density of micro arteries, affect blood pumping, and finally result in ischemic cardiac infarction. Under chronic ischemia, the activity of HIF-1 is limited, resulting in inhibition of the expression of angiogenic factors that are regulated by HIF-1. Blood supply thus could not be restored, and infarction would occur.

Usually, HIF-1 activity in ischemic injured tissues is temporally limited. Both animal experiments and clinical trials have demonstrated that, under cardiac ischemia, HIF-1α in injured tissues accumulates instantly after the injury, but gradually decreases afterward. The activity of HIF-1 drops even faster than the level of HIF-1, resulting in decreased expression of HIF-1 regulated factors, such as VEGF and SDF-1, after the transient increase. Due to the regulation by HIF-1, the expression of SDF-1 peaks at the first or second day after cardiac infarction. SDF-1 expression then decreases gradually, and reduces to the baseline level in about one month. Because SDF-1 is one of the stem cells homing mobilizers, the decrease in SDF-1 level leads to the receding and even disappearing of stem cells homing.

Importantly, the defense mechanisms induced by HIF-1α as activated under acute ischemic conditions function differently from under prolonged ischemic conditions. Under a long-term ischemic condition, HIF protein levels increase in the ischemic myocardium, whereas, genes regulated by HIF (such as VEGF) are suppressed, which leads to diminished revascularization and impaired regeneration. Copper deprivation reduces HIF-1α binding to the HRE sequence of target genes and to P300, a component of HIF-1 transcriptional complex. Moreover, copper is substantially mobilized from myocardium to blood following prolonged ischemia. This mobilization of copper in the coronary flow sensitively follows prolonged, but not short, cardiac ischemia. The loss of myocardium copper correlates with the degree of loss of cardiac functions. Consequently, even under the condition of elevated HIF protein level, up-regulation of HIF controlled genes does not occur due to the loss of myocardium copper. Trace elements such as copper can lead to the activation of HIF-1, including HIF-1α synthesis, stabilization, translocation from cytosol to nucleus, binding to the HRE sequence of target genes, and HIF-1 transcriptional complex formation. Therefore, copper-dependent HIF-1 transcriptional activities, including copper-dependent induction of target genes of HIF-1 or copper-dependent repression of target genes of HIF-1 may play important roles in the repair of ischemic tissues. The methods described herein are useful for inducing one or more signaling molecules, such as HIF-1α and copper-dependent HIF-1 (such as HIF-1α) target genes.

In one aspect of the present application, there is provided a method of promoting copper-dependent HIF-1 transcriptional activities in an ischemic tissue of an individual having ischemic tissue injury, comprising administering to the individual an effective amount of a tetramine composition comprising a copper chelating tetramine. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the tetramine composition is administered orally. In some embodiments, the method induces the expression of at least one copper-dependent HIF-1 target gene in an ischemic tissue of the individual. In some embodiments, the method represses the expression of at least one copper-dependent HIF-1 target gene in an ischemic tissue of the individual. In some embodiments, the at least one copper-dependent HIF-1 target gene is selected from the group consisting of VEGF, GAPDH, GLUT1, PGK1 and BNIP3. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of promoting copper-dependent HIF-1 transcriptional activities in an ischemic tissue of an individual having ischemic tissue injury, comprising administering to the individual an effective amount of a tetramine composition comprising a copper chelating tetramine, and an effective amount of a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper uptake, decrease copper excretion and/or decrease zinc toxicity. In some embodiments, the tetramine composition and the copper-promoting composition are administered sequentially. In some embodiments, the tetramine composition is administered orally. In some embodiments, the method induces the expression of at least one copper-dependent HIF-1 target gene in an ischemic tissue of the individual. In some embodiments, the method represses the expression of at least one copper-dependent HIF-1 target gene in an ischemic tissue of the individual. In some embodiments, the at least one copper-dependent HIF-1 target gene is selected from the group consisting of VEGF, GAPDH, GLUT1, PGK1 and BNIP3. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of promoting copper-dependent HIF-1 transcriptional activities in an ischemic tissue of an individual having ischemic tissue injury, comprising administering to the individual an effective amount of a tetramine composition comprising a copper chelating tetramine, and an effective amount of a copper-promoting composition comprising a copper ion. In some embodiments, the copper chelating tetramine is trientine. In some embodiments, the copper-promoting composition is a copper ion. In some embodiments, the tetramine composition and the copper-promoting composition are administered simultaneously. In some embodiments, the tetramine composition and the copper-promoting composition are administered sequentially. In some embodiments, the tetramine composition is administered orally. In some embodiments, the method induces the expression of at least one copper-dependent HIF-1 target gene in an ischemic tissue of the individual. In some embodiments, the method represses the expression of at least one copper-dependent HIF-1 target gene in an ischemic tissue of the individual. In some embodiments, the at least one copper-dependent HIF-1 target gene is selected from the group consisting of VEGF, GAPDH, GLUT1, PGK1 and BNIP3. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of promoting copper-dependent HIF-1 transcriptional activities in an ischemic tissue of an individual having ischemic tissue injury, comprising administering to the individual an effective amount of a tetramine composition comprising a copper chelating tetramine, wherein the individual has previously been administered with an effective amount of a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper uptake, decrease copper excretion and/or decrease zinc toxicity. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the method induces the expression of at least one copper-dependent HIF-1 target gene in an ischemic tissue of the individual. In some embodiments, the method represses the expression of at least one copper-dependent HIF-1 target gene in an ischemic tissue of the individual. In some embodiments, the at least one copper-dependent HIF-1 target gene is selected from the group consisting of VEGF, GAPDH, GLUT1, PGK1 and BNIP3. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of promoting copper-dependent HIF-1 transcriptional activities in an ischemic tissue of an individual having ischemic tissue injury, comprising administering to the individual an effective amount of a tetramine composition comprising a copper chelating tetramine, wherein the individual has previously been administered with an effective amount of a copper-promoting composition comprising a copper ion. In some embodiments, the copper chelating tetramine is trientine. In some embodiments, the copper-promoting composition is a copper ion. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the method induces the expression of at least one copper-dependent HIF-1 target gene in an ischemic tissue of the individual. In some embodiments, the method represses the expression of at least one copper-dependent HIF-1 target gene in an ischemic tissue of the individual. In some embodiments, the at least one copper-dependent HIF-1 target gene is selected from the group consisting of VEGF, GAPDH, GLUT1, PGK1 and BNIP3. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

HIF-1 target genes have been described in the art. See, for example, Benita Y. et al, (2009) *Nucleic Acids Research,* 37 (14): 4587-4602; Shen C. et al, (2008) *J. Biol. Chem.,* 280: 20580-20588; Elvidge G. P. et al, (2006) *J. Biol. Chem.,* 281: 15215-15266; Manalo D J. et al, (2005) *Blood,* 105: 659-669; the HIF-1 target genes described in the references are incorporated herein by reference. Transcriptional regulation by HIF-1 of a subset of the HIF-1 target genes is depend on copper, and the subset of HIF-1 target genes are herein referred to as copper-dependent HIF-1 target genes. Transcriptional regulation by HIF-1 of some HIF-1 target genes by HIF-1 is independent from copper. See, for example, Zhang Z. et al, (2014) *Metallomics* 6(10): 1889-93. Exemplary copper-dependent HIF-1 target genes include, but are not limited to, vascular endothelial growth factor (VEGF), glyceraldehyde-3-phosphate dehydrogenase (GAPDH), glucose transporter 1 (GLUT1), phosphoglycerate kinase 1 (PGK1) and BCL2/adenovirus E1B 19 kDa protein-interacting protein 3 (BNIP3).

Copper-dependent HIF-1 transcriptional activities contemplated by the present application include induction or repression (i.e. transcriptional regulation) of the expression of copper-dependent HIF-1 target genes in an ischemic tissue. In some embodiments, the copper-dependent HIF-1 transcriptional activity (e.g. fold of induction or repression of a copper-dependent HIF-1 target gene) is reduced by at least about any of 10%, 20%, 30%, 40%, 50%, 60%, 70%, 80%, 90% or more in an ischemic tissue of the individual prior to receiving the treatment, as compared to a control level. In some embodiments, the copper dependent HIF-1 transcriptional activity (e.g. fold of induction or repression of a copper-dependent HIF-1 target gene) in the ischemic tissue of the individual is restored to at least about any of 10%, 20%, 30%, 40%, 50%, 60%, 70%, 80%, 90% or more of the control level, after the individual receives the treatment. A control level of copper-dependent HIF-1 transcriptional activity may be based on the fold of induction or repression of a HIF-1 target gene in a healthy tissue under acute ischemic conditions, or under a comparable level of hypoxic conditions, with respect to normal (e.g. undamaged, or normoxic) conditions. Copper-dependent HIF-1 transcriptional activity may be determined by comparing the expression level (e.g. RNA level and/or protein level) of a copper-dependent HIF-1 target gene in an ischemic tissue to the expression level of the copper-dependent HIF-1 target gene in a healthy tissue. RNA expression levels may be measured using any of the known methods in the art, including, but not limited to, reverse transcription-PCR (RT-PCR), quantitative RT-PCR, microarray, and RNA sequencing methods. Protein expression levels may be measured using any of the known methods in the art, including, but not limited to, antibody-based methods (such as Western blot and ELISA), and quantitative proteomic methods (such as quantitative mass spectrometry).

In some embodiments, there is provided a method of inducing at least two (including, for example at least any of 3, 4, 5, 6, 7, or more) events of tissue repair in an individual having ischemic tissue injury, comprising administering to the individual an effective amount of a tetramine composition comprising a copper chelating tetramine, wherein the at least two events of tissue repair are selected from the group consisting of: inducing the migration of stem cells such as bone marrow mesenchymal stem cells to the ischemic tissue, inducing differentiation of stem cells in the ischemic tissue, inducing tissue regeneration in the ischemic tissue, inducing a signaling molecule that triggers tissue regeneration, reversing damage in the ischemic tissue, reconstructing the microenvironment of neurofibril cells and neurosecretory cells in the ischemic tissue, and promoting copper-dependent HIF-1 transcriptional activities. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the method further comprises administering to the individual a copper-promoting composition that can increase the extracellular copper level of the individual. In some embodiments, the individual is previously administered with a copper-promoting composition that can increase the extracellular copper level of the individual. In some embodiments, the copper-promoting composition is a copper ion. In some embodiments, the copper-promoting composition does not comprise a copper ion. In some embodiments, the copper-promoting composition may increase copper uptake, decrease copper excretion and/or decrease zinc toxicity. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing the migration of stem cells (such as MSC, for example BMSC) to the ischemic tissue and inducing differentiation of stem cells in the ischemic tissue, comprising administering to the individual an effective amount of a tetramine composition comprising a copper chelating tetramine. In some embodiments, there is provided a method of inducing the migration of stem cells (such as MSC, for example BMSC) to the ischemic tissue and inducing tissue regeneration in the ischemic tissue, comprising administering to the individual an effective amount of a tetramine composition comprising a copper chelating tetramine. In some embodiments, there is provided a method of inducing the migration of stem cells (such as MSC, for example BMSC) to the ischemic tissue, inducing differentiation of stem cells in the ischemic tissue, and inducing tissue regeneration in the ischemic tissue, comprising administering to the individual an effective amount of a tetramine composition comprising a copper chelating tetramine. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the method further comprises administering to the individual a copper-promoting composition that can increase the extracellular copper level of the individual. In some embodiments, the individual is previously administered with a copper-promoting composition that can increase the extracellular copper level of the individual. In some embodiments, the copper-promoting composition is a copper ion. In some embodiments, the copper-promoting composition does not comprise a copper ion. In some embodiments, the copper-promoting composition may increase copper uptake, decrease copper excretion and/or decrease zinc toxicity. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing ischemic tissue repair (or improving the function of the ischemic tissue) in an individual having ischemic tissue injury, comprising administering to the individual an effective amount of a tetramine composition comprising a copper chelating tetramine. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the tetramine composition is administered orally. In some embodiments, the ischemic tissue is selected from the group consisting of ischemic heart tissue, ischemic liver tissue, ischemic brain tissue, ischemic lung tissue, ischemic kidney tissue, ischemic skin tissue, ischemic digestive tract tissue, and ischemic skeletal muscle tissue (such as ischemic limb tissue). In some embodiments, the ischemic tissue is ischemic heart tissue. In some embodiments, the ischemic tissue is ischemic brain tissue. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing ischemic tissue repair (or improving the function of the ischemic tissue) in an individual having ischemic tissue injury, comprising administering to the individual an effective amount of a tetramine composition comprising a copper chelating tetramine, and an effective amount of a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper uptake, decrease copper excretion and/or decrease zinc toxicity. In some embodiments, the tetramine composition and the copper-promoting composition are administered sequentially. In some embodiments, the tetramine composition is administered orally. In some embodiments, the ischemic tissue is selected from the group consisting of ischemic heart tissue, ischemic liver tissue, ischemic brain tissue, ischemic lung tissue, ischemic kidney tissue, ischemic skin tissue, ischemic digestive tract tissue, and ischemic skeletal muscle tissue (such as ischemic limb tissue). In some embodiments, the ischemic tissue is ischemic heart tissue. In some embodiments, the ischemic tissue is ischemic brain tissue. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing ischemic tissue repair (or improving the function of the ischemic tissue) in an individual having ischemic tissue injury, comprising administering to the individual an effective amount of a tetramine composition comprising a copper chelating tetramine, and an effective amount of a copper-promoting composition comprising a copper ion. In some embodiments, the copper chelating tetramine is trientine. In some embodiments, the copper-promoting composition is a copper ion. In some embodiments, the tetramine composition and the copper-promoting composition are administered simultaneously. In some embodiments, the tetramine composition and the copper-promoting composition are administered sequentially. In some embodiments, the tetramine composition is administered orally. In some embodiments, the ischemic tissue is selected from the group consisting of ischemic heart tissue, ischemic liver tissue, ischemic brain tissue, ischemic lung tissue, ischemic kidney tissue, ischemic skin tissue, ischemic digestive tract tissue, and ischemic skeletal muscle tissue (such as ischemic limb tissue). In some embodiments, the ischemic tissue is ischemic heart tissue. In some embodiments, the ischemic tissue is ischemic brain tissue. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing ischemic tissue repair (or improving the function of the ischemic tissue) in an individual having ischemic tissue injury, comprising administering to the individual an effective amount of a tetramine composition comprising a copper chelating tetramine, wherein the individual has previously been administered with an effective amount of a copper-promoting composition that can increase the extracellular copper level of the individual. In some embodiments, the copper chelating tetramine is trientine. In some embodiments, the copper-promoting composition does not comprise a copper ion. In some embodiments, the copper-promoting composition may increase copper uptake, decrease copper excretion and/or decrease zinc toxicity. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the ischemic tissue is selected from the group consisting of ischemic heart tissue, ischemic liver tissue, ischemic brain tissue, ischemic lung tissue, ischemic kidney tissue, ischemic skin tissue, ischemic digestive tract tissue, and ischemic skeletal muscle tissue (such as ischemic limb tissue). In some embodiments, the ischemic tissue is ischemic heart tissue. In some embodiments, the ischemic tissue is ischemic brain tissue. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of inducing ischemic tissue repair (or improving the function of the ischemic tissue) in an individual having ischemic tissue injury, comprising administering to the individual an effective amount of a tetramine composition comprising a copper chelating tetramine, wherein the individual has previously been administered with an effective amount of a copper-promoting composition comprising a copper ion. In some embodiments, the copper chelating tetramine is trientine. In some embodiments, the copper-promoting composition is a copper ion. In some embodiments, the individual has been administered with the copper-promoting composition about any one of 1 day, 2 days, 3 days, 4 days, 5 days, 6 days, 1 week, 2 weeks, 3 weeks, 4 weeks, or more prior to administration of the tetramine composition. In some embodiments, the tetramine composition is administered orally. In some embodiments, the ischemic tissue is selected from the group consisting of ischemic heart tissue, ischemic liver tissue, ischemic brain tissue, ischemic lung tissue, ischemic kidney tissue, ischemic skin tissue, ischemic digestive tract tissue, and ischemic skeletal muscle tissue (such as ischemic limb tissue). In some embodiments, the ischemic tissue is ischemic heart tissue. In some embodiments, the ischemic tissue is ischemic brain tissue. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

Also provided are methods of treating a disease or a condition associated with ischemic tissue injury using any of the methods described herein.

In some embodiments, there is provided a method of treating ischemic heart failure in an individual, comprising administering to the individual an effective amount of a tetramine composition comprising a copper chelating tetramine (such as trientine). In some embodiments, the effective amount of the tetramine composition is insufficient to lower the extracellular copper level in the individual. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily. In some embodiments, the tetramine composition is administered for at least about 1 month (such as at least about 3 months or at least about 6 months). In some embodiments, the individual has a left ventricular ejection function (LVEF) of no more than about 35% at baseline. In some embodiments, the individual has class II or class III heart failure (based on New York Heart Association or NYHA Functional classification).

Heart failure of any class or stage that has an ischemic origin (i.e., ischemic heart failure) may be treated with the methods described herein. In some embodiments, the individual has NYHA Class I heart failure of ischemic origin. In some embodiments, the individual has NYHA Class II ischemic heart failure of ischemic origin. In some embodiments, the individual has NYHA Class III ischemic heart failure of ischemic origin. In some embodiments, the individual has NYHA Class IV ischemic heart failure of ischemic origin. In some embodiments, the individual has NYHA Class A ischemic heart failure of ischemic origin. In some embodiments, the individual has NYHA Class B ischemic heart failure of ischemic origin. In some embodiments, the individual has NYHA Class C ischemic heart failure of ischemic origin. In some embodiments, the individual has NYHA Class D ischemic heart failure of ischemic origin. In some embodiments, the individual has one or more symptoms of ischemic heart failure, such as fatigue, palpitation, dyspnea, or limitation of physical activity. In some embodiments, the individual has one or more symptoms of cardiovascular disease. In some embodiments, the individual has been hospitalized for at least about any one of 1, 2, 3, 4, 5, 6, 7, 10, 15, 20, 25, 30, or more days.

The efficacy of any one of the methods described herein may be additionally determined by assessing the extent of repair of the ischemic tissue. Tissue repair can be assessed, for example, by the area of damage or volume of damage. The repair of damaged tissue in a patient can be assessed using any clinically relevant standard. For example, repair of infracted tissue can be measured by quantitation of cell number, such as the number of myocytes, fibroblast, or amount of scarring, or with functional assays for output or structural aspects of heart function including, LVEDP, LVDP, max dp/dt, min dp/dt, LV Weight, Chamber Volume, and Diastolic Wall Stress. In general, a method disclosed herein is said to repair damaged tissue if it results in a significant (e.g., at least 2-fold) change in any such clinical assessment or any combination thereof.

Any appropriate method(s) can be performed to assay tissue repair. For example, methods can be performed to assess tissue healing, to assess functionality of repaired tissue, and to assess cellular growth in the tissue. To determine the extent of tissue healing, histology and cell staining can be performed to detect seeded cell propagation and/or improved histological appearance. In some cases, tissue portions can be collected and treated with a fixative such as, for example, neutral buffered formalin. Such tissue portions can be dehydrated, embedded in paraffin, and sectioned with a microtome for histological analysis. Sections can be stained with hematoxylin and eosin (H&E) and then mounted on glass slides for microscopic evaluation of morphology and cellularity. In some cases, physiological tests can be performed to assess tissue movement and functionality following treatment according to the methods and materials provided herein. For example, in vitro mechanical assays can be performed to measure the work of flexion (WOF) or flexion angle of a repaired tendon tissue or of a repaired joint. In vivo assays can include functional evaluation of the organs, symptom assessment, or imaging techniques.

In some embodiments, tissue and/or organ function before, during, or after administering a therapeutic method disclosed herein can be assessed by any one or more of the following methods: biochemical analysis of at least one biomarker indicative of improved tissue function by methods such as flow cytometry, immunofluorescence, ELISA, phosphor-labeling, hybridization, nucleic acid amplification, or Western blot; cellular function assays, such as cell apoptosis assays, necrosis assays, and cell viability assays, including Annexin V staining by immunofluorescence or flow cytometry, detection of caspase activity, hypoxia assays, TUNEL assay, cell DNA laddering, number of rod-shaped cells in response to $H_2O_2$, qPCR assessment of gene expression, and measuring necrotic area by H&E staining; scar formation assays, including measuring number of fibroblastic cells in a damaged or infarcted area, measuring collagen deposition and level of other matrix proteins associated with scar formation; migration of stem cells or progenitor cells into the damaged area; and any other clinically relevant organ function tests.

In some embodiments, cardiac function can be assessed by any one or more of the following parameters: myocyte mechanics and cell fusion, for example, frequency of distribution of myocyte size, peak shortening, velocity of shortening and relengthening, and assessment of cell fusion (number of X chromosomes); output or structural aspects of heart function including, LVEDP, LVDP, +dp/dT, LV Weight, Chamber Volume, Diastolic Wall Stress, and comparison of MI-treated and MI-untreated subjects; myocardial regeneration, such as composition of regenerated myocardium, assessment of BrdU positive cells in infarcted area in treated versus untreated subjects, and myosin positive cells in the infarcted area in treated versus untreated subjects; cardiac structural, such as infarct size, amount of fibrosis, and cardiomyocyte hypertrophy. In certain embodiments, a method disclosed herein further comprises measuring one or more indicia of cardiac function, wherein said indicia of cardiac function are chest cardiac output (CO), cardiac index (CI), pulmonary artery wedge pressure (PAWP), cardiac index (CI), % fractional shortening (% FS), ejection fraction (EF), left ventricular ejection fraction (LVEF); left ventricular end diastolic diameter (LVEDD), left ventricular end systolic diameter (LVESD), contractility (dP/dt), a decrease in atrial or ventricular functioning, an increase in pumping efficiency, a decrease in the rate of loss of pumping efficiency, a decrease in loss of hemodynamic functioning, and decrease in complications associated with cardiomyopathy, as compared to a control.

In some embodiments, brain function before, during, or after administering a therapeutic method disclosed herein can be assessed by a neurological testing, or electrophysiologically, for example by a decreased signal to noise ratio, or biochemically, for example, by analysis of at least one biomarker indicative of organ function, tissue function, and/or cellular function of the central or peripheral nervous system. Exemplary electrophysiological techniques include electroencephalography (EEG), electrocardiography (EKG), electromyography (EMG), event-related potentials (ERPs), evoked potentials (EPs), magnetoencephalography (MEG), and nerve conduction study (NCS). In other embodiments, brain function can be assessed by any one or more of the following methods or parameters: general intellectual function, such as Wechsler Abbreviated Scale of Intelligence and Wechsler Adult Intelligent Scale-III; basic attention, such as Digit Span, Spatial span subtests from the Wechsler Memory Scale-III; complex attention (working memory), such as Digit Span, Letter Number Sequencing and Arithmetic subtests from the Wechsler Adult Intelligence Scale-III; executive functions, such as Wisconsin Card Sorting Test, Trail Making Test B, Stroop Test, Tower of London Test, Gambling Test, Frontal System Behavior Scale, and Iowa Scales of Frontal Lobe Function; memory (visual and verbal), such as Wechsler Memory Scales-III, Rey Auditory, Verbal Learning Test, California Verbal, Learning Test-II, Brief Visual Memory Test Revised; affect regulation, such as Minnesota Multiphasic Personality Inventory-2, Affective Stroop Test, Frontal System Behavior Scale, and Iowa Scales of Frontal Lobe Function; interpretation of emotion stimuli, such as DANVA (Diagnostic Analysis of Nonverbal Behavior); processing speed, such as Processing Speed index (Symbol Search, Coding) from the Wechsler Adult Intelligent Scale-III, Trail Making Test, and Symbol Digit Modalities Test; language, such as Boston Naming Test; Controlled Oral Word Association Test; Semantic Word Fluency Test; and Multilingual Aphasia Examination; visuo-constructional tests, such as Rey-Osterrieth Complex Figure Test, Block Design, and Object Assembly subtests from the Wechsler Adult Intelligence Scale-III; and visuo-spatial tests, such as Matrix Reasoning from the WAIS-III, and Judgment of Line Orientation Test.

In some embodiments, skeletal muscle health before, during, or after administering a therapeutic method disclosed herein is tested. In some embodiments, skeletal muscle health includes muscle soreness, muscle damage, metabolic changes to exercise, and cytoskeletal re-organization. The skeletal muscle function can be muscle strength, muscle endurance, training adaption, a normal state of the muscle that will allow movement of the joints, or standard physiological metabolism and function of skeletal muscle in a healthy mammal. Any functional variable of the skeletal muscle can be measured, including muscle strength (maximal force generated in a specific movement), muscle endurance (the maximal number of contractions which can be performed at a set frequency and force), and muscle power (force/time, the maximal effect generated by the muscle). While not exhaustive, typical muscle-specific functions include myoblast differentiation, myoblast determination, muscle development, muscle contraction, sarcomeric changes, myoblast fusion, somatic muscle development, and myogenesis.

In some embodiments, skeletal muscle fibrosis of a patient is assessed. A number of methods are available to determine the state of skeletal muscle fibrosis, including obtaining a biopsy of muscle tissue from the patient, and evaluating the biopsy with histochemical or immuno-histochemical stains sensitive to detect the existence of fibrotic tissue. Examples of histochemical stains include, for example, hematoxylin and eosin (H&E), trichrome and ATPase (e.g., at pH 4.3, 4.65 and 10.4). Representative antibodies which can be used to label muscle fibers for immuno-histochemical staining include, for example, myosin, type IV collagen, laminin, fibronectin and dystrophin. Alternatively, a functional method of determining the extent to which fibrosis pervades a patient's skeletal muscle can be employed. The functional method involves subjecting the patient to one or more of a battery of tests and physical measurements. Such tests and measurements typically include neurological strength tests, muscle strength, balance, gait, posture, sensory coordination evaluations, and pulmonary function tests, e.g., vital capacity and forced expiratory capacity, all of which can be carried out by methods known in the art. In some embodiments, tissue repair can be assessed based on the expression level(s) of one or more signaling molecules described herein. Suitable biomarkers as indicators of tissue repair include, but are not limited to, a DNA-damage biomarker, an inflammatory-response biomarker, a tissue-damage biomarker, a tissue-damage repair biomarker, or a hematology-surrogate marker, such as p53, p21, GADD45a, ATM, phosphorylated H2AX histone, IL-6, CRP, SAA, IL-1, IL-5, IL-10, KC/GRO, IFN, IL-2, IL-4, TNF-alpha, IL-12, IL-3, IL-7, IL-6, salivary beta-amylase, citrulinated proteins, S100B, SP-D, BPI, TSP, CA15-3, CDBB, CKMB, CKMM, FABP2, GFAP, NSE, CDS, CD-16b, CD20, CD177, CD26, CD27, CD40, CD45, Flt-3L, G-CSF, KFG, EPO, TPO, GM-CSF, or SDF-1α.

Copper (including copper ion) is a regulator of one or more factors (for example, transcriptional factors) involved in repair of tissue damage and/or in tissue regeneration, and consequently, tissue repair can be assessed by assessing any one or more of these factors. Copper regulated factors include, but are not limited to: Cu homeostasis proteins, such as Ctr 1, Ctr 3, DMT1, Atox 1, ATP7A/7B, Cox 17, CCS, Sco 1/2, Cox 11, Glutamatergic N-methyl D-aspartate receptors (NMDAR), Amyloid precursor protein (APP), Copper metabolism gene MURR1 domain (COMMD1), X-linked inhibitor of apoptosis (XIAP), homocysteine (Hcy), subunit II of cytochrome c oxidase (COX II), subunit I of cytochrome c oxidase (COX I), FGF-1, VEGF, angiopoietin (such as ANG1 or ANG2), fibronectin, collagenase, MMPs-TIMPs, elastin, PDGF, and eNOS; intracellular Cu binding proteins, such as Cytochrome C oxidase (CCO), Superoxide dismutase (SOD), Metallothionein (MT), Glutathione (GSH), Dopamine-β-monooxygenase (DBH), Peptidylglycine-α-amidating monooxygenase (PAM), Tyrosinase, Phenylalanine hydroxylase, Diamine oxidase, Hephaestin, and Cartilage matrix glycoprotein; extracellular Cu binding proteins, such as Ceruloplasmin (CP), Lysyl oxidase (LOX), Albumin (ALB), Transcuprein, Amine oxidase, Blood clotting factors V and VIII, Ferroxidase II, Extracellular superoxide dismutase, and Extracellular metallothionein. Copper regulated factors are disclosed in Zheng et al., Role of copper in regression of cardiac hypertrophy, Pharmacol. Ther. doi:10.1016/j.pharmthera.2014.11.014 (2014), which is incorporated herein by reference. In some embodiments, the copper or copper ion regulates the transcriptional activity of one or more of HIF-1, SP1, MT, Atox 1, CCS, and COMMD1, and the signaling networks regulated by these transcriptional factors.

In some embodiments, the level and/or activity of one or more factors regulated by copper disclosed herein are analyzed in an individual following treatment with a therapeutic or preventive composition disclosed herein. In some embodiments, the level and/or activity of one or more of HIF-1, SP1, MT, Atox 1, CCS, and COMMD1 are determined, and then correlated with a response of the individual to the therapeutic or preventive composition. In some embodiments, the response is detected by measuring cellular markers of normal tissue homeostasis and/or of persistent ischemic tissue damage (for example, by immunohistochemistry or measuring DNA and transcript levels), measuring the area of damage or volume of damage, or assessing any clinically relevant indicators. Thus, in certain aspects, the level and/or activity of one or more copper regulated factors (such as HIF-1, SP1, MT, Atox 1, CCS, and COMMD1) can be used as an end-point biomarker of an individual's response to a therapeutic or preventive regimen disclosed herein.

In some embodiments, one or more factors regulated by copper disclosed herein can be used in a prognostic test to analyze and predict a response to a tetramine composition or treatment or preventive method disclosed herein. For example, the level and/or activity of one or more of HIF-1, SP1, MT, Atox 1, CCS, and COMMD1 can indicate a likelihood that an individual will respond positively to a treatment or preventive composition disclosed herein, the treatment or preventive composition may be administered to the individual. Conversely, if the level and/or activity of one or more of HIF-1, SP1, MT, Atox 1, CCS, and COMMD1 indicate that an individual is likely not to respond or to respond negatively to the treatment or preventive composition, an alternative course of treatment may be prescribed. A negative response may be defined as either the absence of an efficacious response or the presence of toxic side effects. The response to a therapeutic or preventive treatment can be predicted in a background study in which subjects in any of the following populations are genotyped: a population that responds favorably to a treatment regimen, a population that does not respond significantly to a treatment regimen, and a population that responds adversely to a treatment regimen (e.g. exhibits one or more side effects). These populations are provided as examples and other populations and subpopulations may be analyzed. Based upon the results of these analyses, an individual is genotyped to predict whether he or she will respond favorably to a treatment regimen, not respond significantly to a treatment regimen, or respond adversely to a treatment regimen. Thus, in some embodiments, the level and/or activity of one or more of HIF-1, SP1, MT, Atox 1, CCS, and COMMD1 can be used as response indicators of an individual to a therapeutic or preventive regimen disclosed herein. The response indicators can be assessed before, during, and/or after administering the therapeutic or preventive regimen. For example, one or more response indicators can be assessed during the intervals between doses of a continuous administration, to evaluate whether the individual is likely to benefit from continued treatment or an alternative treatment is needed.

The prognostic tests described above are applicable to clinical trials. One or more response indicators (such as HIF-1, SP1, MT, Atox 1, CCS, and COMMD1) may be identified using the methods described herein. Thereafter, potential participants in clinical trials of a tetramine composition comprising a copper chelating tetramine and optionally a copper-promoting composition comprising a copper ion may be screened to identify those individuals most likely to respond favorably to the tetramine composition and exclude those likely to experience side effects. In that way, the effectiveness of treatment may be measured in individuals who respond positively to the tetramine composition, without lowering the measurement as a result of the inclusion of individuals who are unlikely to respond positively in the study and without risking undesirable safety problems.

In some embodiments, there is provided a method of inducing tissue repair in an individual having ischemic tissue injury without increasing the expression of VEGF at the site of injection, comprising administering to the individual an effective amount of a tetramine composition comprising a copper chelating tetramine. In some embodiments, there is provided a method of inducing blood vessel growth towards the site of ischemic injury in an individual, comprising administering to the individual an effective amount of a tetramine composition comprising a copper chelating tetramine. In some embodiments, there is provided a method of inducing blood vessel growth towards the site of ischemic injury in an individual without increasing the expression of VEGF at the site of the injection, comprising administering to the individual an effective amount of a tetramine composition comprising a copper chelating tetramine. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the method further comprises administering to the individual a copper-promoting composition that can increase the extracellular copper level of the individual. In some embodiments, the individual is previously administered with a copper-promoting composition that can increase the extracellular copper level of the individual. In some embodiments, the copper-promoting composition is a copper ion. In some embodiments, the copper-promoting composition does not comprise a copper ion. In some embodiments, the copper-promoting composition may increase copper uptake, decrease copper excretion and/or decrease zinc toxicity. In some embodiments, the tetramine composition is administered orally. In some embodiments, the ischemic tissue is selected from the group consisting of ischemic heart tissue, ischemic liver tissue, ischemic brain tissue, ischemic lung tissue, ischemic kidney tissue, ischemic skin tissue, ischemic digestive tract tissue, and ischemic skeletal muscle tissue (such as ischemic limb tissue). In some embodiments, the ischemic tissue is ischemic heart tissue. In some embodiments, the ischemic tissue is ischemic brain tissue. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

The formation and growth of blood vessels within a tissue may occur by angiogenesis and/or vasculogenesis. In some embodiments, blood vessels include capillary-like structures that are fully functional to support the transport of blood. In some embodiments, angiogenesis includes a process involving the growth of new blood vessels from pre-existing vessels, sprouting angiogenesis, the formation of new blood vessel by sprouting off existing ones, or splitting angiogenesis (intussusception), the formation of new blood vessel by splitting off existing ones. In some embodiments, vasculogenesis includes a process involving the de novo production of new blood-vessels by proliferating endothelial stem cells, such as the formation of new blood vessels when there were no pre-existing ones.

In some embodiments, blood vessel formation and growth requires signals from growth factors and other proteins that directly control the process, such as angiopoietins (like Ang-1 and Ang-2), ephrin (Eph), vascular endothelial growth factors (like VEGF-A and VEGF-C), platelet derived growth factor (PDGF), fibroblast growth factors (like FGF-1 and FGF-2), tumor necrosis factor-α (TNF-α), interleukin (IL), monocyte chemotactic protein-1 (MCP-1) (also known as CCL-2), transforming growth factor-α (TGF-α), transforming growth factor-βs (like TGF-β1, TGF-β2, TGF-β3, and TGF-β4), endostatin, vasohibin, chemokines, thrombospondin, angiostatin, vascular cell adhesion molecules (like VCAM-1), matrix metalloproteinases (like MMP-2 and MPP-9), integrins, cadherins, plasminogen activators, and plasminogen activator inhibitors.

In some embodiments, blood vessel growth is assayed by measuring endothelial cell proliferation, which is needed for developing capillaries in an intact animal. In some embodiments, the action of administration of a tetramine composition comprising a copper chelating tetramine on endothelial proliferation can be assessed by direct cell counts, DNA synthesis, and/or metabolic activity. For example, endothelial cells can be isolated from the site of ischemic injury and assayed for their proliferation rate after treatment with a tetramine composition comprising a copper chelating tetramine. In other embodiments, the proliferation of endothelial cells at the site of ischemic injury can be monitored by labeling the cells and measuring cell counts, DNA synthesis, and/or metabolic activity in situ. In other embodiments, labeled endothelial cells can be administered to an individual, and the proliferation of labeled endothelial cells at the site of ischemic injury can be monitored in situ. In some embodiments, endothelial cells are labeled with a radioisotope, a fluorescent moiety, or a marker that can be specifically detected, for example, by an antibody. In specific embodiments, the cells are labeled with [$^3$H]thymidine or bromodeoxyuridine (BrdU).

In some embodiments, blood vessel growth is assayed by measuring migration of endothelial cells, which degrade the basement membrane and migrate along chemical gradients established by proangiogenic growth factors, for example, during sprouting angiogenesis. In certain embodiments, endothelial cells at the site of ischemic injury are labeled and cell migration is monitored in vivo. In other aspects, labeled endothelial cells are administered to a subject, and their migration toward the site of ischemic injury is monitored in vivo. In other aspects, the endothelial cells at the site of ischemic injury can be isolated and their migratory properties can be assayed by a number of in vitro assays including the Boyden chamber assay, under-agarose assay, wound healing assay, Teflon fence assay, phagokinetic track assay, and like assays.

In some embodiments, blood vessel growth is assayed by measuring endothelial cells forming tubes with lumens to conduct the flow of blood, i.e., tubulogenesis. In some embodiments, blood vessel growth is assayed by an aortic ring assay. An aortic ring assay for assaying blood vessel growth is disclosed in Li et al., "Copper promotion of angiogenesis in isolated rat aortic ring: role of vascular endothelial growth factor," Journal of Nutritional Biochemistry 25(2014) 44-49, the disclosure of which is incorporated herein by reference in its entirety. The sprouting microvessels from the aortic ring interact closely with resident macrophages, pericytes, and fibroblasts in an orderly sequence that emulates angiogenesis in the intact animal. In some embodiments, the endothelial cells have not been preselected by passaging and are thus in a quiescent state similar to that of the intact animal. Other angiogenesis assays that incorporate angiogenic functions (such as matrix degradation, migration, proliferation, tube formation) include the embryoid assay, mouse metatarsal assay, and like assays.

In some embodiments, an in vivo assay is used to measure blood vessel growth after administration of a tetramine composition comprising a copper chelating tetramine. These assays include and are not limited to the corneal angiogenesis assay, chick chorioallantoic membrane assay, and Matrigel plug assay. For example, the cornea is the only tissue of the body that is both avascular and transparent, making it ideal for observation of angiogenesis. In some embodiments, pellets or sponges containing proangiogenic molecules (for example, a tetramine composition comprising a copper chelating tetramine as disclosed herein) can be implanted into stromal pockets created surgically. The ingrowth of new vessels from the peripheral limbal vasculature can be monitored daily, allowing rates of angiogenesis to be determined. In a Matrigel plug assay, a Matrigel containing the tetramine composition (with or without copper ion) as disclosed herein can be implanted in an individual at or near the site of ischemic injury, and the Matrigel plug is later removed for visualization of blood vessels. In some embodiments, the endothelial cells are labeled with one or more markers, and their proliferation, migration, tubulogenesis, blood vessel formation, and/or blood vessel growth at the site of ischemic injury are assayed in vivo, for example, using a suitable imaging technique.

Combination Therapy

The tetramine composition and optionally in combination with the copper-promoting composition described above may be used as a single agent or as part of a combination therapy with stem cells or inducers of stem cells to induce repair of an ischemic tissue. In some embodiments, there is provided a method of inducing tissue repair (or improving the function of the tissue) in an individual having ischemic tissue injury, comprising: a) administering to the individual an effective amount of a tetramine composition comprising a copper chelating tetramine; and b) administering to the individual an effective amount of stem cells (such as mesenchymal stem cells (MSC), for example bone marrow mesenchymal stem cells (BMSC)) or an inducer of stem cells. In some embodiments, the method comprises administering to the individual an effective amount of stem cells (such as MSC, for example BMSC). In some embodiments, the method comprises administering to the individual an effective amount of inducer of stem cells. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the method further comprises administering to the individual a copper-promoting composition that can increase the extracellular copper level of the individual. In some embodiments, the individual is previously administered with a copper-promoting composition that can increase the extracellular copper level of the individual. In some embodiments, the copper-promoting composition is a copper ion. In some embodiments, the copper-promoting composition does not comprise a copper ion. In some embodiments, the copper-promoting composition may increase copper uptake, decrease copper excretion and/or decrease zinc toxicity. In some embodiments, the tetramine composition is administered orally. In some embodiments, the ischemic tissue is selected from the group consisting of ischemic heart tissue, ischemic liver tissue, ischemic brain tissue, ischemic lung tissue, ischemic kidney tissue, ischemic skin tissue, ischemic digestive tract tissue, and ischemic skeletal muscle tissue (such as ischemic limb tissue). In some embodiments, the ischemic tissue is ischemic heart tissue. In some embodiments, the ischemic tissue is ischemic brain tissue. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, the stem cell disclosed herein is a mesenchymal stem cell (MSC), a bone marrow mesenchymal stem cell (BMSC), a multipotent stem cell, an induced pluripotent stem cell (iPS), or a tissue-derived stem cell. In some embodiments, the tissue-derived stem cell is an adipose tissue-derived stem cell, a cardiac tissue-derived stem cell, or an umbilical cord tissue-derived stem cell. In some embodiments, the stem cell is an inducer of an adult stem cell. In some embodiments, the adult stem cell is a hematopoietic stem cell, a mammary stem cell, an intestinal stem cell, a mesenchymal stem cell in the placenta, adipose tissue, lung, bone marrow, blood, Wharton's jelly of the umbilical cord, or teeth (such as the perivascular niche of dental pulp and periodontal ligament), an endothelial stem cell, a neural stem cell, an olfactory adult stem cell, a neural crest stem cell, or a germline stem cell (for example, a stem cell in the testicle).

In some embodiments, the inducer of the stem cell disclosed herein is an inducer of a mesenchymal stem cell (MSC), a bone marrow mesenchymal stem cell (BMSC), a multipotent stem cell, an induced pluripotent stem cell (iPS), or a tissue-derived stem cell, such as an adipose tissue-derived stem cell, a cardiac tissue-derived stem cell, or an umbilical cord tissue-derived stem cell. In some embodiments, the inducer of stem cell is an inducer of an adult stem cell, such as a hematopoietic stem cell, a mammary stem cell, an intestinal stem cell, a mesenchymal stem cell in the placenta, adipose tissue, lung, bone marrow, blood, Wharton's jelly of the umbilical cord, or teeth (such as the perivascular niche of dental pulp and periodontal ligament), an endothelial stem cell, a neural stem cell, an olfactory adult stem cell, a neural crest stem cell, or a germline stem cell (for example, a stem cell in the testicle).

In some embodiments, the stem cells or inducer of stem cells are administered systemically. In some embodiments, the stem cells or inducer of stem cells are administered locally to the ischemic tissue. In some embodiments, the stem cells or inducer of stem cells are administered locally to a site other than the site of ischemic injury.

In some embodiments, the stem cells (or inducer of the stem cells), the tetramine composition (with or without copper ion) and optionally the copper-promoting composition are administered simultaneously. In some embodiments, a stem cell disclosed herein (or inducer of the stem cells) and the tetramine composition (with or without copper ion) and optionally the copper-promoting composition are administered sequentially in any suitable order.

Once the stem cells (or inducer of stem cells), the tetramine composition (with or without copper ion) and optionally the copper-promoting composition described herein are administered to a mammal (e.g., a human), the presence and/or biological activity of the cells in some embodiments are monitored by any of a number of known methods. In some embodiments, the cells migrate in vivo from an ischemic tissue of an individual, and the presence and/or biological activity of the cells en route to a tissue damage site is monitored and/or regulated.

While the methods described herein are generally applicable to all aspects of tissue repair, it is to be understood that the combination therapy methods can be used for the purpose of any one or more of the following: inducing the migration of bone marrow mesenchymal stem cells to the ischemic tissue, inducing differentiation of stem cells in the ischemic tissue, inducing tissue regeneration in the ischemic tissue, inducing a signaling molecule that triggers tissue regeneration, promoting copper-dependent HIF-1 transcriptional activities, reversing damage at the site of ischemic injury, and reconstructing the microenvironment of neurofibril cells and neurosecretory cells at the site of ischemic injury.

Methods of Prevention and Prophylactic Use

Also provided herein are methods of preventing ischemic tissue damage in an individual comprising administering to the individual an effective amount of a tetramine composition comprising a copper chelating tetramine. In some embodiments, the ischemic tissue is selected from the group consisting of ischemic heart tissue, ischemic liver tissue, ischemic brain tissue, ischemic lung tissue, ischemic kidney tissue, ischemic skin tissue, ischemic digestive tract tissue, and ischemic skeletal muscle tissue (such as ischemic limb tissue). In some embodiments, the ischemic tissue is ischemic heart tissue. In some embodiments, the ischemic tissue is ischemic brain tissue. In some embodiments, the copper chelating tetramine is trientine. In some embodiments, the tetramine composition further comprises a copper ion. In some embodiments, the copper ion in the tetramine composition is complexed with the copper chelating tetramine. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the copper ion in the tetramine composition is not complexed with the copper chelating tetramine. In some embodiments, the effective amount of the tetramine composition is insufficient to lower the extracellular copper level in the individual. In some embodiments, the method further comprises administering to the individual a copper-promoting composition that can increase the extracellular copper level of the individual. In some embodiments, the individual is previously administered with a copper-promoting composition that can increase the extracellular copper level of the individual. In some embodiments, the copper-promoting composition is a copper ion. In some embodiments, the copper-promoting composition does not comprise a copper ion. In some embodiments, the copper-promoting composition may increase copper uptake, decrease copper excretion and/or decrease zinc toxicity. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily.

In some embodiments, there is provided a method of preventing ischemic heart failure in an individual, comprising administering to the individual an effective amount of a tetramine composition comprising a copper chelating tetramine (such as trientine). In some embodiments, the effective amount of the tetramine composition is insufficient to lower the extracellular copper level in the individual. In some embodiments, the tetramine composition is administered orally. In some embodiments, the effective amount of the tetramine composition is about 80 mg to about 450 mg (such as about 80 mg to about 300 mg, or about 150 mg to about 350 mg) per day. In some embodiments, the tetramine composition is administered twice daily. In some embodiments, the tetramine composition is administered for at least about 1 month (such as at least about 3 months or at least about 6 months). In some embodiments, the individual has a left ventricular ejection function (LVEF) of no more than about 35% at baseline. In some embodiments, the individual has class II or class III heart failure (based on New York Heart Association or NYHA Functional classification). In some embodiments, the individual has at least about 150 pg/mL of plasma B-type natriuretic peptide (BNP). In some embodiments, the individual has no less than about 600 pg/mL of NT-proBNP (N-terminal pro-BNP).

"Preventing," as used herein, includes providing prophylaxis with respect to the occurrence or recurrence of a disease in an individual that may be predisposed to the disease but has not yet been diagnosed with the disease. In some embodiments, the provided cells and compositions are used to delay development of a disease or to slow the progression of a disease such as tissue injury.

For the prevention or treatment of disease, the appropriate dosage or route of administration depend on the type of disease to be treated, the severity and course of the disease, whether the cells are administered for preventive or therapeutic purposes, previous therapy, the individual's clinical history and response to the tetramine compositions and/or the cells, and the discretion of the attending physician. The tetramine compositions, the copper-promoting compositions, stem cells, and stem cell inducers are in some embodiments suitably administered to the individual at one time or over a series of treatments.

In some embodiments, the present disclosure provides compositions and methods for treating and preventing ischemic tissue damage. In some embodiments, the tetramine compositions, the copper-promoting compositions, and/or cells disclosed herein are administered prior to, during, and/or after a treatment which will or likely will cause tissue damage in an individual, and the administration prevents or reduces ischemic tissue damage associated with the treatment, such as cancer radiotherapy and chemotherapy.

In some embodiments, the tetramine composition or method disclosed herein prevents an ischemic tissue damage or reduces the area, volume, or duration of an ischemic tissue damage, by inducing migration (e.g., homing) of a stem cell to the tissue, even after the tissue in the individual has otherwise lost the inherent ability to spontaneously recruit stem cells. In embodiments, administration of the tetramine composition and/or cells of the present disclosure triggers a series of other events leading to enhanced resistance to an ischemic tissue damage, including, for example inducing differentiation of stem cells at the tissue site, inducing tissue regeneration at the tissue site, inducing a signaling molecule that triggers tissue regeneration, promoting copper-dependent HIF-1 transcriptional activities, reversing damage at the site of an initial ischemic injury before additional damage is done, and/or reconstructing the microenvironment of neurofibril cells and neurosecretory cells at the tissue site.

For example, myocardial ischemia or infarction can lead to irreversible loss of functional cardiac tissue with possible deterioration of pump function and death. Occlusion of a coronary vessel leads to interruption of the blood supply of the dependent capillary system. Without nutrition and oxygen, cardiomyocytes die and undergo necrosis. An inflammation of the surrounding tissue occurs with invasion of inflammatory cells and phagocytosis of cell debris. A fibrotic scarring occurs, and the afflicted region of the heart loses it contractile force. Without intervention, the only way for the cardiac muscle to compensate for the tissue loss is hypertrophy of the remaining cardiomyocytes (accumulation of cellular protein and contractile elements inside the cell). Endocrine, metabolic (alcohol) or infectious (virus myocarditis) agents and cancer treatment agents also lead to cell death, with a consequently reduced myocardial function. In some embodiments, the tetramine composition or method disclosed herein prevents ischemic cardiac tissue damage or reduces the area, volume, or duration of ischemic cardiac tissue damage. In some embodiments, the tetramine composition disclosed herein induces migration (e.g., homing) and/or retention of mesenchymal stem cells (e.g., BMSCs) to the ischemic cardiac tissue. In some embodiments, in cases of myocardial ischemia or infarction, cardiac muscle can compensate for the tissue loss via differentiation of the stem cells to cardiomyocytes, thereby avoiding or reducing cardiac hypertrophy and further cardiac tissue damage.

Tetramine Compositions

Further provided herein are tetramine compositions (including pharmaceutical compositions) comprising a copper chelating tetramine (such as trientine) for increasing intracellular copper level, delivering copper to cells, inducing at least one (such as at least any of 2, 3, 4, 5, 6, 7, or more) events of tissue repair, inducing migration of stem cells, or promoting copper-dependent HIF-1 transcriptional activities in an ischemic tissue of an individual having ischemic tissue injury. Any of the tetramine compositions, optionally in combination with copper-promoting compositions and/or stem cells (or stem cell inducer), may be used in the methods described above.

In some embodiments, there is provided a tetramine composition comprising a copper chelating tetramine or a pharmaceutically acceptable salt thereof. The copper chelating tetramine (such as trientine) contemplated herein include, but are not limited to, the copper chelating tetramine compound itself, pharmaceutically acceptable salts thereof, active metabolites thereof, prodrugs thereof, and derivatives thereof. In some embodiments, the copper chelating tetramine is trientine. In some embodiments, the copper chelating tetramine is an analog of trientine, such as a tetramine of Formula (II) as described in the section of "Copper and copper chelating tetramines". In some embodiments, the tetramine composition does not comprise a trace element, such as copper. In some embodiments, the composition can chelate copper ion in the blood and deliver the copper ion into cells of an ischemic tissue.

In some embodiments, there is provided a tetramine composition comprising a mixture of a copper chelating tetramine and a copper ion. In some embodiments, the tetramine composition comprises a mixture of trientine and a copper ion. In some embodiments, the relative ratio (mole by mole) of the copper chelating tetramine (such as trientine) to the copper ion is about any one of 100:1, 50:1, 20:1, 10:1, 5:1, 4:1, 3:1, 2:1, 1:1, 1:2, 1:3, 1:4, 1:5, 1:10, 1:20, 1:50, or 1:100. In some embodiments, the relative molar ratio of the copper chelating tetramine (such as trientine) to the copper ion is about 1:1. In some embodiments, the relative ratio (mole by mole) of the copper chelating tetramine (such as trientine) to the copper ion is about any one of 50:1-100:1, 20:1-50:1, 10:1-20:1, 5:1-10:1, 4:1-5:1, 3:1-4:1, 2:1-3:1, 1:1-2:1, 1:2-1:1, 1:3-1:2, 1:4-1:3, 1:5-1:4, 1:10-1:5, 1:20-1:10, 1:50-1:20, 1:100-1:50, 1:100-1:10, 1:10-1:1, 1:1-10:1, 10:1-100:1, or 1:10-10:1. In some embodiments, at least a fraction of the copper ion is in complex with the copper chelating tetramine. In some embodiments, the copper ion is not in complex with the copper chelating tetramine.

In some embodiments, there is provided a tetramine composition comprising a complex of a copper chelating tetramine and a copper ion. In some embodiments, the tetramine composition comprises a complex of trientine and a copper ion. In some embodiments, the stoichiometry of the copper chelating tetramine (such as trientine) to the copper ion is about 1:1. In some embodiments, the complex of the copper chelating tetramine (such as trientine) and the copper ion is crystalline. In some embodiments, the crystalline complex of the copper chelating tetramine (such as trientine) and the copper ion is a thermodynamic polymorph. Different thermodynamic polymorphs of the crystalline complex can be described by a specific set of geometric structures, unit cell dimensions, space groups, and structural coordinates, which may be determined using skills known in the art, such as x-ray crystallography. In some embodiments, the tetramine composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiments, the tetramine composition comprises a crystalline complex of Formula (I) as shown below,

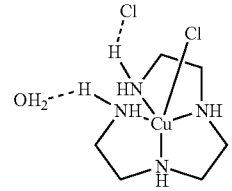

Formula (I)

wherein Cu is a copper ion and dotted lines denote hydrogen bonds. In some embodiments, the tetramine composition comprises a crystalline complex of trientine and a copper ion, wherein the crystalline complex has the crystal structure as shown in FIG. 1. In some embodiments, the crystal structure has bond lengths, bond angles, and torsional angles as listed in FIG. 2. In some embodiments, the crystalline complex comprises crystals with the space group and parameters as listed in FIG. 3. In some embodiments, the tetramine composition comprises a crystalline complex of trientine and a copper ion, wherein the crystal structure of the crystalline complex is defined by the atomic coordinates as listed in FIGS. 4A-4C.

In some embodiments, the tetramine composition comprises a complex of the copper chelating tetramine (such as trientine) and the copper ion, wherein the complex is not crystalline. In some embodiments, the tetramine composition further comprises the copper ion not in complex with the copper chelating tetramine. In some embodiments, the relative ratio (mole by mole) of the copper ion not in complex with the copper chelating tetramine to the complex is about any one of 1:1, 1:2, 1:3, 1:4, 1:5, 1:10, 1:20, 1:50, or 1:100. In some embodiments, the relative ratio (mole by mole) of the copper ion not in complex with the copper chelating tetramine to the complex is about any one of 1:2-1:1, 1:3-1:2, 1:4-1:3, 1:5-1:4, 1:10-1:5, 1:20-1:10, 1:50-1:20, 1:100-1:50, 1:100-1:10, or 1:10-1:1. In some embodiments, the percentage of total copper in the tetramine composition that is in complex with the copper chelating tetramine (such as trientine) is about any one of 1%, 5%, 10%, 20%, 30%, 40%, 50%, 60%, 70%, 80%, 90%, 95%, or 100%. In some embodiments, the percentage of total copper in the tetramine composition that is in complex with the copper chelating tetramine (such as trientine) is about any one of 1%-5%, 5%-10%, 10%-20%, 20%-30%, 30%-40%, 40%-50%, 50%-60%, 60%-70%, 70%-80%, 80%-90%, 90%-100%, 1%-10%, 10%-50%, 50%-80%, or 80%-100%. In some embodiments, the percentage of total copper chelating tetramine (such as trientine) in the tetramine composition that is in complex with the copper ion is at least about any one of 1%, 5%, 10%, 20%, 30%, 40%, 50%, 60%, 70%, 80%, 90%, 95%, or 100%. In some embodiments, the percentage of total copper chelating tetramine (such as trientine) in the tetramine composition that is in complex with the copper ion is about any one of 1%-5%, 5%-10%, 10%-20%, 20%-30%, 30%-40%, 40%-50%, 50%-60%, 60%-70%, 70%-80%, 80%-90%, 90%-100%, 1%-10%, 10%-50%, 50%-80%, or 80%-100%. In some embodiments, the copper ion not in complex with the copper chelating tetramine (such as trientine) is present as a salt, such as copper sulfate, copper chloride, copper oxide, copper nitrate, copper acetate, copper formate, copper gluconate, copper amino acid chelates, and the like.

In some embodiments, there is provided a tetramine composition comprising a copper chelating tetramine and a copper ion, wherein the copper ion is not complexed with the copper chelating tetramine. In some embodiments, the tetramine composition comprises trientine and a copper ion, wherein the copper ion is not complexed with trientine. In some embodiments, the copper ion is present as a salt, such as copper sulfate, copper chloride, copper oxide, copper gluconate, copper amino acid chelates, and the like. In some embodiments, the relative ratio (mole by mole) of the copper chelating tetramine (such as trientine) to the copper ion is about any one of 100:1, 50:1, 20:1, 10:1, 5:1, 4:1, 3:1, 2:1, 1:1, 1:2, 1:3, 1:4, 1:5, 1:10, 1:20, 1:50, or 1:100. In some embodiments, the relative ratio (mole by mole) of the copper chelating tetramine (such as trientine) to the copper ion is about any one of 50:1-100:1, 20:1-50:1, 10:1-20:1, 5:1-10:1, 4:1-5:1, 3:1-4:1, 2:1-3:1, 1:1-2:1, 1:2-1:1, 1:3-1:2, 1:4-1:3, 1:5-1:4, 1:10-1:5, 1:20-1:10, 1:50-1:20, 1:100-1:50, 1:100-1:10, 1:10-1:1, 1:1-10:1, 10:1-100:1, or 1:10-10:1.

Many factors of the tetramine composition, including, but not limited to, chemical structure of the copper-chelating tetramine, the ratio of the copper-chelating tetramine to copper in the tetramine composition, interactions of the copper ion with the copper-chelating tetramine (e.g. whether in a complex, whether the complex is crystalline, etc.), can affect the capacity of the tetramine composition to deliver (such as unload) copper inside cells at an ischemic tissue. For example, the copper chelating tetramine may have a conformation (including chelate denticity, donor binding groups, and cavity size) that promotes reversible binding of the copper ion. In some embodiments, the tetramine composition comprises a copper chelating tetramine with sufficiently low affinity to the copper ion inside cells at the ischemic tissue, wherein the tetramine composition dissociates and unloads the copper ion inside cells. In some embodiments, the tetramine composition comprises additional compounds and/or agents that enhance unloading of copper ion inside cells at the ischemic tissue.

Further provided are pharmaceutical compositions, comprising any of the tetramine compositions described herein and one or more pharmaceutically acceptable carriers, excipients, stabilizing agents, diluents, and/or other agents, which are known in the art, for use in the methods described herein.

Accordingly, in one aspect of the present application, there is provided a pharmaceutical composition comprising a copper chelating tetramine and a copper ion. In some embodiments, there is provided a pharmaceutical composition comprising trientine and a copper ion.

In some embodiments, there is provided a pharmaceutical composition comprising a complex of a copper chelating tetramine and a copper ion. In some embodiments, there is provided a pharmaceutical composition comprising a complex of trientine and a copper ion. In some embodiment, the complex of the copper chelating tetramine (such as trientine) and the copper ion is crystalline. In some embodiments, the crystalline complex of the copper chelating tetramine (such as trientine) and the copper ion is a thermodynamic polymorph. In some embodiments, the pharmaceutical composition comprises a crystalline complex of trientine and a copper ion, wherein the copper ion is chelated by the four amine groups of trientine to adopt a square-planar geometry, and wherein the crystalline complex further comprises two chloride ions and a water molecule. In some embodiment, the complex of the copper chelating tetramine (such as trientine) and the copper ion is not crystalline.

In some embodiments, there is provided a pharmaceutical composition comprising a copper chelating tetramine and a copper ion, wherein at least a fraction (such as at least about any of 10%, 20%, 30%, 40%, 50%, 60%, 70%, 80%, 90% or more) of the copper ion is not in a complex with the copper chelating tetramine. In some embodiments, there is provided a pharmaceutical composition comprising trientine and a copper ion, wherein at least a fraction (such as at least about any of 10%, 20%, 30%, 40%, 50%, 60%, 70%, 80%, 90% or more) of the copper ion is not in a complex with trientine. In some embodiments, there is provided a pharmaceutical composition comprising a copper chelating tetramine and a copper ion, wherein the copper ion is not complexed with the copper chelating tetramine. In some embodiments, there is provided a pharmaceutical composition comprising trientine and a copper ion, wherein the copper ion is not complexed with the copper chelating tetramine. In some embodiments, the copper ion not in complex with the copper chelating tetramine is present as a salt, such as copper sulfate, copper chloride, copper oxide, copper nitrate, copper acetate, copper formate, copper gluconate, copper amino acid chelates, and the like.

Any of the pharmaceutical compositions described herein may be used to increase intracellular copper level in an ischemic tissue in an individual having ischemic tissue injury, inducing at least two (such as any of at least 2, 3, 4, 5, 6, 7, or more) events of tissue repair, promoting copper-dependent HIF-1 transcriptional activities, and/or treating (including preventing) any disease or condition associated with ischemic tissue injury.

The pharmaceutical compositions described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. In some embodiments, the pharmaceutical composition is formulated for oral administration. In some embodiments, the pharmaceutical composition is formulated for parental administration (such as intravenous administration).

For oral administration, the pharmaceutical composition may be provided in a solid form, such as a tablet or capsule, or as a solution, emulsion, or suspension. In some embodiments, the pharmaceutical composition is formulated as a tablet, a capsule or a pill. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating. The oral formulations may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol. Capsules may also contain gelatin, iron oxides, stearic acid, and titanium dioxide as inactive ingredients.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the tetramine compositions may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Formulations suitable for parenteral including intravenous administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Dosing and Methods of Administration

When used in vivo for any one of the treatment methods described herein, the tetramine composition (including pharmaceutical composition), and optionally the copper-promoting composition and/or stem cells (or stem cell inducer) are administered to the individual in effective amounts. An "effective amount" is at least the minimum concentration required to effect a measurable improvement or prevention of the disease or condition associated with the ischemic tissue injury. An effective amount herein may vary according to factors such as the degree of the ischemic injury in the individual, the characteristics of the particular tetramine composition, the copper ion and/or stem cells (or stem cell inducers) used, e.g., its therapeutic index, the individual (such as age, gender, weight and medical history). An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease or condition, including biochemical, histological and/or behavioral symptoms of the disease or condition, its complications and intermediate pathological phenotypes presenting during development of the disease or condition. For therapeutic use, beneficial or desired results include clinical results such as decreasing one or more symptoms resulting from the disease or condition, increasing the quality of life of those suffering from the disease, decreasing the dose of other medications required to treat the disease, enhancing effect of another medication such as via targeting, delaying the progression of the disease, and/or prolonging survival.

In some embodiments, the effective amount of the tetramine composition (such as pharmaceutical composition) and optionally in combination with the effective amount of the copper-promoting composition are effective to result in an increase of more than about any of 10%, 20%, 30%, 40%, 50%, 60%, 70%, 80%, 90%, 100%, 200%, 300%, 400%, 500% or more in the intracellular copper level in the ischemic tissue of the individual as compared to the intracellular copper level of the ischemic tissue of the individual prior to the treatment. In some embodiments, the effective amount of the tetramine composition (such as pharmaceutical composition) and optionally in combination with the effective amount of the copper-promoting composition are effective to result in an increase of more than about any of 10%, 20%, 30%, 40%, 50%, 60%, 70%, 80%, 90%, 100%, 200%, 300%, 400%, 500% or more in the total copper level of an ischemic tissue in the individual as compared to the total copper level of the ischemic tissue in the individual prior to the treatment. In some embodiments, the effective amount of the tetramine composition (such as pharmaceutical composition) and optionally in combination with the effective amount of the copper-promoting composition do not lower the extracellular copper level (such as the copper level in blood) in the individual. In some embodiments, the effective amount of the tetramine composition (such as pharmaceutical composition) and optionally in combination with the effective amount of the copper-promoting composition do not lower the extracellular copper level (such as the copper level in blood) in the individual by more than about any one of 5%, 10%, 20%, 30%, 40%, 50% or more as compared to the extracellular copper level of the individual prior to the treatment. In some embodiments, the effective amount of the tetramine composition (such as pharmaceutical composition) and optionally in combination with the effective amount of the copper-promoting composition do not lower the total copper level in the individual. In some embodiments, the effective amount of the tetramine composition (such as pharmaceutical composition) and optionally in combination with the effective amount of the copper-promoting composition do not lower the total copper level in the individual by more than about any one of 5%, 10%, 20%, 30%, 40%, 50% or more as compared to the total copper level in the individual prior to the treatment.

An effective amount can be administered in one or more administrations. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

The effective amount, doses and dosing regimen, of the tetramine composition alone, or in combination with the copper-promoting composition (such as copper ion) and/or stem cells (or stem cell inducer) may be determined during pre-clinical trials and clinical trials by methods familiar to physicians and clinicians. In some embodiments, the effective amount of the copper chelating tetramine (such as trientine) in the tetramine composition is less than about any one of 0.5 mg, 5 mg, 10 mg, 25 mg, 50 mg, 80 mg, 100 mg, 125 mg, 150 mg, 175 mg, 200 mg, 225 mg, 250 mg, 275 mg, 300 mg, 350 mg, 400 mg, 500 mg, 600 mg, or 1200 mg. In some embodiments, the effective amount of the copper chelating tetramine (such as trientine) in the tetramine composition is any one of about 0.5 mg to about 5 mg, about 5 mg to about 10 mg, about 10 mg to about 25 mg, about 25 mg to about 50 mg, about 50 mg to about 75 mg, about 75 mg to about 100 mg, about 100 mg to about 125 mg, about 125 mg to about 150 mg, about 150 mg to about 175 mg, about 175 mg to about 200 mg, about 200 mg to about 225 mg, about 225 mg to about 250 mg, about 250 mg to about 275 mg, about 275 mg to about 300 mg, about 300 mg to about 350 mg, about 350 mg to about 400 mg, about 400 mg to about 500 mg, about 500 mg to about 600 mg, about 600 mg to about 1200 mg, about 1200 mg to about 2400 mg, about 0.5 mg to about 50 mg, about 50 mg to about 100 mg, about 10 mg to about 125 mg, about 80 mg to about 200 mg, about 150 mg to about 300 mg, about 200 mg to about 300 mg, about 300 mg to about 600 mg, about 0.5 mg to about 200 mg, about 80 mg to about 300 mg, or about 80 mg to about 400 mg, or about 80 mg to about 450 mg. In some embodiments, the effective amount of the tetramine composition is about 80 mg to about 450 mg of the copper chelating tetramine (such as in dichloride salt form) per day for a human patient.

In some embodiments, the effective amount of copper chelating tetramine (such as trientine) in the tetramine composition (such as pharmaceutical composition) includes at least about any of 1 mg/kg, 2.5 mg/kg, 5 mg/kg, 7.5 mg/kg, 10 mg/kg, 15 mg/kg, or 20 mg/kg. In some embodiments, the effective amount of copper chelating tetramine (such as trientine) in the tetramine composition (such as pharmaceutical composition) includes less than about any of 35 mg/kg, 30 mg/kg, 25 mg/kg, 20 mg/kg, 18 mg/kg, 15 mg/kg, 10 mg/kg, 5 mg/kg, 2.5 mg/kg, 2 mg/kg, 1 mg/kg, 0.5 mg/kg, or 0.1 mg/kg. In some embodiments, the effective amount of copper chelating tetramine in the tetramine composition is any one of about 1 mg/kg to about 10 mg/kg, about 10 mg/kg to about 15 mg/kg, about 15 mg/kg to about 20 mg/kg, about 20 mg/kg to about 25 mg/kg, about 25 mg/kg to about 30 mg/kg, about 30 mg/kg to about 40 mg/kg, about 1 mg/kg to about 100 mg/kg, about 10 mg/kg to about 50 mg/kg, about 15 mg/kg to about 50 mg/kg, about 15 mg/kg to about 40 mg/kg, or about 20 mg/kg to about 35 mg/kg per day. In some embodiments, the effective amount of the tetramine composition is no more than about 20 mg/kg per day, such as about 18 mg/kg per day for a rhesus monkey. In some embodiments, the effective amount of the tetramine composition is no more than about 15 mg/kg to about 35 mg/kg per day for a mouse.

In some embodiments, the effective amount of the copper chelating tetramine (such as trientine) in the pharmaceutical composition (e.g., a unit dosage form) is in the range of about 5 mg to about 300 mg, such as about 80 mg to about 150 mg, about 80 mg to about 200 mg, about 200 mg to about 300 mg, or about 80 mg to about 300 mg. In some embodiments, the concentration of the copper-chelating tetramine (such as trientine) in the pharmaceutical composition is dilute (about 0.1 mg/ml) or concentrated (about 100 mg/ml), including, for example, any one of about 0.1 to about 50 mg/ml, about 0.1 to about 20 mg/ml, or about 1 to about 10 mg/ml.

Exemplary dosing frequencies include, but are not limited to, any one of four times per day, three times per day, twice daily, daily, once per two days, once per three days, once per four days, or weekly. In some embodiments, the tetramine composition (such as pharmaceutical composition) is administered at least about any one of 1×, 2×, 3×, 4×, 5×, 6×, or 7× (i.e., daily) a week. In some embodiments, the intervals between each administration are less than about any one of 7 days, 6 days, 5 days, 4 days, 3 days, 2 days, 1 day, 12 hours, 6 hours, 4 hours, or 3 hours. In some embodiments, the tetramine composition is administered daily. In some embodiments, the tetramine composition is administered at least twice daily. In some embodiments, the tetramine composition is administered at least once, including, for example at least any of 2×, 3×, or 4× daily.

In some embodiments, the effective amount of the tetramine composition combined with the dosing frequency are sufficient to maintain a high concentration of the tetramine (such as trientine) in the individual, such as in the blood or in the ischemic tissue. In some embodiments, a high concentration of the tetramine is a concentration that promotes copper-dependent HIF-1 transcriptional activities, or to induce at least one (including at least 2, 3, 4, 5, 6, 7, or more) events of tissue repair. In some embodiments, administration of the tetramine composition (such as pharmaceutical composition) leads to at least about 0.005 mg/L (including, for example, at least about any of 0.01 mg/L, 0.05 mg/L, 0.1 mg/L, 0.5 mg/mL, 1.0 mg/L, 2.0 mg/L, 3.0 mg/L, 4.0 mg/L or 5.0 mg/L) of the copper chelating tetramine in the blood. Concentration of the tetramine in a biological sample (such as blood or biopsy of an ischemic tissue) can be determined using methods known in the art, such as fluorescence spectroscopy, mass spectroscopy, or chromatography methods, or by measuring level of a labeled tetramine.

In some embodiments, the effective amount of the tetramine composition combined with the dosing frequency are sufficient to maintain a high concentration of the tetramine (such as trientine) in the individual for at least about any of 4, 5, 6, 7, 8, 9, 10 or more hours. In some embodiments, the effective amount of the tetramine composition combined with the dosing frequency are sufficient to maintain a high concentration of the tetramine (such as trientine) in the individual for at least about 8 hours.

In some embodiments, the effective amount of the tetramine composition is about at least any of 1 mg/kg/day, 2 mg/kg/day, 5 mg/kg/day, 10 mg/kg/day, 12 mg/kg/day, 15 mg/kg/day, 18 mg/kg/day, 20 mg/kg/day, 30 mg/kg/day, 40 mg/kg/day, 50 mg/kg/day, or more of trientine in the tetramine composition. In some embodiments, the effective amount of the tetramine composition is no more than any of 1 mg/kg/day, 2 mg/kg/day, 5 mg/kg/day, 10 mg/kg/day, 12 mg/kg/day, 15 mg/kg/day, 18 mg/kg/day, 30 mg/kg/day, 40 mg/kg/day, or 50 mg/kg/day, of trientine in the tetramine composition. In some embodiments, the effective amount of the tetramine composition is any of about 1 mg/kg/day to about 2 mg/kg/day, about 2 mg/kg/day to about 5 mg/kg/day, about 5 mg/kg/day to about 10 mg/kg/day, about 10 mg/kg/day to about 15 mg/kg/day, about 15 mg/kg/day to about 20 mg/kg/day, about 20 mg/kg/day to about 30 mg/kg/day, about 30 mg/kg/day to about 50 mg/kg/day, about 1 mg/kg/day to about 5 mg/kg/day, about 5 mg/kg/day to about 15 mg/kg/day, about 1 mg/kg/day to about 10 mg/kg/day, or about 1 mg/kg/day to about 18 mg/kg/day of trientine in the tetramine composition. In some embodiments, the effective amount of the tetramine composition is about 18 mg/kg/day of trientine in the tetramine composition. In some embodiments, the effective amount of the tetramine composition is about 1 mg/kg/day to about 10 mg/kg/day of trientine in the tetramine composition.

The administration of the tetramine composition (such as pharmaceutical composition) can be over an extended period of time, such as from about any one of one week up to about several years. In some embodiments, the tetramine composition (such as pharmaceutical composition) is administered over a period of at least about any one of 1, 2, 3, 4, 5, 6, 7, 8, 9, 10, 11, 12, 18, 24, 30, 36, 48, 60, 72, or 84 months or more. In some embodiments, the tetramine composition (such as pharmaceutical composition) is administered for at least about one month, including, for example, about any of 1, 2, 3, 4, 5, 6, 8, 10, 12 or more months. In some embodiments, the tetramine composition (such as pharmaceutical composition) is administered for at least about one month, and wherein the tetramine composition is administered at least once (such as twice, three times, or four times) daily. In some embodiments, the administration of the tetramine composition (including pharmaceutical composition) leads to at least about 0.005 mg/L (including, for example, at least about any of 0.01 mg/L, 0.05 mg/L, 0.1 mg/L, 0.5 mg/mL, 1.0 mg/L, 2.0 mg/L, 3.0 mg/L, 4.0 mg/L or 5.0 mg/L) of the copper chelating tetramine in the blood for at least about 1 week (including, for example, at least about any of 2 weeks, 1 months, 2 months, 3 months, 4 months, 6 months, 12 months or more).

Any of the tetramine compositions (such as pharmaceutical compositions) described herein can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, transdermal, intratumoral, direct injection into the blood vessel wall, intracranial, or intra-cavity. In some embodiments, sustained continuous release formulation of the tetramine composition (such as pharmaceutical composition) may be used. In some embodiments, the tetramine composition is administered parentally. In some embodiments, the tetramine composition is administered orally. In some embodiments, the tetramine composition is administered directly to the ischemic tissue (e.g. using direct delivery methods described below). In some embodiments, the tetramine composition is administered via an intervention method, such as angioplasty.

In some embodiments, the tetramine composition (such as pharmaceutical composition) may be administered with a second therapeutic compound and/or a second therapy. The dose and dosing frequency of the tetramine composition (such as pharmaceutical composition) and the second compound may be adjusted over the course of the treatment based on the judgment of the administering physician. In some embodiments, the first and second therapies are administered simultaneously, sequentially, or concurrently. "Simultaneous administration," as used herein, may indicate that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition). "Sequential administration" may indicate that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits. Concurrent administration may indicate that the administration of the first therapy and that of a second therapy in a combination therapy overlap with each other. When administered separately, the pharmaceutical composition and the second compound can be administered at different dosing frequency or intervals. For example, the tetramine composition (such as pharmaceutical composition) can be administered daily, while a second compound can be administered more or less frequently. In some embodiments, sustained continuous release formulation of the tetramine composition and/or second compound may be used. Various formulations and devices for achieving sustained release are known in the art. A combination of the administration configurations described herein can be used. In some embodiments, the second compound is a copper ion (such as a copper salt, or chelated copper). In some embodiments, the second therapy comprises stem cells or a stem cell inducer.

In some embodiments, an effective amount of a copper-promoting composition comprising a copper ion is further administered to the individual. In some embodiments, the effective amount of the copper-promoting composition administered to the individual is sufficient to increase the extracellular copper level of the individual by about any one of 10%, 20%, 30%, 40%, 50%, 60%, 70%, 80%, 90%, 100%, 200%, 300%, or more as compared to the extracellular copper level of the individual prior to the treatment. In some embodiments, the effective amount of the copper-promoting composition administered to the individual is sufficient to increase the total copper level of the ischemic tissue of the individual by about any one of 10%, 20%, 30%, 40%, 50%, 60%, 70%, 80%, 90%, 100%, 200%, 300%, or more as compared to the total copper level of the ischemic tissue of the individual prior to the treatment.

In some embodiments, an effective amount of the copper-promoting composition administered to the individual is sufficient to increase the extracellular copper level of the individual by about any one of 10%, 20%, 30%, 40%, 50%, 60%, 70%, 80%, 90%, 100%, 200%, 300%, or more as compared to the extracellular copper level of the individual prior to the treatment. In some embodiments, the effective amount of the copper-promoting composition administered to the individual is sufficient to increase the total copper level of the ischemic tissue of the individual by about any one of 10%, 20%, 30%, 40%, 50%, 60%, 70%, 80%, 90%, 100%, 200%, 300%, or more as compared to the total copper level of the ischemic tissue of the individual prior to the treatment. In some embodiments, a copper-promoting composition that does not comprise a copper ion may be used to increase the extracellular copper level. For example, the copper-promoting composition may increase copper intake, decrease excretion of copper, and/or decrease zinc toxicity.

In some embodiments, the effective amount of the copper ion in a copper-promoting composition comprising a copper ion is included in any of the following ranges: about 0.01 mg to about 0.1 mg, about 0.1 mg to about 0.5 mg, about 0.5 mg to about 1 mg, about 1 mg to about 2 mg, about 2 mg to about 3 mg, about 3 mg to about 4 mg, about 4 mg to about 5 mg, about 5 mg to about 8 mg, about 8 mg to about 10 mg, about 0.01 mg to about 1 mg, or about 0.1 mg to about 2.5 mg. In some embodiments, the effective amount of the copper ion in the copper-promoting composition administered to the individual includes at least about any one of 5 mcg/kg, 10 mcg/kg, 20 mcg/kg, 30 mcg/kg, 50 mcg/kg, 100 mcg/kg, 200 mcg/kg, 300 mcg/kg, 400 mcg/kg, 500 mcg/kg, 600 mcg/kg, 700 mcg/kg, 800 mcg/kg, 900 mcg/kg, or 1000 mcg/kg. In some embodiments, the effective amount of the copper ion in the copper-promoting composition administered to the individual includes less than about any one of 1000 mcg/kg, 900 mcg/kg, 800 mcg/kg, 700 mcg/kg, 600 mcg/kg, 500 mcg/kg, 400 mcg/kg, 300 mcg/kg, 200 mcg/kg, 100 mcg/kg, 50 mcg/kg, 30 mcg/kg, 20 mcg/kg, 10 mcg/kg, or 5 mcg/kg.

In some embodiments, the copper-promoting composition is administered daily or twice daily. In some embodiments, the copper-promoting composition is administered with the same dosing frequency and duration as the tetramine composition. In some embodiments, the copper-promoting composition is administered with different dosing frequency and/or duration as the tetramine composition. In some embodiments, the copper-promoting composition is administered orally. The effective amount and dosing frequency of the copper-promoting composition may be determined during pre-clinical trials and clinical trials by methods familiar to physicians and clinicians.

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Various direct delivery methods are known in the art, and may be used to administer the tetramine composition (such as pharmaceutical composition) and/or the copper-promoting composition.

In some embodiments, the tetramine composition and/or the copper-promoting composition is delivered via a microbubble. In some embodiments, the copper ion is delivered via peptide-based nanoparticles comprising copper. In some embodiments, the tetramine composition and/or the copper-promoting composition are delivered or targeted to the ischemic tissue passively via a physical effect inducing release or delivery to the ischemic tissue through a nanoparticle (or microsphere).

In some embodiments, the tetramine composition and/or the copper-promoting composition is delivered by directly administering the tetramine composition and/or the copper-promoting composition to the ischemic tissue. In some embodiments, the tetramine composition and/or the copper-promoting composition disclosed herein is orally administered to the site of ischemic tissue injury. In some embodiments, the tetramine composition and/or the copper-promoting composition is absorbed via the digestive track. In one aspect, the absorbed composition and/or copper ion is targeted (by active targeting or passive targeting) to an ischemic injury site, and is released locally at the ischemic injury site to provide an effective local concentration of the tetramine composition and/or the copper-promoting composition for tissue repair. In some embodiments, the orally delivered copper ion forms a compound or complex with a protein, peptide, amino acid, or mono-, di-, or polysaccharide. In some embodiments, the copper ion forms a compound or complex with one or more polymers. In other embodiments, the copper ion is in an organometallic compound, such as a small molecule organometallic compound.

In some embodiments, a sustained delivery composition disclosed herein includes long-acting injectables (e.g., oil-based injections, injectable suspensions, injectable microspheres, and injectable in situ systems) containing the tetramine composition and/or the copper composition, agents and polymers for depot injections, commercially available depot injections, and injectable sustained-release delivery systems. In certain embodiments, a sustained delivery composition disclosed herein comprises a polymeric matrix from which an agent is released by diffusion and/or degradation of the polymer matrix. Hence, the release pattern of the agent is principally determined by the polymer matrix, as well as by the percent loading and method of manufacture. In some embodiments, the sustained release preparations use a biodegradable polymer. In this case, the sustained release preparations do not require the surgical removal of the preparations from the subject. Typically, such preparations are slowly degraded and absorbed by the patient's body, and ultimately disposed of along with other soluble metabolic waste products.

In some embodiments, a polymeric injectable depot system is used to deliver an in-situ-forming implant containing the tetramine composition and/or the copper composition at the site of ischemic injury. In situ-forming implant systems are typically made of biodegradable products, which can be injected via a syringe into the body, and once injected, congeal to form a solid biodegradable implant. In some embodiments, the implant is formed by thermoplastic pastes, in situ cross-linked polymers, in situ polymer precipitation, thermally induced gelling, or in situ solidifying organogels. The mechanism of depot formation of thermoplastic pastes is to form a semisolid upon cooling to body temperature after injection into the body in the molten form. Cross-linked polymer networks can be achieved in situ in various ways, forming solid polymer systems or gels. Methods for in situ cross-linked systems include free radical reactions, usually initiated by heat or absorption of photons, or ionic interactions between small cations and polymer anions. In situ formings can be produced by causing polymer precipitation from solution. A water-insoluble and biodegradable polymer is solubilized in a biocompatible organic solvent to which a drug is added which forms a solution or suspension after mixing. When this formulation is injected into the body, the water-miscible organic solvent dissipates and water penetrates into the organic phase. This leads to phase separation and precipitation of the polymer forming a depot at the site of injection. Thermally induced gelling systems show thermo-reversible sol/gel transitions and are characterized by a lower critical solution temperature. They are liquid at room temperature and produce a gel at and above the lower critical solution temperature. In situ solidifying organogels comprises water-insoluble amphiphilic lipids, which swell in water and form various types of lyotropic liquid crystals.

In some embodiments, the tetramine composition and/or the copper-promoting composition is injected to the ischemic injury site, for example, by direct percutaneous puncture, by an interventional catheter, or by intravertebral injection. In some embodiments, the tetramine composition and/or the copper-promoting composition is delivered directly to an ischemic injury site by using a coated implant, stent, or plate, or an implant impregnated with the tetramine composition and/or the copper-promoting composition. In some embodiments, the tetramine composition and/or the copper-promoting composition is delivered directly to an ischemic injury site by slowly releasing the tetramine composition and/or the copper-promoting composition from an intravascular stent attached with the tetramine composition and/or the copper-promoting composition. In some embodiments, the tetramine composition and/or the copper-promoting composition is delivered to the ischemic injury site by a positive targeting liposome or an acceptor-donor complex. In some embodiments, the tetramine composition and/or the copper-promoting composition is delivered to the ischemic injury site using physicotherapeutics, ultrasound, iontophoresis, ultrasound penetration enhancement, electroporation, and/or sponge application. Application of the tetramine composition and/or cells to the ischemic injury site may be topical (e.g., through the skin), may be to some location at the injured tissue that is interior to the body surface, or both. For example, the tetramine composition and/or the copper-promoting composition may be delivered via iontophoresis through the blood vessel, an endothelial cell layer, or other interior tissues, to the ischemic injury site to provide an effective local concentration of the tetramine composition and/or the copper-promoting composition for tissue repair.

In some embodiments, a sustained release composition disclosed herein comprises a biodegradable polymer for controlled delivery of the tetramine composition and/or the copper-promoting composition. Suitable biodegradable polymers typically include polylactides (PLA), polyglycolides (PGA), poly(lactide-co-glycolide) (PLGA), poly(ε-caprolactone) (PCL), polyglyconate, polyanhydrides, polyorthoesters, poly(dioxanone), and polyalkylcyanoacrylates. In some embodiments, the sustained release composition comprises injectable biodegradable microspheres such as PLGA microspheres, PCL microspheres, polyanhydride microspheres, polyorthoesters microspheres, and polyalkylcyanoacrylate microspheres.

In particular embodiments, a range of types of copper-containing compound can be used for localized delivery of the copper-promoting composition directly to an ischemic injury site. Examples of suitable copper ion-containing solutions are copper (I) chloride, copper (II) chloride, copper acetate, and copper sulfate solutions. In some embodiments, copper forms a compound or complex with a protein, peptide, amino acid, mono-, di-, or polysaccharide, one or more polymers, or a small molecule, and the compound or complex is used for direct localized delivery at the ischemic injury site. In some embodiments, an organometallic compound containing the copper ion is used for direct localized delivery at the ischemic injury site.

In some embodiments, the concentration of copper ions in the copper-promoting composition used for localized delivery directly to an injury site is from about 5 μM to about 10 μM, about 10 μM to about 20 μM, about 20 μM to about 40 μM, about 40 μM to about 60 μM, about 60 μM to about 80 μM, about 80 μM to about 100 μM, about 100 μM to about 200 μM, about 200 μM to about 400 μM, about 400 μM to about 600 μM, about 600 μM to about 800 μM, about 800 μM to about 1 mM, about 1 mM to about 5 mM, about 5 mM to about 10 mM, about 10 mM to about 20 mM, about 20 mM to about 40 mM, or about 40 mM to about 60 mM. The concentration of the copper ion may be determined during pre-clinical trials and clinical trials by methods familiar to physicians and clinicians.

Copper and Copper Chelating Tetramines

The terms "copper", "copper ion" and "copper element" are used herein interchangeably. In biological systems, copper ions usually exist in two oxidation states, cuprous ($Cu^{1+}$, copper (I), or reduced) state, and cupric ($Cu^{2+}$, copper (II), or oxidized) state. In some embodiments, the copper includes both cuprous and cupric states. In some embodiments, the copper is the cupric state ($Cu^{2+}$). In some embodiments, the copper is the cuprous state ($Cu^{1+}$). In some embodiments, the copper is a free ion, i.e. not bound or in a complex with another molecule, such as a protein or a small organic molecule. In some embodiments, the copper is in a salt form. In some embodiments, the copper is present as a salt selected from copper sulfate, copper chloride, copper oxide, copper gluconate, and copper amino acid chelates. In some embodiments, the copper is present as a complexed ion. In some embodiments, the copper is in an organometallic compound, such as a small molecule organometallic compound. In some embodiments, the copper is in a complex with a copper chelating tetramine. In some embodiments, the copper is a complex ion including the various species of ions resulting from introducing copper into a cell, tissue, or organism according to the present disclosure. In some embodiments, the copper forms a compound or complex with a protein, peptide, amino acid, or mono-, di-, or polysaccharide. Important copper binding proteins found in biological systems include, but are not limited to, cytochrome c oxidase (CcO), copper-zinc superoxide dismutase (Cu, Zn-SOD), dopamine β-hydroxylase (DBH), prion protein (PrP), tyrosinase, X-linked inhibitor of apoptosis protein (XIAP), lysyl oxidase, metallothionein (MT), and ceruloplasmin. In some embodiments, the copper is in a form not available for uptake or use by an ischemic tissue, such as in a complex with ceruloplasmin. In some embodiments, the copper is in a form available for uptake or use by an ischemic tissue. In some embodiments, the copper disclosed herein is an inducer of HIF-1 transcriptional activity.

A copper-promoting composition comprising any copper ion species described above may be used in the methods described herein. In some embodiments, the copper-promoting composition comprises a $Cu^{2+}$. In some embodiments, the copper-promoting composition comprises a $Cu^{1+}$. In some embodiments, the copper-promoting composition comprises a copper ion in a salt form (such as anyone or combination selected from copper sulfate, copper chloride, copper oxide, copper gluconate, and copper amino acid chelates). In some embodiments, the copper-promoting composition comprises an organometallic compound. In some embodiments, the copper-promoting composition does not comprise a copper ion or a copper compound.

"Copper level" referred by any of the methods described herein may refer to the concentration of any one of the copper species described above, such as $Cu^{2+}$, $Cu^{1+}$ or the concentration of the total copper (e.g. $Cu^{1+}$ and $Cu^{2+}$, and/or free or bound copper). In some embodiments, the copper level refers to the level of the cupric state. In some embodiments, the copper level refers to the level of copper that is in a form available for uptake or use by an ischemic tissue.

"Copper chelating tetramine" refers to a copper binding or chelating tetramine compound. In some embodiments, the copper chelating tetramine binds to $Cu^{2+}$. In some embodiments, the copper chelating tetramine binds to $Cu^{1+}$. In some embodiments, the copper chelating tetramine is specific (i.e. with higher affinity to) for $Cu^{2+}$ over $Cu^{1+}$. In some embodiments, the copper chelating tetramine forms a complex with a copper ion in a square-planar, distorted square-planar, trigonal-pyramidal, square-pyramidal, or distorted octahedral conformation. In some embodiments, the copper chelating tetramine alters the equilibrium between $Cu^{1+}$ and $Cu^{2+}$ in cells or organisms. In some embodiments, the copper chelating tetramine can change (such as decrease) the copper level (such as total copper level) in the individual. In some embodiments, the copper chelating tetramine can change (such as decrease) the copper level (such as total copper level) in the blood of the individual. In some embodiments, the copper chelating tetramine can increase the intracellular copper level (such as total or cupric copper level). In some embodiments, the copper chelating tetramine can increase the concentration of copper in a form available to an ischemic tissue in the individual. In some embodiments, the copper chelating tetramine can redirect the intracellular trafficking and/or inter-tissue or inter-organ transport of copper. In some embodiments, the copper chelating tetramine specifically binds to, and/or is uptaken by an ischemic tissue, such as an ischemic cardiac tissue. In some embodiments, the copper chelating tetramine (including its complex with copper) is permeable through the membrane. In some embodiments, the copper chelating tetramine (including its complex with copper) is liposoluble. In some embodiments, the stoichiometry of the copper chelating tetramine to copper in a complex thereof is about 1:1. In some embodiments, the copper chelating tetramine binds to copper ion reversibly. In some embodiments, the copper chelating tetramine binds to copper ion with a sufficiently low affinity inside cells at the ischemic tissue that allows unloading or dissociation of the copper ion.

Any copper chelating tetramine that can increase intracellular copper level may be used in the methods described herein. The copper chelating tetramine may refer to the compound themselves, pharmaceutically acceptable salts, active metabolites, derivatives, and prodrugs thereof, as well as stereoisomer, enantiomers, racemic mixtures, and the like wherever applicable. In some embodiments, the copper chelating tetramine is linear. In some embodiments, the copper chelating tetramine is branched. In some embodiments, the copper chelating tetramine is cyclic. In some embodiments, the copper chelating tetramine selected from triethylenetetramine (2,2,2-tetramine), 2,3,2-tetramine and 3,3,3-tetramine.

In some embodiments, the copper chelating tetramine is trientine. "Trientine" is also referred to as triethylenetetramine, 2,2,2-tetramine, N,N'-Bis(2-aminoethyl)-1,2-ethanediamine, 1,8-diamino-3,6-diazaoctane, 3,6-diazaoctane-1,8-diamine, 1,4,7,10-tetraazadecane, trien, TETA, TECZA, N,N'-Bis(aminoethyl)ethylenediamine, N,N'-Bis(2-aminoethyl)ethanediamine, and N,N'-Bis(2-aminoethyl)-ethylenediamine. In some embodiments, trientine is a compound of the formula: $NH_2(CH_2)_2NH(CH_2)_2NH(CH_2)_2NH_2$, or a pharmaceutically acceptable salt thereof.

Other copper chelating tetramines with similar copper chelating properties may include, but are not limited to, compounds of Formula (II), and pharmaceutically acceptable salts thereof:

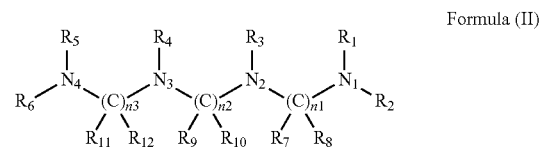

Formula (II)

In some embodiments, the copper chelating tetramine is an acyclic compound of Formula (II), wherein R1, R2, R3, R4, R5 and R6 are independently chosen from H, $CH_3$, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, and n3 are independently chosen to be 2 or 3; and, R7, R8, R9, R10, R11, and R12 are independently chosen from H, $CH_3$, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R1, R2, R3, R4, R5, or R6 may be functionalized for attachment, for example, to peptides, proteins, polyethylene glycols and other such chemical entities in order to modify the overall pharmacokinetics, deliverability and/or half-lives of the constructs. Examples of such functionalization include but are not limited to C1-C10 alkyl-CO-peptide, C1-C10 alkyl-CO-protein, C1-C10 alkyl-CO-PEG, C1-C10 alkyl-NHpeptide, C1-C10 alkyl-NH-protein, C1-C10 alkyl-NH—CO-PEG, C1-C10 alkyl-S-peptide, C1-C10 alkyl-S-protein. Furthermore, one or several of R7, R8, R9, R10, R11, or R12 may be functionalized for attachment, for example, to peptides, proteins, polyethylene glycols and other such chemical entities in order to modify the overall pharmacokinetics, deliverability and/or half-lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

In some embodiments, the copper chelating tetramine is a cyclic compound of Formula (II), wherein R1 and R6 are joined together to form the bridging group $(CR13R14)_{n4}$, and wherein R2, R3, R4, and R5 are independently chosen from H, $CH_3$, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-05 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, and n3 are independently chosen to be 2 or 3; and, R7, R8, R9, R10, R11, R12, R13 and R14 are independently chosen from H, $CH_3$, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-05 alkyl heteroaryl, C1-C6 alkyl fused aryl. In addition, one or several of R2, R3, R4, or R5 may be functionalized for attachment, for example, to peptides, proteins, polyethylene glycols and other such chemical entities in order to modify the overall pharmacokinetics, deliverability and/or half-lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, C1-C10 alkyl-S-protein. Furthermore, one or several of R7, R8, R9, R10, R11, R12, R13 and R14 may be functionalized for attachment, for example, to peptides, proteins, polyethylene glycols and other such chemical entities in order to modify the overall pharmacokinetics, deliverability and/or half-lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

"Pharmaceutically acceptable salts" refers to salts prepared from pharmaceutically acceptable non-toxic bases or acids including inorganic or organic bases and inorganic or organic acids the like. When a compound is basic, for example, salts may be prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In some embodiments, the pharmaceutically acceptable salts of the copper chelating tetramine is selected from hydrochloride salt (e.g., triethylenetetramine dihydrochloride), succinate salt (e.g., triethylenetetramine disuccinate), maleate salt (e.g., triethylenetetramine tetramaleate), and fumarate salt (e.g., triethylenetetramine tetrafumarate). The copper chelating tetramine, such as trientine, may also be in the form of quarternary ammonium salts in which the nitrogen atom carries a suitable organic group such as an alkyl, alkenyl, alkynyl or aralkyl moiety. Metabolites of the copper chelating tetramine may include, but are not limited to, acetylated metabolites, such as N-acetyl triethylenetetramine (e.g., monoacetyl-triethylenetetramine). Derivatives of the copper chelating tetramine may include, but are not limited to, PEG-modified tetramines (such as trientine-PEG).

The copper chelating tetramine, including trientine, may be prepared using any of a variety of chemical synthesis, isolation, and purification methods known in the art. For example, see U.S. Pat. Nos. 4,806,517, 4,550,209, 5,225,599, 4,766,247, European Patent No. EP262562, U.S. Pat. No. 8,394,992, and U.S. Pat. Publication No. US20130108709 A1.

Individual Having Ischemic Tissue Injury

"Ischemic tissue injury" described herein refers an injury of a tissue, including, for example cardiovascular, liver, brain, skeletal muscle, and the like, which result in a restriction in blood supply to the tissue, causing a shortage of oxygen and glucose needed for cellular metabolism in the tissue. The injury may involve any of a number of pathological conditions or trauma by an external force resulting in disturbance of blood flow. In some embodiments, the ischemic tissue injury is cardiovascular ischemia. In some embodiments, the ischemic tissue injury is cerebral ischemia or ischemic stroke. In some embodiments, the ischemic tissue injury is limb ischemia, such as lower limb ischemia. In some embodiments, the ischemic tissue injury is bowel ischemia, such as ischemic colitis or mesenteric ischemia. In some embodiments, the ischemic tissue injury is cutaneous ischemia. In some embodiments, the ischemic tissue injury is associated with embolism, thrombosis, aneurysm, trauma, myocardial infarction, mitral valve disease, chronic atrial fibrillation, cardiomyopathy, prosthesis, thoracic outlet syndrome, atherosclerosis, hypoglycemia, tachycardia, hypotension, tumor compression of a blood vessel, Sickel cell disease, frostbite, arteriovenous malformation, peripheral artery occlusive disease, rupture of significant blood vessels, anemia, diabetes, diabetic foot ulcers, necrotizing enterocolitis, ulcerative colitis, Crohn's disease, inflammatory bowel disease, restenosis (post-angioplasty or stent implantation), or pancreatitis. In some embodiments, the ischemic tissue injury is associated with cardiomyopathy. In some embodiments, the ischemic tissue injury is associated with myocardial infarction. In some embodiments, the ischemic tissue injury is associated with diabetes.

The methods described herein are therefore generally applicable to many diseases that involve ischemic tissue injury. These include, but are not limited to: myocardial infarction, cardiomyopathy, aneurysm, angina, aortic stenosis, aortitis, arrhythmias, arteriosclerosis, arteritis, asymmetric septal hypertrophy (ASH), atherosclerosis, atrial fibrillation and flutter, bacterial endocarditis, Barlow's Syndrome (mitral valve prolapse), bradycardia, Buerger's Disease (thromboangiitis obliterans), cardiomegaly, carditis, carotid artery disease, coarctation of the aorta, congenital heart defects, congestive heart failure, coronary artery disease, Eisenmenger's Syndrome, embolism, endocarditis, erythromelalgia, fibrillation, fibromuscular dysplasia, heart block, heart murmur, hypertension, hypotension, idiopathic infantile arterial calcification, Kawasaki Disease (mucocutaneous lymph node syndrome, mucocutaneous lymph node disease, infantile polyarteritis), metabolic syndrome, microvascular angina, myocarditis, paroxysmal atrial tachycardia (PAT), periarteritis nodosa (polyarteritis, polyarteritis nodosa), pericarditis, peripheral vascular disease, critical limb ischemia, phlebitis, pulmonary valve stenosis (pulmonic stenosis), Raynaud's Disease, renal artery stenosis, renovascular hypertension, rheumatic heart disease, diabetic vasculopathy, septal defects, silent ischemia, syndrome X, tachycardia, Takayasu's Arteritis, Tetralogy of Fallot, transposition of the great vessels, tricuspid atresia, truncus arteriosus, valvular heart disease, varicose ulcers, varicose veins, vasculitis, ventricular septal defect, Wolff-Parkinson-White Syndrome, endocardial cushion defect, acute rheumatic fever, acute rheumatic pericarditis, acute rheumatic endocarditis, acute rheumatic myocarditis, chronic rheumatic heart diseases, diseases of the mitral valve, mitral stenosis, rheumatic mitral insufficiency, diseases of aortic valve, diseases of other endocardial structures, ischemic heart disease (acute and subacute), angina pectoris, acute pulmonary heart disease, pulmonary embolism, chronic pulmonary heart disease, kyphoscoliotic heart disease, myocarditis, endocarditis, endomyocardial fibrosis, endocardial fibroelastosis, atrioventricular block, cardiac dysrhythmias, myocardial degeneration, cerebrovascular disease, a disease of arteries, arterioles and capillaries, or a disease of veins and lymphatic vessels; an acquired brain injury, traumatic brain injury, stroke (including ischemic, intracerebral hemorrhagic, subarachnoidal hemorrhagic), anoxic injuries, metabolic disorders, encephalitis, and brain injuries due to infection. In certain embodiments, diseases that involve ischemic tissue injury include systemic sarcoidosis, a cutaneous disease or condition, Lofgren's syndrome, a pulmonary disease or condition, a cardiac disease or condition, an ocular disease or condition, a hepatic disease or condition, a musculoskeletal disease or condition, and a renal disease or condition. The present application thus also comprises treatment of any of the diseases using methods described herein.

An "individual", "subject" or "patient" described herein refers to a mammal such as mice, rats, rabbits, cats, dogs, pigs, cows, ox, sheep, goats, horses, monkeys and other non-human primates, and humans, a vertebrate such as fish, and a bird such as chicken. Mammals can include farm animals, sport animals, rodents, and pets. In some embodiments, the individual is human.

The methods described herein are applicable to an individual having one or more ischemic tissue injuries, including, but not limited to: ischemic myocardial injury, ischemic brain injury, ischemic spinal cord injury, ischemic muscular injury, ischemic skeletal injury, acute tubular necrosis, ischemic bowel injury, ischemic lung injury, ischemic liver injury, ischemic kidney injury, ischemic skin injury, hernia, vascular anastomoses, atherosclerotic plaque, hemangioma, and after blunt or penetrating traumatic injury.

In some embodiments according to any of the methods described herein, the individual does not have a compromised tissue repair system. In some embodiments, the individual has a compromised tissue repair system. Individuals with a compromised tissue repair system may have one or more of the following characteristics: (a) old age (such as at least about 60 years old, including, for example, at least about any of 65, 70, 75, 80, 85, 90, or more years old); (b) chronic tissue injury (such as an individual that has had tissue injury for at least about any of 6, 7, 8, 9, 10, 11, 12, 18, or 24 months); (c) deficiency in stem cells; (d) deficiency in the migration (i.e. homing) of stem cells; (e) a defective tissue repair system; and (f) one or more of the following symptoms or conditions: loss of memory, low or reduced locomotive ability (including but not limited to force ability, speed endurance, flexibility, and joint movability), hypoaesthesia, muscle weakness, hearing loss, and chronic strain.

In some embodiments, the individual is at least about any one of 20, 30, 40, 50, 60, 70, 80, or more years old. In some embodiments, the individual is younger than about any one of 20, 30, 40, 50, 60, 70, 80 years old. In some embodiments, the individual has chronic ischemia. In some embodiments, the individual has efflux of copper from the ischemic tissue (such as ischemic myocardium) to the blood circulation. In some embodiments, the individual has decreased level (less than about any of 1%, 5%, 10%, 20%, 30%, 40%, 50%, 60%, 70%, 80%, or 90%) of copper in the ischemic tissue. In some embodiments, the decreased level of copper in the ischemic tissue is caused by chronic ischemic conditions. In some embodiments, the individual has repressed HIF-1 transcriptional activity.

In some embodiments, the individual is selected for treatment based on his or her copper level, such as intracellular copper level, extracellular copper level, total copper level, and copper level in the serum (i.e. blood). Individuals under chronic ischemic conditions usually have low intracellular copper level in the ischemic tissue, such as less than about any of 90%, 80%, 70%, 60%, 50%, 40%, 30%, 20%, 10%, or less of the average intracellular copper level of the corresponding tissue in healthy individuals. The copper level in the serum, such as total copper level in the serum, level of protein (e.g. ceruloplasmin)-bound copper in the serum, or free (i.e. unbound) copper in the serum, for individuals under chronic ischemic conditions is usually higher (such as about any of 1.2 times, 1.5 times, 1.75 times, 2 times, 3 times, 4 times, 5 times, or more) than the average copper level in the serum of healthy individuals. In some embodiments, prior to the administration of the tetramine composition the individual has at least about any of 60 ↑g/dL, 70 µg/dL, 80 µg/dL, 90 µg/dL, 100 µg/dL, 110 µg/dL, 120 µg/dL, 130 µg/dL, 140 µg/dL, 150 µg/dL, 175 µg/dL, 200 µg/dL, 250 µg/dL, 300 µg/dL or more of total copper level in the serum. In some embodiments, prior to the administration of the tetramine composition, the individual has no more than about any of 1 time, 1.2 times, 1.5 times, 1.75 times, or 2 times of average total copper level in the serum of healthy individuals. In some embodiments, prior to the administration of the tetramine composition the individual has no more than about any of 60 µg/dL, 70 µg/dL, 80 µg/dL, 90 µg/dL, 100 µg/dL, 110 µg/dL, 120 µg/dL, 130 µg/dL, 140 µg/dL, 150 µg/dL, 175 µg/dL, 200 µg/dL, 250 µg/dL, 300 µg/dL of total copper level in the serum. In some embodiments, upon administration of the tetramine composition, the individual has at least about any of 50%, 60%, 70%, 80%, 90%, or more of average total copper level in the serum of healthy individuals. In some embodiments, upon administration of the tetramine composition, the individual has at least about any of 60 µg/dL, 70 µg/dL, 80 µg/dL, 90 µg/dL, 100 µg/dL, 110 µg/dL, 120 µg/dL, 130 µg/dL, 140 µg/dL, or 150 µg/dL of total copper level in the serum.

In some embodiments, the individual is selected for treatment based on his or her HIF-1 activity level. In some embodiments, the individual has repressed transcriptional activity of HIF-1 target genes in the ischemic tissue. In some embodiments, the individual has high level (such as protein or RNA level) of HIF-1α in the ischemic tissue, but repressed transcriptional activity of HIF-1 target genes in the ischemic tissue. In some embodiments, the individual has chronic ischemia that results in repressed HIF-1 activity.

Kits, and Articles of Manufacture

The present application also provides kits, medicines, compositions, and unit dosage forms for use in any of the methods described herein.

Kits provided herein include one or more containers comprising any one of the tetramine compositions (including pharmaceutical compositions) described herein and/or other agent(s), and in some embodiments, further comprise instructions for use in accordance with any of the methods described herein. The kit may further comprise a description of selection of individual suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a) a tetramine composition comprising a copper chelating tetramine (such as trientine) or a pharmaceutically acceptable salt thereof and a pharmaceutically acceptable carrier; and optionally b) instructions for administering the tetramine composition for treatment of a disease or condition associated with ischemic tissue injury.

In some embodiments, the kit comprises a) a tetramine composition comprising a copper chelating tetramine (such as trientine) or a pharmaceutically acceptable salt thereof and a pharmaceutically acceptable carrier; b) a copper-promoting composition comprising a copper ion (such as $CuSO_4$ or $CuCl_2$) and a pharmaceutically acceptable carrier; and optionally c) instructions for administering the tetramine composition and the copper-promoting composition for treatment of a disease or condition associated with ischemic tissue injury.

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

In some embodiments, the kits comprise one or more components that facilitate delivery of the tetramine composition, the copper-promoting composition, and/or additional therapeutic agents to the individual. For example, in some embodiments, the kit comprises components that facilitate intralesional delivery of the tetramine composition, and/or the copper-promoting composition to the individual. In some embodiments, the kit comprises, e.g., syringes and needles suitable for delivery of cells to the individual, and the like. In such embodiments, the tetramine composition, and/or the copper-promoting composition may be contained in the kit in a bag, or in one or more vials. In some embodiments, the kit comprises components that facilitate intravenous or intra-arterial delivery of the tetramine composition, and/or the copper-promoting composition to the individual. In some embodiments, the tetramine composition, and/or the copper-promoting composition may be contained, e.g., within a bottle or bag (for example, a blood bag or similar bag able to contain up to about 1.5 L solution comprising the cells), and the kit further comprises tubing and needles suitable for the delivery of the tetramine composition, and/or the copper-promoting composition to the individual.

The instructions relating to the use of the compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of the copper chelating tetramine as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the pharmaceutical compositions and instructions for use and packaged in quantities sufficient for storage and use in pharmacies, for example, hospital pharmacies and compounding pharmacies.

Also provided are medicines, compositions, and unit dosage forms useful for the methods described herein.

The following non-limiting examples further illustrate the compositions and methods of the present invention. Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1: Crystal Structure of a Complex of Trientine and a Copper Ion

A complex comprising trientine dichloride, a copper ion, and water, was crystallized. A suitable single crystal (150116_s2_1zh_m) was selected and X-ray diffraction data was collected using the single crystal on a Xcalibur Eos diffractometer. The crystal was kept at 143.00-143.10 K during data collection. Using Olex2 (Dolomanov et al., (2009) *J. Appl. Cryst.* 42: 339-341), the structure was solved with the Superflip (Palatinus et al., (2008) *J. Appl. Cryst.* 41: 975-984; Palatinus et al., (2012) *J. Appl. Cryst.* 45: 575-580) structure solution program using Charge Flipping and refined with the ShelXL (Sheldrick G. M. (2008) *Acta Cryst.* A64: 112-122) refinement package using Least Squares minimization algorithm. The empirical formula of the complex in each unit cell was determined to be $C_6H_{20}Cl_2CuN_4O$. The refined crystal structure and its parameters are shown in FIGS. 1-3 and 4A-4C.

Figure 5:
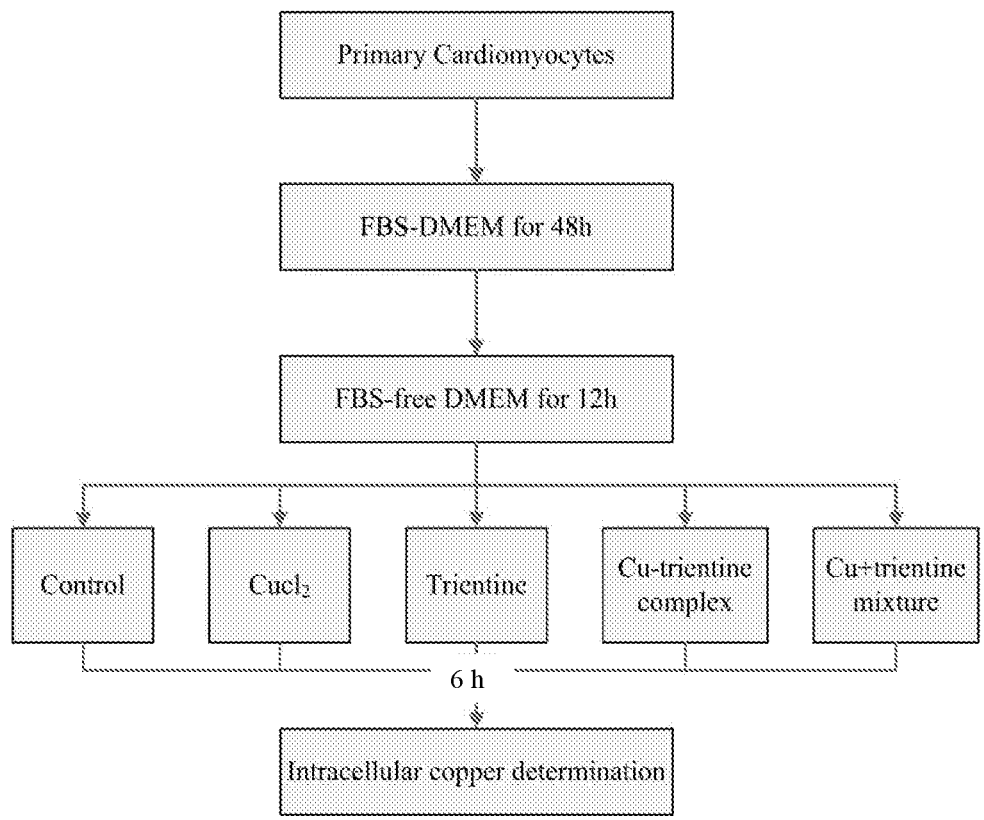
FIG. 5 shows a flow chart of the experimental procedure of Example 2.

Example 2: Intracellular Delivery of Copper to Cardiomyocytes by Trientine and Trientine-Copper Complex This example describes an in vitro copper delivery assay to cardiomyocytes by trientine and trientine-copper complex. A flowchart of the experimental procedure is shown in FIG. 5.

Primary cultures of neonatal rat cardiomyocytes were cultured in serum-free Dulbecco's modified Eagle medium (DMEM) supplemented with 10% Fetal Bovine Serum (FBS) at 37° C., 10% $CO_2$ for 48 hours. The cells were then transferred to serum-free DMEM and cultured at 37° C., 10% $CO_2$ for 12 hours, before the cells were divided into five experimental groups (one control group, and four treatment groups). In the control group, the cells were cultured with serum-free DMEM for an additional 6 hours at 37° C., 10% $CO_2$. In the four treatment groups, the cells were incubated for 6 hours at 37° C., 10% $CO_2$ with $CuCl_2$ alone, trientine alone, a trientine-copper complex, and a mixture of trientine and $CuCl_2$ respectively, each at a final concentration of 10 μM of trientine and/or 10 μM of copper. The trientine-copper complex was synthesized in house and characterized by mass spectrometry and x-ray diffraction (XRD). The trientine-copper complex had a composition and structure as described in Example 1. The mixture of trientine and copper was prepared by adding equal moles of trientine and $CuCl_2$ to serum-free DMEM at a final concentration of 10 μM at 37° C. for 24 hours before the mixture was used to treat neonatal rat cardiomyocytes.

After treatment, cells were collected by a cell scraper, washed three times with ice-cold PBS containing 10 mM EDTA (Sigma, USA) to ensure that extracellular copper was completely removed, and centrifuged at 3000 rpm for 5 minutes. Cell pellets were lysed using 1% SDS solution (Beyotime, CN). Lysates were divided into two parts. One part was digested with concentrated nitric acid at 50° C. for 72 hours and analyzed using a graphite furnace atomic absorption spectrophotometer to assess the intracellular copper concentration. Another part was used to determine the total protein concentration by the Bicinchoninic Acid (BCA) Protein Assay (Bio-Rad, USA). The intracellular copper concentration of each treatment group was normalized to the total protein concentration.

Figure 6:
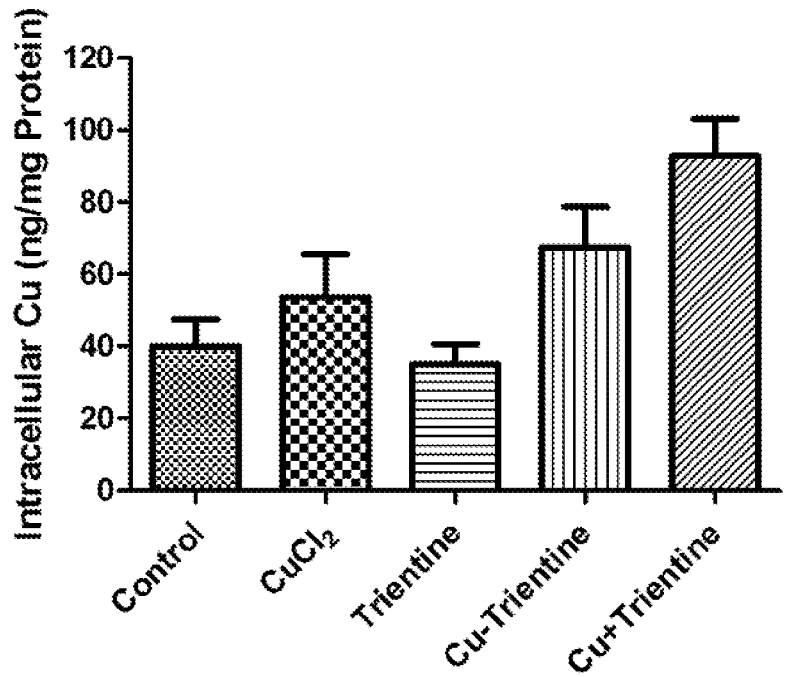
FIG. 6 shows intracellular copper concentrations of primary neonatal rat cardiomyocytes in different experimental groups of Example 2.

FIG. 6 shows the normalized intracellular copper concentrations of the five experimental groups. All data were expressed as means±Standard Deviation (SD). One-way analysis of variance was used for initial analysis, and Student-Newman-Keuls was employed for comparison among multiple groups. The differences among the experimental groups were considered to be significant at $P<0.05$. As shown in FIG. 6, the intracellular copper concentration of the trientine-copper complex (i.e. Cu–Trientine) treatment group and the treatment group with the mixture of trientine and $CuCl_2$ (i.e. Cu+Trientine) increased significantly as compared to the control group, and the increase in the intracellular copper concentrations in these two groups was more pronounced than the $CuCl_2$ treatment alone. Notably, the mixture of trientine and $CuCl_2$ (i.e. Cu+Trientine) led to the largest increase in the intracellular copper concentration among all conditions tested, suggesting that trientine could shuttle copper from a cellular environment with high copper level into cardiomyocytes.

Example 3. Trientine Therapy in a Rat Model of Pathologic Cardiac Hypertrophy

Figure 7:
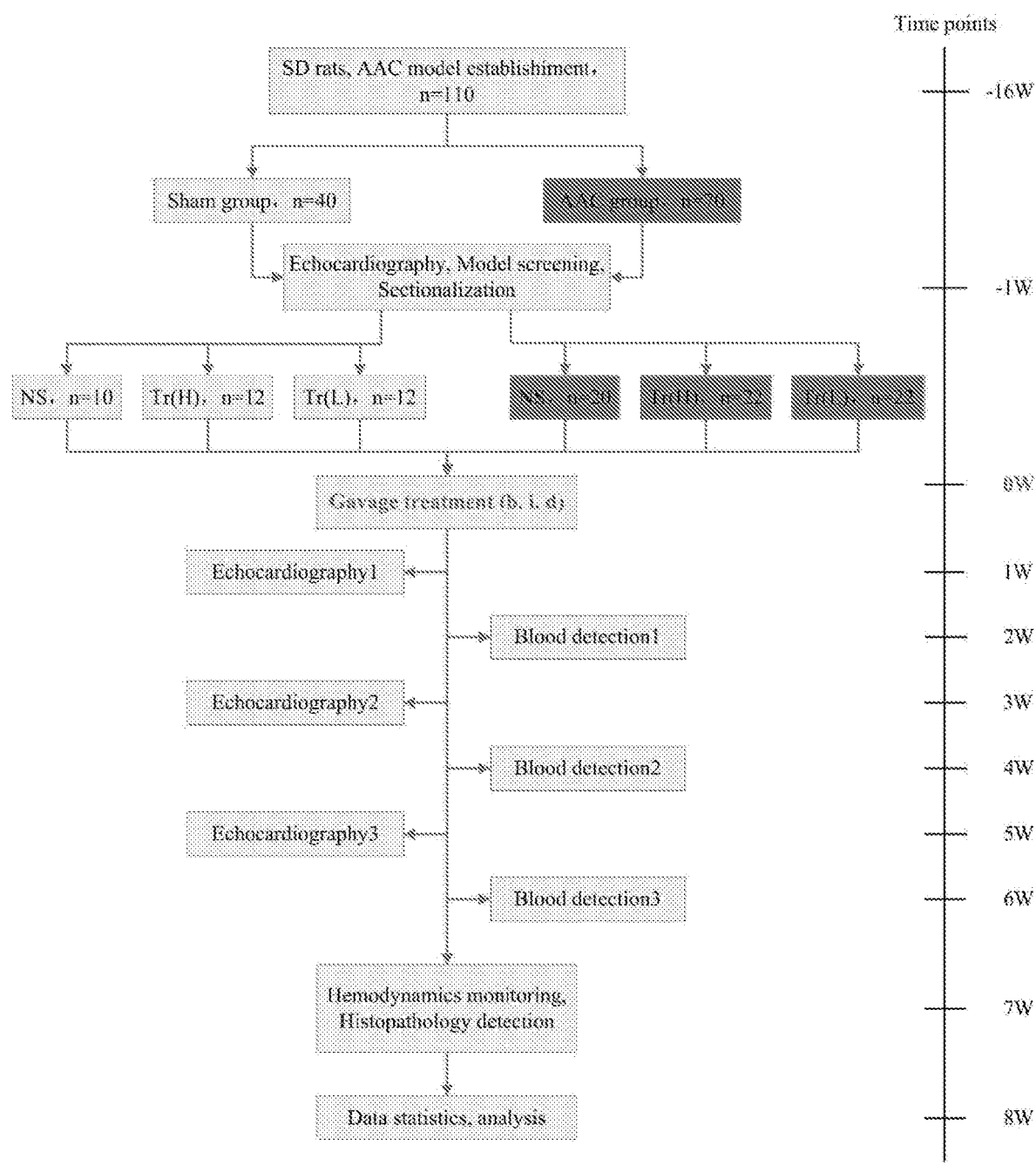
FIG. 7 shows a flow chart of the experimental procedure of Example 3.

This example describes an in vivo experiment for assessing efficacy of the trientine therapy in Sprague-Dawley rats with pathologic cardiac hypertrophy. The rat model of pathologic cardiac hypertrophy was established by an ascending aortic constriction operation. FIG. 7 shows a flowchart of the experimental procedure.

1.1 Establishment of Pathologic Cardiac Hypertrophy in Rats

Prior to the surgical procedure, all subjects received an intraperitoneal injection of 10% chloral hydrate (0.35 mg/kg) to induce sedation. Hair covering the left chest was shaved thoroughly for the operation. Endotracheal intubation was introduced for ventilation. Assisted respiration was conducted to achieve tidal volume between 1.2 mL to 1.5 mL. The respiratory rate was nearly 80/min, and the inspiratory/expiratory ratio was 1:1.

During the operation, the position of the rat was adjusted to the right lateral decubitus, and the rat was placed under a stereomicroscope. The operating area was isolated in an aseptic manner. The isolation was done with one piece of disposable sterile drape.

Surgical area was cut slightly medial to the line of the left second intercostal space, and a 1-1.5 cm transverse incision was made outward from the left side of the presternum. The subcutaneous tissue and the muscular planes were dissected down to the pleura, entering the pleural space. A cotton bud was inserted to sweep the pleural space and push the lung away from the operation field to avoid lung injury, and then the intercostal incision was widened with a retractor to open the chest and to expose the thymus and fat.

After the thymus and fat were pulled away, the major vessels were exposed in the upper part of the left atrial appendage. The ascending portion of the aorta was dissected from the pulmonary trunk on the right. The constriction site was located on the ascending aorta between the aortic valve and the innominate artery.

The ascending aorta was constricted with a 20-gauge needle (O.D. 0.9 mm). The ascending aorta and the needle were tied using a single piece of 6-0 surgical thread. The needle was then immediately removed to provide a lumen with a stenotic aorta. After the constriction, the left ventricular and the left auricle swelled.

Before closing the chest, the chest retractor was removed, and the thymus and fat were moved back to its normal position. The chest cavity was closed by bringing together the second and third ribs with two 3-0 nylon sutures. To avoid hemorrhea and pneumothorax, care was taken to avoid piercing the dilated heart and damaging the lung during ribs suture. The lungs were reinflated by shutting off the outflow on the ventilator for 1-2 seconds using a finger while closing the intercostal incision, so that air could be expelled from the pleural cavity. After the intercostal incision was closed, the muscle and skin incisions were closed in layers with 5-0 silk sutures, and cleaned in a sterile manner. The endotracheal tube was retracted after spontaneous breathing was restored. To ameliorate pain after surgery, analgesic dezocine (0.8 mg/kg) was given intramuscularly and once daily for the next 2 days.

1.2 Echocardiography

The rats were sedated by intraperitoneal injection of 10% chloral hydrate (0.35 mg/kg) for echocardiography measurements. At 4 months after the aortic constriction operation and at 1, 3 and 5 weeks after the trientine treatment, a series of echocardiograms were performed using an 11.5-MHz transducer (Vivid 7 Dimension, GE). Interventricular septum depth (IVSD) and left ventricular posterior wall depth (LVPWD) were obtained using two-dimensional mode by taking measurements of the short-axis cross-sectional areas and the left ventricular length.

The ejection fraction (EF) and shortening fraction (FS) of the left ventricular were evaluated with the Simpson's single-plane method. Left-ventricular end-diastolic volume (LVEDV), end-systolic volume (LVESV), end-diastolic interior diameter ($LVID_d$) and end-systolic interior diameter ($LVID_s$) were directly recorded. EF and FS were calculated according to the following formulas: EF=(LVEDV−LVESV)/LVEDV×100%, FS=($LVID_d$−$LVID_s$)/$LVID_d$×100%

1.3 Trientine Treatment

Four months after the operations, left ventricular concentric hypertrophy and myocardial interstitial fibrosis were observed. Establishment of the pathologic cardiac hypertrophy model was confirmed by ultrasound evaluations of the cardiac morphology and functions. Trientine treatment was initiated after confirmation of the pathologic cardiac hypertrophy state. The aortic ascending constriction (AAC) group was divided into three groups: a control group (NS group) and two trientine treatment groups (Tr(H) group and Tr(L)

group). Rats in the sham group were subjected to the same surgical procedure except for the steps of the aortic ascending constriction. The sham group rats were also divided into three groups: a control group (NS group) and two trientine treatment groups (Tr(H) group and Tr(L) group). Rats in the control groups were treated with a saline solution. Trientine was administered orally twice a day in the trientine treatment groups. Two doses of trientine (dose calculated based on trientine dihydrochloride) were administered, 45 mg/kg/day (Tr(H) group) and 90 mg/kg/day (Tr(L) group). The treatment was continued for 6 weeks.

The experimental procedure and results in the following sections of the present example are focused on the treatment with a trientine composition that consists essentially of the trientine dihydrochloride. The same experimental protocol is used to assess therapeutic efficacy of other trientine compositions for treating cardiac hypertrophy in the rat model. For example, in one experiment, in addition to the trientine treatment, the ACC rats in the trientine treatment groups are further treated with an oral copper supplement (such as copper chloride) at a dose of 54 mg/kg daily for 6 weeks. In another experiment, the trientine-copper complex of Example 1 is used to treat the ACC rats in the trientine treatment group at a dosage of 120 mg/kg/day by oral administration for 6 weeks.

1.4 Cardiac Morphology and Function Evaluations

Cardiac morphology and functions were evaluated by echocardiography, and plasma copper concentrations were measured (i.e. blood detection) to assess therapeutic efficacy of the trientine treatments according to the schedule shown in FIG. 7.

Additionally, heart tissue sections are obtained from rats after they are sacrificed at the end of the experiments. Immunohistochemical experiments are carried out on the tissue sections. Capillary density of the heart tissue sections is determined, and the changes in collagen contents are detected. mRNA and protein levels of HIF-1α and its targets, such as VEGF and VEGFR-1, in the infarcted tissue, border zone of the infarcted tissue, and cardiac tissue remote from the infarcted area are measured.

1.5 Copper Concentration in Heart Tissue

Tissue samples were freshly frozen and stored at −80° C. before lyophilization. After lyophilization and digestion of the tissues with nitric acid, the sample was colorless or light yellow, and clear with no visible precipitate or residue. Ultrapure water was added to each vessel to dilute $HNO_3$ to 2% for subsequent analyses of copper concentrations. Copper concentrations were determined by graphite furnace atomic absorption spectrophotometry (ICE3500, Thermo) according to the program shown in Table 1 below.

TABLE 1

Graphite furnace atomic absorption spectrophotometry program

| | Time (s) | Argon Gas Flow (L/min) |
| --- | --- | --- |
| 90 | 20 | 0.2 |
| 120 | 20 | 0.2 |
| 850 | 20 | 0.2 |
| 2100 | 3 | 0 |
| 2500 | 3 | 0.2 |

1.6 Statistical Analysis

All data were expressed as means±SD. The variation of each parameter was compared among the various experimental groups using the homogeneity of Levene's test and coefficient of variance (CV). A SPSS 14.0 statistical package (SPSS, Chicago, Ill.) was used, and significant difference was called when P values were <0.05.

2. Results 2.1 Cardiac Morphology and Functions

Figure 8A:
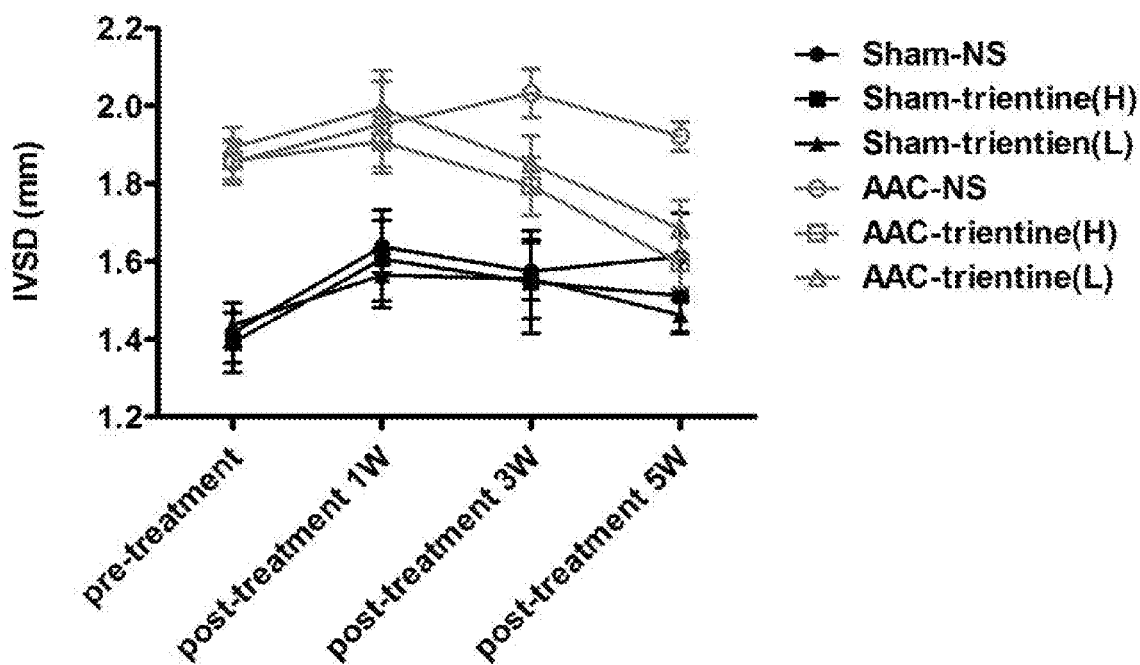
FIG. 8A shows echocardiography-detected morphological changes in the interventricular septum depth (IVSD) of rats in the ascending aortic constriction (AAC) and sham operation groups with or without trientine treatment.
Figure 8B:
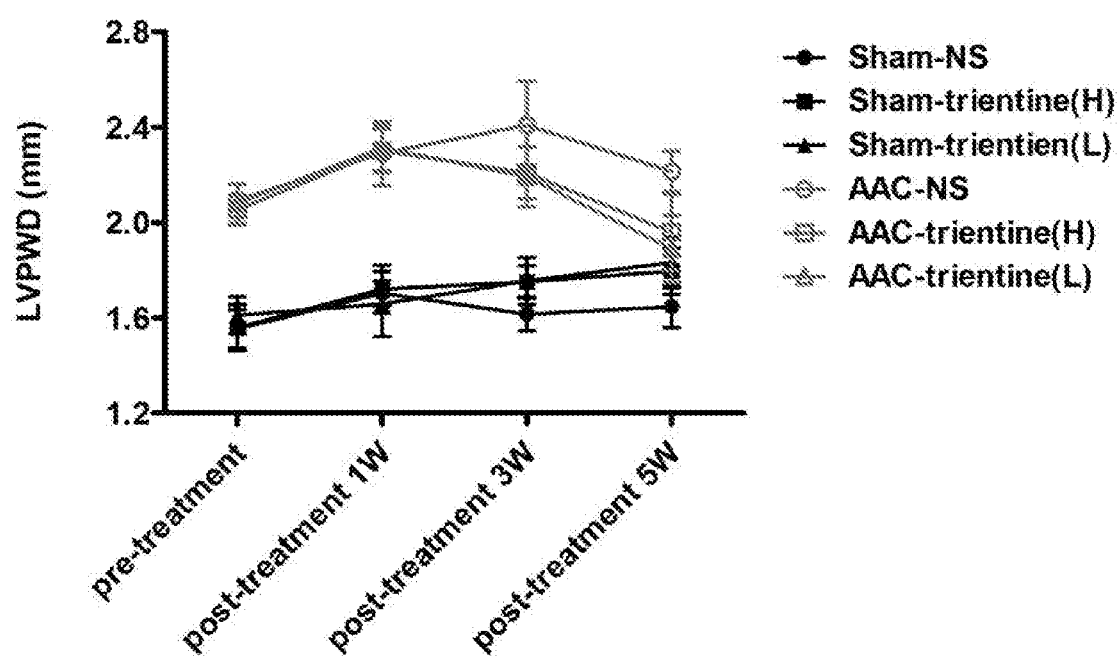
FIG. 8B shows echocardiography-detected morphological changes in the left ventricular posterior wall depth (IVPWD) of rats in the AAC and sham operation groups with or without trientine treatment.

Echocardiography examinations showed that, after trientine treatment, reversion of pathological cardiac hypertrophy occurred at the morphological level. After 3 weeks of treatment, the interventricular septum depth (IVSD) and left ventricular posterior wall depth (LVPWD) of the rats decreased significantly. With extension of the treatment time, the treatment effect of trientine became even more obvious. When the AAC rats were treated for 5 weeks, IVSD and LVPWD were nearly normal as compared to those of the sham groups. As shown in FIG. 8A and FIG. 8B, the treated groups showed a significantly downward trend in the IVSD and LVPWD values over time according to the continuous monitoring results. By contrast, in the control group, IVSD and LVPWD increased steadily with time.

Figure 9A:
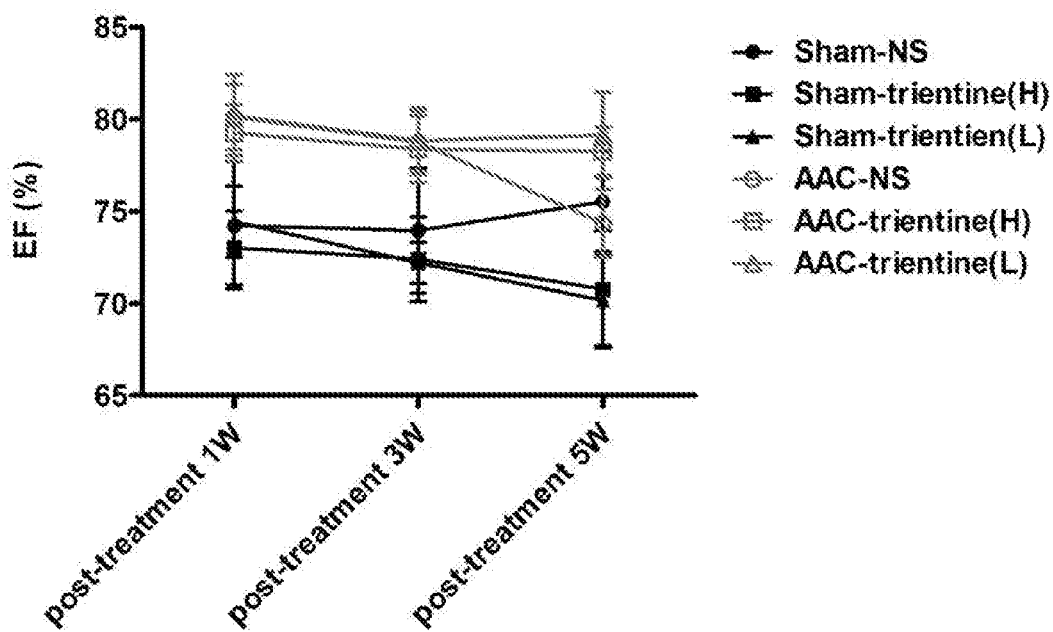
FIG. 9A shows echocardiography-detected functional changes in the left ventricular ejection fraction (EF) of rats in the AAC and sham operation groups with or without trientine treatment.
Figure 9B:
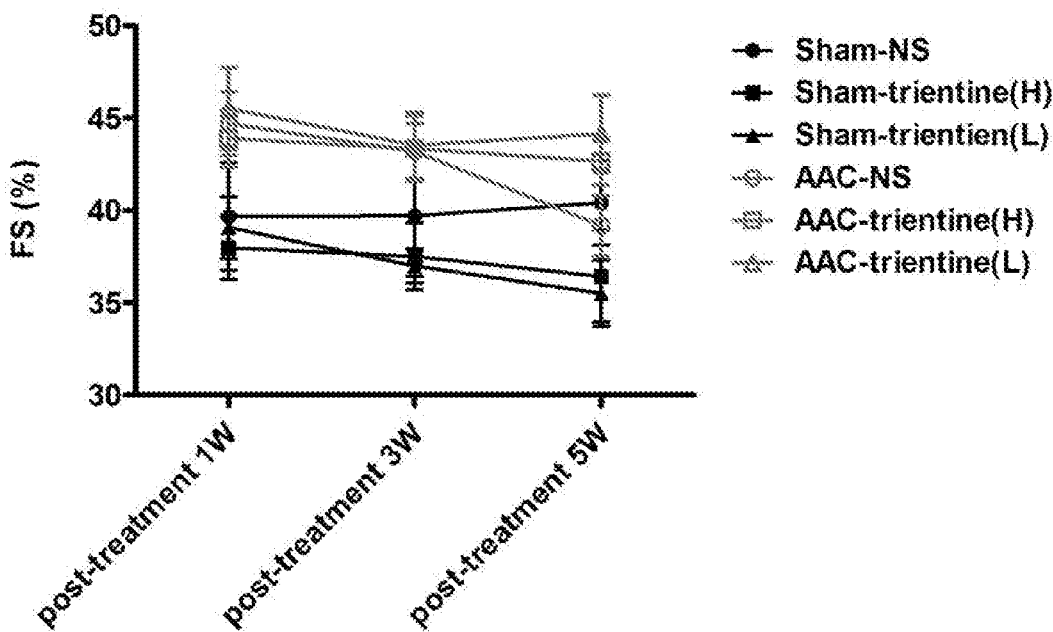
FIG. 9B shows echocardiography-detected functional changes in the left ventricular shortening fraction (FS) of the AAC and sham operation groups with or without trientine treatment.

Although the cardiac function parameters, ejection fraction (EF) and shortening fraction (FS), were within the normal range for all experimental groups because of compensatory effects, FIGS. 9A and 9B show that EF and FS of the trientine-treated groups did not fluctuate very significantly. By contrast, a significant downward trend of EF and FS was observed in the untreated groups.

Figure 10A:
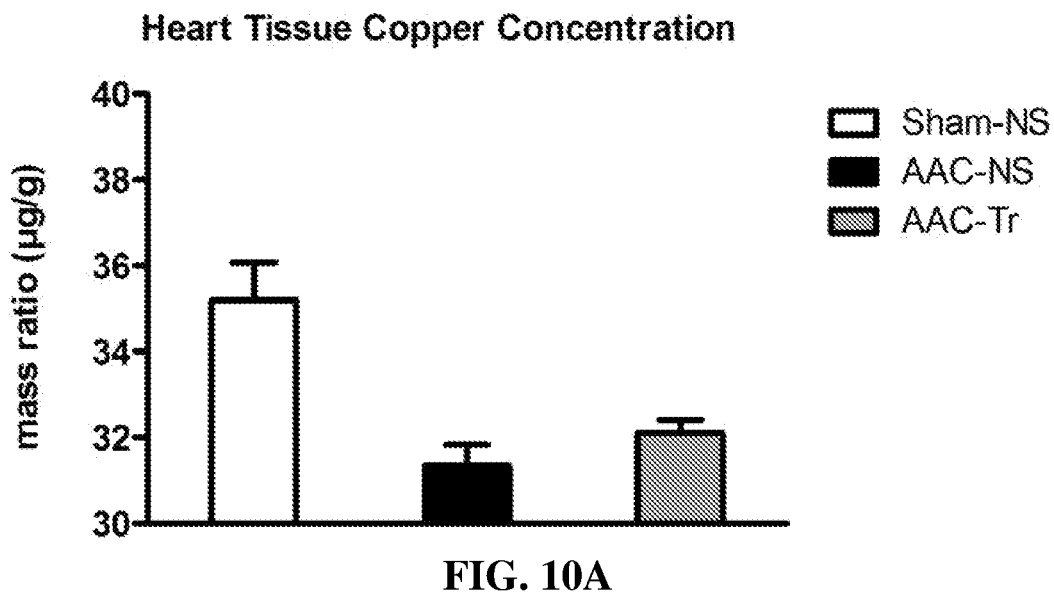
FIG. 10A shows average copper concentrations in the heart tissues of rats in the sham control group, and untreated and trientine-treated ACC groups.

Copper concentrations in the plasma and myocardium of rats of the various treatment groups were determined by atomic absorption spectrometry. As shown in FIG. 10A, copper concentrations decreased in the hypertrophic myocardium, when the rats were subjected to AAC operations. After trientine treatment for 6 weeks, the copper concentrations increased in the heart tissues of the treated rats. The bar in FIG. 10A corresponding to the AAC-Tr group shows the average copper concentration in the heart tissue of AAC rats treated with both high dose of trientine and low dose of trientine (i.e. AAC-Tr(H) and AAC-Tr(L) groups combined).

Figure 10B:
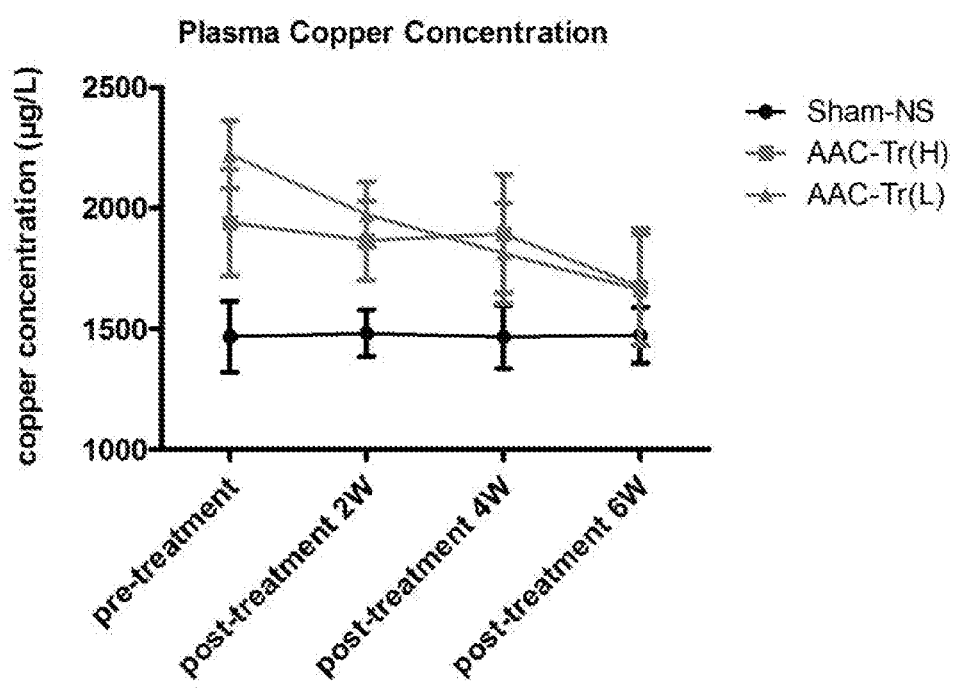
FIG. 10B shows average copper concentrations in the plasma of rats in the sham control group, and untreated and trientine-treated ACC groups. An initial high level of plasma copper concentration in the AAC rats was reduced by trientine treatment in both high-dosage trientine treated group (ACC-Tr(H)) and the low-dosage trientine treated group (ACC-Tr(L)).

As a consequence of the copper efflux from the heart tissues of the AAC rats, copper concentrations in the plasma of the AAC rats were higher than that of the rats in the sham group. However, after a 6-week treatment of trientine, according to measurements at different time points during the course of the treatment (i.e., every two weeks), the high copper concentration in the plasma of the AAC rats decreased significantly over time. By contrast, the plasma copper concentration of rats in the sham group remained quite stable over the course of the treatment (FIG. 10B).

3. Discussion

The present study used trientine to increase the copper concentration in hypertrophic heart tissues of rats. The results showed that trientine was able to promote tissue redistribution and reuse of copper, and to revert the morphology and functions of hypertrophic hearts. Transcriptional activities of HIF-1 and capillary density may also increase in the infarcted heart tissues as a result of trientine treatment in the cardiac hypertrophic rats. Furthermore, echocardiography examinations showed that normal cardiac functions were maintained throughout the trientine treatment. The results of this experiment provide strong evidence that the trientine treatment of the present invention can effectively deliver copper to ischemic cardiac tissues in vivo for treatment of cardiac hypertrophy.

Example 4. Trientine Therapy for a Rhesus Monkey Heart Failure Model after Myocardial Ischemic Infarction This example describes an in vivo experiment for assessing efficacy of trientine therapy in a Rhesus monkey model of heart failure. The Rhesus monkey has a higher-order heart resembling that of humans in terms of the internal structure, electrical activities, distribution of coronary arteries, coronary collateral circulation, and its placement and attachment in the thoracic cavity. Thus, the Rhesus monkey model of heart failure provides a good surrogate for evaluating efficacy of therapies for heart failure conditions in humans. In this experiment, myocardial ischemic infarction was established by a coronary artery ligation operation. After the operation, the ischemic cardiac tissue was gradually replaced by collagenous fiber and became an infarcted tissue. One year after the operation, the non-infarcted cardiac tissue in the animal became unable to compensate for the lost functions of the infarcted cardiac tissue, and a heart failure model was thus developed. Trientine treatment was subsequently provided to the monkeys to treat the heart failure.

1.1 Establishment of a Heart Failure in Rhesus Monkeys

Prior to the surgical procedure, all subjects received an intramuscular injection of 5 mg/kg ketamine and 0.2 mg/kg midazolam to induce sedation. Hair covering chest and limbs at electrode attachment sites was shaved thoroughly for the operation and to improve electrocardiography (ECG) recording results. The standard bipolar and unipolar limb leads were recorded. Animals displaying abnormal ECG, such as tachycardia (more than 200 beats per minute), arrhythmia, and obvious ST segment deviations from the base line were excluded from this study.

Standard noninvasive measurements including electrocardiogram, cuff blood pressure, pulse oximetry, and capnography were constantly monitored (Dash3000, GE, USA.), and vein catheters were established in the subjects. All of the monkeys subjected to the surgical procedure were firstly intubated after anesthesia induced by intravenous infusion of fentanyl (10 µg/kg), midazolam (0.2 mg/kg), propofol (1 mg/kg), and vecuronium (0.1 mg/kg). Assisted respiration was conducted with pressure-controlled ventilation to achieve end-tidal $CO_2$ between 35 mmHg to 40 mmHg. Inspiratory pressure was set within a range from 12 to 20 cm $H_2O$. The respiratory rate was 40/min, and the inspiratory/expiratory ratio was 1:2.

In order to maintain the anesthetic conditions during the surgical procedure, 2 mL of fentanyl (0.1 mg) and 10 mL of propofol (100 mg) were diluted to 20 mL by saline solution. The mixture was infused continuously by a syringe pump at the speed of 5-10 mL/h. The pump speed was adjusted according to the anesthetic state and the duration of the operation. Arterial cannulation was punctured into the femoral artery with an indwelling needle, and was connected to pressure monitoring tubing for invasive blood pressure monitoring during the operation. Normally, the femoral arterial pulsation was palpated midway between the anterior superior iliac spine and the pubic symphysis. The operating area was isolated in an aseptic manner. The isolation was done with four pieces of disposable sterile sheets.

Surgical area was cut slightly medial to the line of the left fourth intercostal space, and a 4-5 cm transverse incision was made outward from the left side of the presternum. Monopolar diathermy was applied for both tissue cutting and coagulation purposes. The subcutaneous tissue and the muscular planes were dissected down to the pleura, entering the pleural space, and then the incision was widened by opening the forceps. A cotton bud was inserted to sweep the pleural space and push the lung away from the hole, and then the intercostal incision was widened to open the chest and expose the pericardium.

The heart was exposed via the left fourth intercostal thoracotomy incision (4-5 cm) and the apex and left auricle were identified. The epicardial end of the left anterior descending artery (LAD) was defined as level zero; the origin of the LAD under the left auricle was defined as level 100. The ligation was performed at 60% of the LAD. In addition, the major diagonal branch was also ligated parallel to the ligation site on the LAD artery in some monkeys, if the branching site of the diagonal artery was above the ligation site.

The artery was occluded for 1 minute followed by a 5-minute reperfusion, and this occlusion-reperfusion was repeated 3 times before the final ligation. After the final ligation, the difference of the left ventricular wall motion, color changes of the anterior ventricular wall, and alterations in the electrocardiogram and blood pressure were monitored to ensure that the ligation was successful. Methylene blue (1 mL) was injected bolus into left auricle with a 1.0 mL syringe after the final ligation. Filling defect of the methylene blue indicated completion of the ligation, as well as helped to predict the ischemic area.

Before closing the chest, heart conditions were intensively monitored for 45 minutes. Dobutamine (3-5 $\mu g \cdot kg^{-1} \cdot min^{-1}$) was infused to support the cardiac functions and defibrillator (HEARTSTART XL, Philips) was used if necessary. Care was taken to avoid damaging the heart during the pericardium closing. Sodium hyaluronate was infused into the pericardial chamber for anti-adhesion treatment. The pericardium and pleura were closed with 4-0 polyethylene sutures. The intercostal incision was closed with silk suture. To avoid pneumothorax, care was taken to avoid damaging the lung during the intercostal closing. The lungs were re-inflated while the intercostal incision was closed, so that air could be expelled from the pleural cavity. After the intercostal incision was closed, saline solution was dropped into the subcutaneous space, and the lung was inflated again to ascertain that the chest incision was closed tightly. The muscle and skin incisions were closed in layers with #2-0 silk sutures, and cleaned in a sterile manner. The endotracheal tube was retracted after spontaneous breathing was restored. The incision was covered with sterile gauze and bandage. Tramadol (2 mg/kg) was injected intramuscularly to relieve pain. The bandage was changed on alternate days and sutures were removed one week after the operation.

1.2 Electrocardiogram (ECG) Monitoring

A 12-lead ECG (MAC8000, GE, USA.) was recorded on the supine position of each monkey at the time before the operation, immediately after the operation (about 2 hours for the entire surgical procedure), and at four weeks and eight weeks after the operation using pediatric electrodes at 25 mm/s paper velocity and 10 mm/mV amplitude. The chest wall of a monkey was not wide enough to allow 6 precordial leads at the same time even with the pediatric electrodes. Therefore, the 6 precordial leads were divided into two groups: V1, V3, and V5 were recorded in one group, and V2, V4, and V6 were record in another group.

1.3 Echocardiography

Two-dimensional echocardiographic measurements were performed on standard apical 2- and 4-chamber views with three consecutive cardiac cycles. The frame rate was kept between 70 fps and 100 fps. All monkeys were subjected to transthoracic echocardiographic evaluation with the 10.3 MHz transducer (P10-4, Siemens ACUSON Antares System, German) in the left lateral position at the time before the operation, and at four weeks and at eight weeks after the operation.

The ejection fraction (EF) of the left ventricular was evaluated with the Simpson's single-plane method. Left-ventricular end-diastolic volume (LVEDV) and end-systolic volume (LVESV) were directly recorded, and EF was calculated using as follows: EF=(LVEDV−LVESV)/LVEDV× 100%. Stroke volume (SV) of the left ventricular was calculated as follows: SV=LVEDV−LVESV.

1.4 Trientine Treatment

Figure 11:
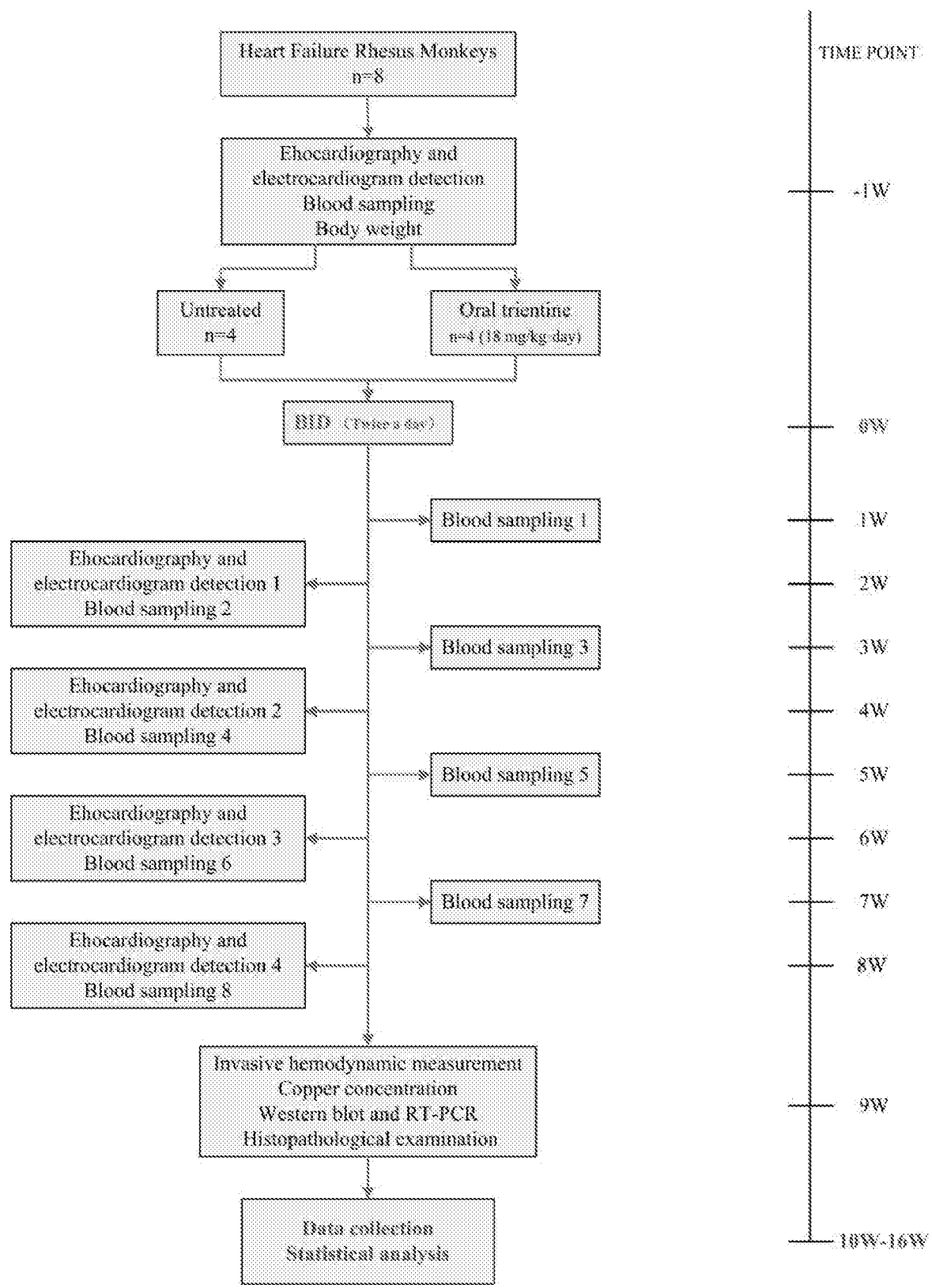
FIG. 11 shows a flow chart of the experimental procedure of Example 4.

One year after the operation, the ischemic cardiac tissue was fully replaced by collagenous fiber and became an infarcted tissue. A heart failure model was established as confirmed by ultrasound evaluations of cardiac functions. Trientine treatment was subsequently conducted. In the trientine-treated group, trientine was administered to each monkey orally two times daily. The dose of trientine was 18 mg/kg/day. This treatment was continued for eight weeks. Monkeys in the untreated (i.e. control) group did not receive any treatment. Cardiac functions and morphology were evaluated according to the schedule shown in FIG. 11 to assess therapeutic efficacy of trientine.

The experimental procedure and results in the following sections of the present example are focused on treatment with a trientine composition that consists essentially of trientine dihydrochloride. The same experimental protocol is used to assess therapeutic efficacy of other trientine compositions for treating heart failure in the Rhesus monkey model. For example, in one experiment, in addition to the trientine treatment, the Rhesus monkeys with heart failure in the treatment group are further treated with an oral copper supplement (such as copper chloride) at a dose of 16.5 mg/kg daily for 6 weeks. In another experiment, the trientine-copper complex of Example 1 is used to treat the Rhesus monkeys with heart failure in the treatment group at a dosage of 36.7 mg/kg/day by oral administration for 6 weeks.

1.5 Histopathological Examinations

Monkeys are sacrificed by intravenous injection of potassium chloride (10%, 10 mL) and a complete autopsy of each monkey is performed. Harvested hearts are washed and inspected grossly for visible lesions and fixed in 10% formaldehyde solution. Then, the heart is cut into six blocks from apex to base along the long axis. The thickness of each block is 0.5 cm. The surface of each section is smooth and uniform during the incision, and the sections are marked by ligature with label. Thin sections re cut and stained with Masson and H/E for microscopic examinations.

Immunohistochemistry

The tissue sections are examined using immunohistochemical methods to detect HIF-1α, VEGFA, and VEGFR1. The following antibodies are used respectively: mouse anti human HIF-1α monoclonal antibody (ab16066, Abcam); mouse anti human VEGFA monoclonal (sc-57496, Santa Cruz); rabbit anti human VEGFR1 monoclonal antibody (1303-12, Epitomics); mouse anti human CD31 monoclonal antibody (Maixin bio-tech company, Fuzhou). HIF-1α is retrieved by a high-pressure heat-induced antigen retrieval method using EDTA (pH 9.0), VEGF and VEGFR1 are retrieved by microwave heat-induced antigen retrieval methods using a citrate buffer solution (pH 6.0), and CD31 is retrieved by a microwave heat-induced antigen retrieval method using EDTA. The working concentrations of the antibodies are as follows: 1:800 for anti-HIF-1α, 1:100 for anti-VEGF, and 1:100 for anti-VEGFR1. The negative control samples are incubated with PBS in place of the first antibody in the immunohistochemical experiments. CD31 is a marker of endothelial cells. Ki-67 label is examined by immunofluorescence using confocal microscopy.

Capillary Density

Capillary densities of the tissue sections are assessed as follows. First, a maximum capillary distribution visual field is determined under a light microscope at 100 times magnification, and then 5 randomized visual fields are collected under the light microscope at 200 times magnification to determine the capillary density. Capillary is defined as a lumen with a diameter of less than the sum of 8 times the diameter of red blood cells. Measurement is performed by two independent technicians.

Semi-Quantitative Protein Expression Analysis

Immunohistochemistry slides are observed under a light microscope and images are taken and used to determine protein expression levels in a semi-quantitative manner using the Image-Pro Plus 6.0 image analysis software (Media Cybemetics). Slides of different groups are assessed by two independent technicians. Images from 5 randomized visual fields of the border area and remote areas from the infarct on each slide are taken under the light microscope at 400 times magnification.

1.6 Western Blot

Tissue Preparation

The heart is removed from the chest. The left ventricular wall is carefully examined and tissue samples from the infarcted area, the border area, and remote areas are isolated. The infarcted area can be distinguished from non-infarcted areas based on its pale appearance. The border area is defined as an area from 1 mm inside the infarcted area to 3 mm outside the infarcted area. Remote areas are defined as more than 3 mm outside the infarcted area. Samples are preserved in liquid nitrogen for Western blot analysis.

Western Blot

Protein extracts are obtained after grinding each tissue in liquid nitrogen and lysing of the ground tissue in the RIPA lysis buffer (Beyotime, CN) containing 1% complete EDTA-free protease inhibitor cocktail (Roche, DE) for 40 minutes on ice. Protein concentrations are determined by Pierce BCA Protein Assay Kit (Thermo SCIENTIFIC, 23227, USA). Equal amounts of protein (30 μg) from each sample are solubilized in 5×SDS sample buffer and separated on 10%-SDS and 8% polyacrylamide gels. Proteins are then electrophoretically transferred to a polyvinylidene fluoride membrane (Bio-Rad, USA). Membranes are blocked for 1 hour in Tris-buffered saline/Tween 20 (TBST) (10 mM Tris-HCl, pH 8.0, 150 mM NaCl, and 0.1% Tween 20) containing 5% nonfat dry milk (blocking solution), and incubated overnight at 4° C. with respective primary antibodies, such as anti-HIF-1α (Abcam, ab113642, USA), anti-VEGF (Santa Cruz, sc57496, USA), and anti-VEFGR-1(Abcam, ab32152, USA), diluted in the blocking solution according to the vender's recommendations. After washing with TBST, the membranes are incubated for 1 hour at 37° C. with appropriate secondary antibodies. Target proteins are visualized using a chemiluminescence HRP substrate (Millipore, USA) and analyzed by densitometry using the QUANTITY ONE™ Software.

1.7 mRNA Levels of HIF-1 Target Genes

In order to define HIF-1 transcription activities in the ischemic myocardium, mRNA levels of HIF-1α, HIF-1 target genes, such as VEGF and VEGFR-1 (also known as Flt-1), are determined by real-time PCR (RT-PCR).

Total RNA from each sample is isolated using TRIZOL® (Invitrogen, 15596-026, USA) per manufacturer's instructions. 1 μg of total RNA is reverse transcribed using the PRIMESCRIPT™ RT reagent Kit (TaKaRa, RR037A, Japan) at 37° C. for 15 minutes followed by 85° C. for 5 seconds and 4° C. for 5 minutes. Real-time RT-PCR reactions were performed using the SYBR® Premix Ex Taq™ II kit (TaKaRa, RR820A, Japan). To amplify the HIF-1α, VEGF and VEGFR1 cDNA fragments, the samples are processed using a BIO-RAD CFX96 Real-Time System with the following program: denature at 95° C. for 30 seconds, followed by 35 cycles of 95° C. for 5 seconds and 60° C. for 30 seconds. Results of the log-linear phase of the growth curve are analyzed and relative quantification is performed using the 2-ACT method. Gene expression levels of HIF-1α, VEGF and VEGFR1 are each normalized to the Actin expression level in each sample. At least 3 replicates are run for each sample. Primer sequences are shown in Table 2 below.

TABLE 2

Primer Sequences of RT-PCR

| Target Gene | | Primer Sequences |
|---|---|---|
| Rhesus monkey HIF-1α | forward primer | GTCTGCAACATGGAAGGTATTG (SEQ ID NO: 1) |
| | reverse primer | GCAGGTCATAGGTGGTTTCT (SEQ ID NO: 2) |
| Rhesus monkey VEGF | forward primer | GAGCTTCCTACAGCACAACA (SEQ ID NO: 3) |
| | reverse primer | CCAGGACTTATACCGGGATTTC (SEQ ID NO: 4) |
| Rhesus monkey VEGFR1 | forward primer | GGGTCACATCACCTAACATCAC (SEQ ID NO: 5) |
| | reverse primer | CCTTTCTGCTGTCCCAGATTAC (SEQ ID NO: 6) |
| Rhesus monkey Actin | forward primer | CCACGAAACTACCTTCAACTCC (SEQ ID NO: 7) |
| | reverse primer | GTGATCTCCTTCTGCATCCTGT (SEQ ID NO: 8) |

1.8 Copper Concentration in the Heart

Tissue samples were freshly frozen and stored at −80° C. before lyophilization. After lyophilization and digestion of the tissues with nitric acid, digests were colorless or light yellow, and clear with no visible precipitate or residue. Ultrapure water was added to each vessel to dilute $HNO_3$ to 2% for subsequent analyses of copper concentrations. Copper concentrations were determined by graphite furnace atomic absorption spectrophotometry (ICE3500, Thermo) according to the program shown in Table 1 of Example 3.

1.9 Statistical Analysis

All data were expressed as means±SD. The variation of each parameter was compared between the various experimental groups using the homogeneity of Levene's test and coefficient of variance (CV). A SPSS 14.0 statistical package (SPSS, Chicago, Ill.) was used, and significant difference was assumed when P values were <0.05.

2. Results 2.1 Cardiac Functions

Figure 12:
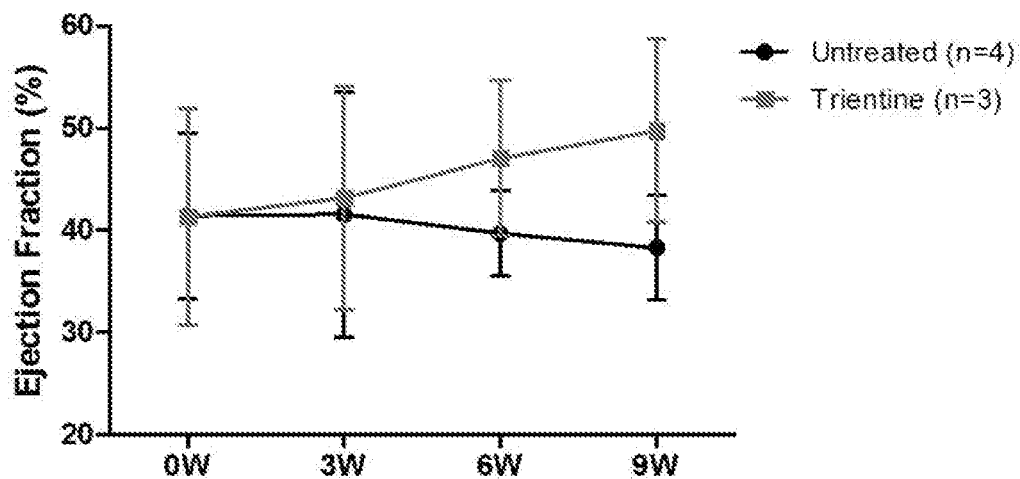
FIG. 12 shows echocardiography-detected changes in the left ventricular ejection fraction (EF) of Rhesus monkeys with heart failure in the untreated and trientine-treated groups.

Echocardiography examinations showed that, after trientine treatment, the left ventricular ejection fraction increased significantly over time. However, in the untreated group, the left ventricular ejection fraction decreased over time. See FIG. 12.

2.2 Copper Concentrations in the Infarcted Heart

Figure 13:
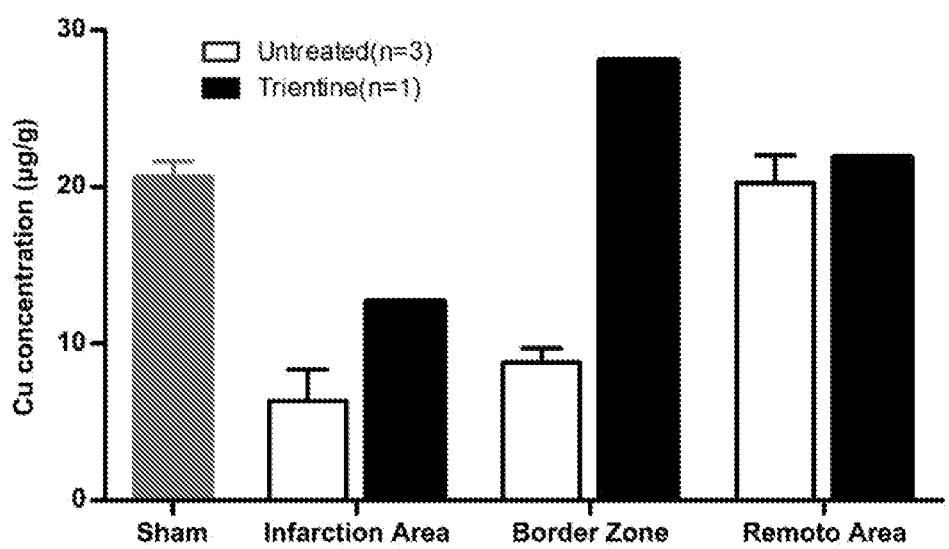
FIG. 13 shows copper concentrations in various tissue samples of Rhesus monkeys with heart failure in untreated and trientine-treated groups.

Copper concentration in the myocardium was determined by atomic absorption spectroscopy. As shown in FIG. 13, copper concentrations increased significantly after trientine treatment in tissue samples from the infarcted area and the border zone of the treated group as compared to that of the untreated group. By contrast, the copper concentrations of tissue samples in the remote areas are comparable in the trientine-treated group and the untreated group.

3. Discussion

Myocardial ischemia leads to HIF-1α accumulation and copper depletion. Under ischemic conditions, the accumulated HIFα cannot be activate HIF transcription because copper is required for HIF transcriptional complex formation and for interaction of HIF with the HIF response element (HRE) sequences in target genes. Therefore, although HIF accumulation takes place in the ischemic myocardium, copper deficiency blocks HIF-regulated expression of genes involved in angiogenesis, which leads to suppression of myocardial angiogenesis. This effect results in myocardial infarction, which further progresses to heart failure.

The present study used trientine to increase the copper concentrations in local ischemic tissues for myocardial infarction treatment. The results showed that trientine promoted tissue redistribution and reuse of copper. Furthermore, echocardiography examinations showed that the cardiac functions were improved after the trientine treatment. The dose of trientine in this experiment was 18 mg/kg per day for the rhesus monkeys, which is equivalent to about 420 mg per day for a human individual. Compared to typical doses of trientine used to decrease serum copper level in patients with Wilson's disease (500-700 mg/day up to a maximum of 1500 mg/day for pediatric patients, and 750-1250 mg/day up to a maximum of 2000 mg/day for adult patients), the dose used in this experiment is much lower. The results of this experiment provide strong evidence that the low-dose trientine treatment described herein is an effective strategy to deliver copper in vivo for treatment of myocardial infarction.

Figure 14:
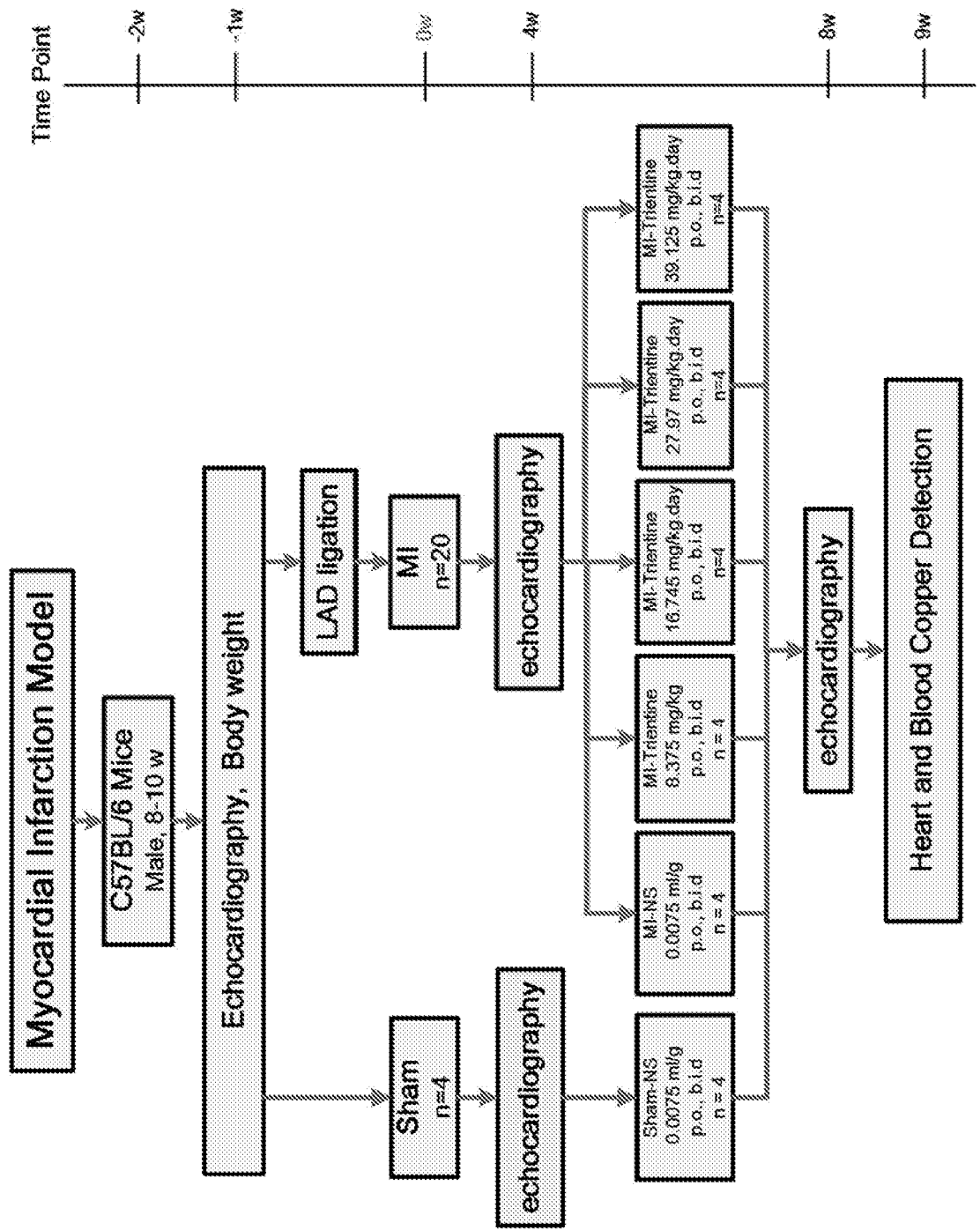
FIG. 14 shows a flow chart of the experimental procedure of Example 5.

Example 5. Trientine Therapy in the Mice Model of Myocardial Ischemic Infarction In this experiment, a mouse model of myocardial ischemic infarction was established by a permanent coronary artery ligation operation. At 4 weeks after the operation, the ischemic cardiac tissue was replaced by collagenous fiber and became an infarcted tissue. Trientine treatments were conducted as described in the protocol shown in FIG. 14.

Trientine treatment was administered to four groups of modelized mice via intragastric route twice a day at a dose of 16.75, 33.49, 55.94, or 78.25 mg/kg per day. This treatment was continued for 4 weeks. The untreated group did not receive any trientine treatment.

Echocardiography

Cardiac functions were evaluated by echocardiography to assess therapeutic efficacy of trientine. All mice were subjected to transthoracic echocardiographic evaluation with a 12 MHz transducer (i13L, Vivid7, GE Ultrasound). The ejection fraction (EF) of the left ventricular was evaluated with the Simpson's single-plane method. Left-ventricular end-diastolic volume (LVEDV) and end-systolic volume (LVESV) were directly recorded, and EF was calculated using as follows: EF=(LVEDV−LVESV)/LVEDV×100%.

Copper Concentration in the Heart

Tissue samples were freshly frozen and stored at −80° C. before lyophilization. After lyophilization and digestion of the tissues with nitric acid, digests were colorless or light yellow, and clear with no visible precipitate or residue. Ultrapure water was added to each vessel to dilute $HNO_3$ to 2% for subsequent analyses of copper concentrations. Copper concentrations were determined by graphite furnace atomic absorption spectrophotometry (ICE3500, Thermo) according to the program shown in Table 1 of Example 3.

Results

Figure 15:
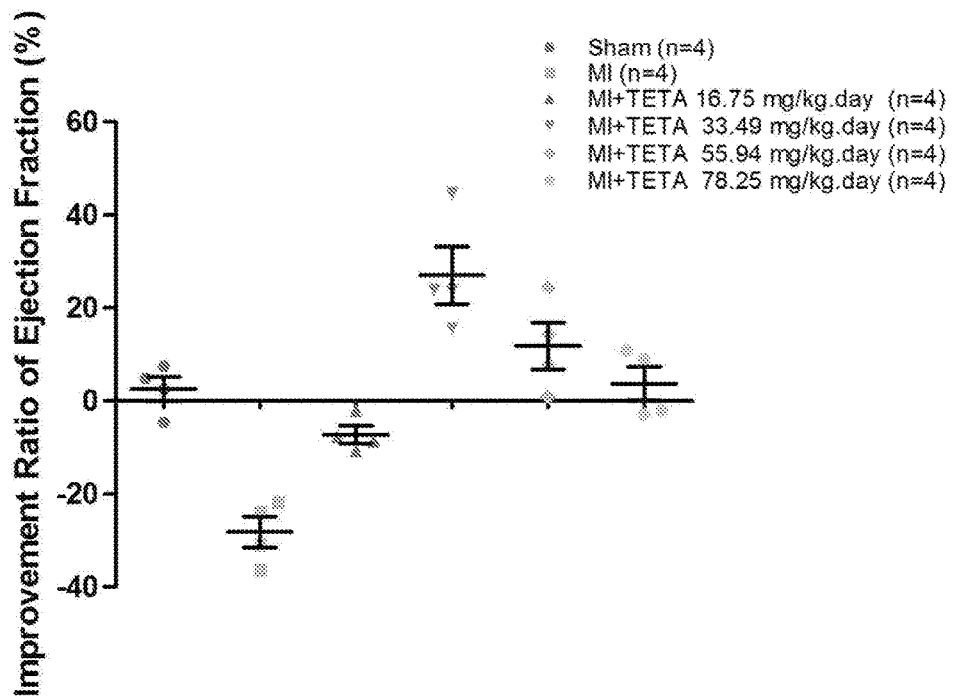
FIG. 15 shows echocardiography-detected changes in the left ventricular ejection fraction (LVEF) of mice with myocardial infarction in untreated and trientine-treated groups.
Figure 16:
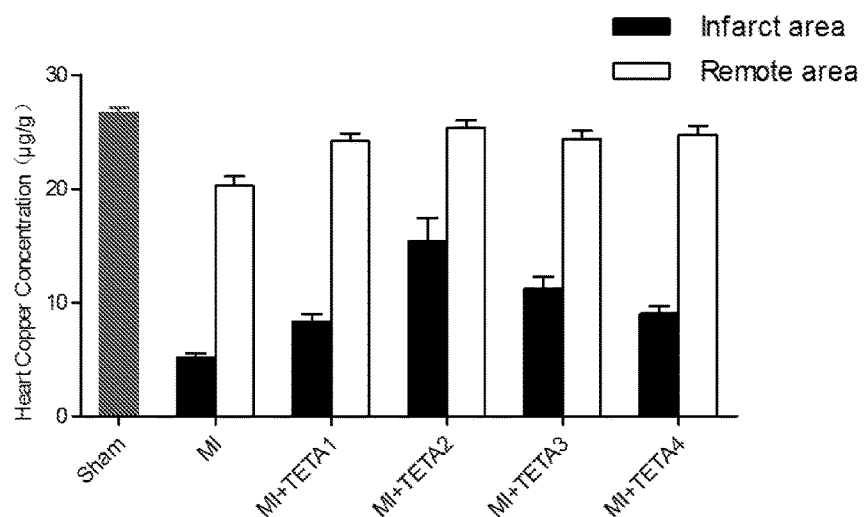
FIG. 16 shows copper concentrations in various tissue samples of mice with myocardial infarction in untreated and trientine treated groups.

Cardiac performance detected by echocardiography showed that the cardiac function as measured by the left ventricular ejection fraction of the mice treated with trientine improved at lower doses of trientine treatment, and such improvement decreased at higher doses of trientine treatment (see FIG. 15. The improvement ratio of ejection fraction reached a peak with the dose of 33.49 mg/kg per day, and then decreased even with a higher dose. This experiment suggested that the trientine therapy for myocardial infarction is effective within a narrow low-dose range. As shown in FIG. 16, copper concentration in the infarcted area increased significantly in response to the trientine treatment. Notably, in the treatment group with the dose of 33.49 mg/kg per day, the copper content in the infarct area was the highest.

Discussion

The present study used a series of increasing doses of trientine to treat myocardial ischemic infarction in mice. The results showed that in the group treated with trientine at a dose of 33.49 mg/kg per day, the copper content in the infarcted area was highest among all experimental groups, which corresponds to the highest improvement ration of ejection fraction observed in this group compared to the other experimental groups. At higher trientine doses tested, no further improvement in the copper content of the infarcted area or ejection fraction were observed.

The doses, 16.75, 33.49, 55.94, and 78.25 mg/kg per day, tested in this experiment are equivalent to about 150, 300, 500, and 700 mg per day respectively for a human patient. By contrast, the trientine dose used to treat Wilson's disease by decreasing serum copper level in those patients is about 500-700 mg per day up to a maximum of 1500 mg per day for pediatric patients, and about 750 mg-1250 mg per day up to a maximum of 2000 mg per day for adult patients. Thus, the dose of trientine with the highest efficacy of replenishing copper level in ischemic heart tissue and restoring cardiac functions observed in this experiment is much lower than the doses used in treating Wilson's disease patients. The results of this experiment provide strong evidence that the trientine therapy for myocardial infarction is effective within a narrow low-dose range.

Without being bound by any theory or hypothesis, trientine may serve as a copper delivery shuttle to transfer copper from a high concentration tissue or environment (such as serum following ischemia) to a copper-deprived ischemic tissue in the heart, thereby relieving copper depletion in the ischemic tissue and improving the cardiovascular conditions. Several publications describe elevated copper level in the serum of patients having cardiovascular diseases, especially myocardial infarction. See, for example, E S Ford. *Am. J. Epidem.* 151 (12): 1182 (2000); E. Gomez et al. *J. Trace Elements Med. Biol.* 14: 65-70 (2000); and Singh M M et al. *Angiology—Journal of Vascular Diseases,* 504-506 (1985)

Example 6. A Clinical Study of Trientine Therapy in Heart Failure Patients

A clinical study is conducted to assess the clinical effects of low-dose trientine treatment on patients having heart failure. The primary objective of the study is to evaluate the efficacy of trientine as compared to placebo on treating heart failure patients before and after the treatment.

The study is a randomized, double-blinded, placebo-controlled clinical study in heart failure patients (e.g., NYHA functional class II and III) with reduced ejection fraction (e.g., LVEF 35%). Patients in the control group are given standard of care (SOC) plus twice daily placebo. Patients in the treatment group are given SOC plus oral administration of trientine twice daily at 150 mg/dose. Patients are assessed at screening, baseline (week 0), through the course of treatment, and after the treatment.

Primary endpoint of the study may be survival, hospitalization related to heart failure, or change in a biomarker related to heart failure. For example, the levels of circulating natriuretic peptides over time have been used to stratify risk of heart failure, and thus can serve as biomarkers for heart failure severity.

Secondary endpoints of the study may include change in cardiac structure and function from baseline to the end of the treatment. Cardiac structure and function can be determined by echocardiography. Exemplary metrics that may serve as secondary endpoints include left ventricular end-diastolic volume, left-ventricular ejection fraction, and E/E' ratio. Secondary endpoints of the study may further include functional status based on the six-minute walk distance test, changes in symptoms (NYHA class), and Quality of Life scores.

Serum copper levels and other biomarkers may be monitored as tertiary endopoinds of the study.

Safety is assessed by reviewing subject-reported spontaneous adverse events (AEs) and other appropriate medical and safety assessments, such as vital signs, ECG, laboratory tests, etc.

The invention claimed is:

1. A method of increasing intracellular copper level in an ischemic heart tissue of an individual having ischemic heart tissue injury, comprising administering to the individual an effective amount of a composition comprising trientine, wherein the effective amount of the composition comprises about 80 mg to about 700 mg of trientine per day, wherein the individual is a human.

2. The method of claim 1, wherein the composition further comprises a copper ion.

3. The method of claim 2, wherein the copper ion in the composition is complexed with trientine.

4. The method of claim 3, wherein the complex of trientine and the copper ion is crystalline.

5. The method of claim 4, wherein the composition comprises a crystalline complex of trientine and a copper ion, wherein the copper ion is chelated by the four amine groups of trientine to adopt a square-planar geometry, and wherein the crystalline complex further comprises two chloride ions and a water molecule.

6. The method of claim 2, wherein the copper ion in the composition is not complexed with trientine.

7. The method of claim 1, wherein the individual has a compromised tissue repair system.

8. The method of claim 1, wherein the composition is administered at least two times daily.

9. The method of claim 1, wherein the composition is administered for at least about one month.

10. The method of claim 1, wherein administration of the composition leads to at least about 0.005 mg/L of trientine in the blood.

11. The method of claim 1, further comprising monitoring intracellular copper level in the individual.

12. The method of claim 1, wherein the composition is administered orally.

13. The method of claim 1, wherein trientine is in the form of a hydrochloride salt.

14. A method of increasing intracellular copper level in an ischemic heart tissue of an individual having ischemic heart tissue injury, comprising administering to the individual an effective amount of a composition comprising trientine, further comprising administering to the individual an effective amount of a copper ion, wherein the effective amount of the composition comprises about 80 mg to about 700 mg of trientine per day, wherein the individual is a human.

15. The method of claim 14, wherein the individual has a compromised tissue repair system.

16. The method of claim 14, wherein the composition is administered at least two times daily.

17. The method of claim 14, wherein the composition is administered for at least about one month.

18. The method of claim 14, wherein administration of the composition leads to at least about 0.005 mg/L of trientine in the blood.

19. The method of claim 14, further comprising monitoring intracellular copper level in the individual.

20. A method of treating ischemic heart failure in an individual, comprising administering to the individual an effective amount of a composition comprising trientine, wherein the individual is a human, and wherein the effective amount of the composition comprises about 80 mg to about 700 mg of trientine per day.

21. The method of claim 20, wherein the individual has class II or class III heart failure based on New York Heart Association (NYHA) functional classification.

22. The method of claim 20, wherein the composition is administered orally.

23. The method of claim 20, wherein trientine is in the form of a hydrochloride salt.

\* \* \* \* \*